United States Patent
Schwab et al.

(10) Patent No.: US 11,198,731 B2
(45) Date of Patent: Dec. 14, 2021

(54) COMBINATIONS OF CABOZANTINIB AND ATEZOLIZUMAB TO TREAT CANCER

(71) Applicant: Exelixis, Inc., Alameda, CA (US)

(72) Inventors: Gisela Schwab, Hayward, CA (US); Christian Scheffold, Palo Alto, CA (US); Colin Hessel, Redwood City, CA (US)

(73) Assignee: Exelixis, Inc., Alameda, CA (US)

( * ) Notice: Subject to any disclaimer, the term of this patent is extended or adjusted under 35 U.S.C. 154(b) by 4 days.

(21) Appl. No.: 16/479,143

(22) PCT Filed: Jan. 19, 2018

(86) PCT No.: PCT/US2018/014523
§ 371 (c)(1),
(2) Date: Jul. 18, 2019

(87) PCT Pub. No.: WO2018/136796
PCT Pub. Date: Jul. 26, 2018

(65) Prior Publication Data
US 2019/0352403 A1 Nov. 21, 2019

Related U.S. Application Data

(60) Provisional application No. 62/458,447, filed on Feb. 13, 2017, provisional application No. 62/448,869, filed on Jan. 20, 2017.

(51) Int. Cl.
| | | |
|---|---|---|
| C07K 16/28 | (2006.01) | |
| A61P 35/04 | (2006.01) | |
| A61K 31/47 | (2006.01) | |
| A61K 39/395 | (2006.01) | |
| A61K 45/06 | (2006.01) | |
| A61K 39/00 | (2006.01) | |

(52) U.S. Cl.
CPC .......... *C07K 16/2827* (2013.01); *A61K 31/47* (2013.01); *A61K 39/39558* (2013.01); *A61K 45/06* (2013.01); *A61P 35/04* (2018.01); *A61K 2039/545* (2013.01)

(58) Field of Classification Search
CPC ..... C07K 16/2827; A61P 35/04; A61K 31/47; A61K 45/06; A61K 2039/545
See application file for complete search history.

(56) References Cited

FOREIGN PATENT DOCUMENTS

| | | |
|---|---|---|
| WO | 2010077634 | 7/2010 |
| WO | 2010083414 | 7/2010 |
| WO | WO-2010083414 A1 * 7/2010 | ............. A61P 25/00 |
| WO | 2012009722 | 1/2012 |
| WO | 2017181187 | 10/2017 |
| WO | 2017184597 | 10/2017 |

OTHER PUBLICATIONS

Markham A., Atezolizumab: first global approval, Drugs, 2016, 76:1227-1232, Publication Date: Jul. 13, 2016 (Year: 2016).*
Yakes et al. Cabozantinib (XL184), a Novel MET and VEGFR2 Inhibitor, Simultaneously Suppresses Metastasis, Angiogenesis, and Tumor Growth, Molecular Cancer Therapeutics, 2011, 10(12):2298-2308, Publication Date: Sep. 16, 2011 (Year: 2011).*
Cabometyx Highlights of Prescribing Information, Reference ID: 3924269, Publication Date: Apr. 2016 (Year: 2016).*
Tencentriq, Highlights of Prescribing Information, Publication Date: Dec. 31, 2016 (Year: 2016).*
International Search Report for PCT/US2018/014523, dated May 7, 2018.
Powles, et al., "Phase 1b Trial of Cabozantinib in Combination with Atezolizumab in Patients with Locally Advanced or Metastatic Renal; Cell Carcinoma and Urothelial Carcinoma", European Urology Supplements, vol. 16, No. 10, Nov. 16, 2017.
Agarwal, et al., "Cabozantinib (C) in combination with atezolizumab (A) in patients with metastatic castration-resistant prostate cancer (mCRPC): Results of Cohort 6 of the COSMIC-021 Study." Journal of Clinical Oncology, 2020 American Society of Clinical Oncology.
Anonymous, Highlights of Prescribing Information, Tencentriq, Publication Date: Dec. 31, 2016 (Year: 2016).
Anonymous, Highlights of Prescribing Information Cometriq, Reference ID 3223542, Publication Date Nov. 2012, Year 2012.
Anonymous, Highlights of Prescribing Information Cabometyx, Reference ID: 3924269, Publication Date: Apr. 2016 (Year: 2016).
Goodman, Novel Combination of Cabozantinib Plus Atezolizumab Shows Benefit in Patients With Advanced Prostate Cancer:, The ASCO Post, Mar. 10, 2020.
Lu X., et al., Effective combinatorial immunotherapy for castration-resistant prostate cancer. Nature, Mar. 20, 2017, vol. 543, No. 7647, pp. 728-732.
Manegold C., et al., The Potential of Combined Immunotherapy and Antiangiogenesis for the Synergistic Treatment of Advanced NSCLC. Journal of Thoracic Oncology, Oct. 8, 2016, vol. 12, No. 2, pp. 194-207 Abstract, Table 3, p. 204.
NCT02496208: Cabozantinib-s-malate and Nivolumab With or Without Ipilimumab in Treating Patients With Metastatic Genitourinary Tumors. Aug. 2, 2016.

(Continued)

*Primary Examiner* — Peter J Reddig
*Assistant Examiner* — Cheng Lu
(74) *Attorney, Agent, or Firm* — Honigman LLP; Heidi M. Berven; Andrew S. Chipouras

(57) ABSTRACT

This invention relates to the combination of cabozantinib and atezolizumab to treat locally advanced or metastatic solid tumors, particularly advanced urothelial cancer or renal cell carcinoma.

17 Claims, No Drawings

(56) References Cited

OTHER PUBLICATIONS

Roche's Tecentriq (atezolizumab) shows significant survival advantage compared to chemotherapy regardless of PD-L1 status in a specific type of lung cancer in Phase III study. Oct. 9, 2016.
Yakes, et al., "Cabozantinib (XL184), a novel MET and VEGFR2 inhibitor, simultaneously suppresses metastasis, angiogenesis and tumor growth", Mol Cancer Ther, No. 10, pp. 2298-2308, Sep. 16, 2011.

\* cited by examiner

COMBINATIONS OF CABOZANTINIB AND ATEZOLIZUMAB TO TREAT CANCER

CROSS-REFERENCE TO RELATED APPLICATIONS

This application is a United States National Phase filing of PCT/US2018/014523, filed Jan. 19, 2018, which claims the benefit of priority to U.S. Provisional Application No. 62/458,447, filed Feb. 13, 2017, and to U.S. Provisional Application No. 62/448,869, filed Jan. 20, 2017, the entire contents of which are incorporated herein by reference.

FIELD OF INVENTION

This invention relates to the combination of cabozantinib and atezolizumab to treat locally advanced or metastatic solid tumors.

BACKGROUND OF THE INVENTION

Multi-targeted tyrosine kinase inhibitors (TKIs) and immune checkpoint inhibitors (ICIs) represent two systemic modalities that have been instrumental in the recent advancements of anticancer treatment over the past several years. Both classes of therapies have demonstrated broad clinical effects leading to new approved treatment options across multiple tumor types including renal cell carcinoma (RCC), urothelial carcinoma (UC), melanoma, non-small-cell lung cancer (NSCLC), and others. The success of these therapy types as single agents with distinct mechanisms of action has naturally led to interest in evaluating combinations of TKIs with ICIs in search of further, possibly synergistic, anticancer clinical effects.

Atezolizumab (TECENTRIQ®)(Genentech Oncology, a subsidiary of Roche) Atezolizumab is a humanized immunoglobulin (Ig) G1 monoclonal antibody that targets programmed death receptor 1 ligand (PD-L1) and inhibits the interaction between PD-L1 and its receptors, programmed death receptor 1 (PD-1) and B7-1 (also known as CD80), both of which function as inhibitory receptors expressed on T cells. It is approved in the United States and the European Union for the treatment of patients with localized advanced or metastatic UC after prior platinum-containing chemotherapy or who are considered cisplatin-ineligible (Rosenberg et al 2016, Loriot et al 2016). Atezolizumab is also approved for patients with locally advanced or metastatic NSCLC after prior chemotherapy (Fehrenbacher et al 2016; Tecentriq US Prescribing Information; EMA SmPC). Patients with epidermal growth factor receptor (EGFR) activating mutations or anaplastic lymphoma kinase (ALK)-positive tumor mutations should also have received targeted therapy before receiving atezolizumab. Further, atezolizumab has demonstrated clinical activity in treatment-naïve and chemotherapy experienced PD-L1 positive advanced-stage NSCLC (Peters et al 2017) and in advanced RCC as single agent (McDermott et al 2016) and in combination with a vascular endothelial growth factor (VEGF)-targeting antibody, bevacizumab (Sznol et al 2015). In addition, atezolizumab is currently being evaluated in combination with enzalutamide in metastatic castration-recurrent prostate cancer (CRPC; NCT03016312). Resistance to enzalutamide in CRPC has been associated with upregulated PD-L1 expression (Bishop et al 2015) and early clinical data suggest that ICI therapy may provide clinical benefits in CRPC patients following progression on enzalutamide (Graff et al 2016).

In spite of these advances, there is still room for improvement. There is also still a need for the development of novel systemic therapies for locally advanced or metastatic solid tumors.

SUMMARY OF THE INVENTION

These and other needs are met by the present invention, which is directed to a method of treating a locally advanced or a metastatic solid tumor, comprising administering a patient in need of such treatment a compound of formula I:

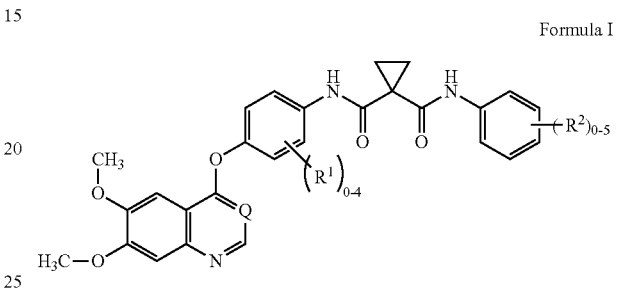

Formula I or a pharmaceutically acceptable salt thereof or a pharmaceutical composition comprising the compound of formula I or a pharmaceutically acceptable salt thereof and a pharmaceutically acceptable carrier, wherein:

$R^1$ is halo;

$R^2$ is halo; and

Q is CH or N;

in combination with atezolizumab. The locally advanced or a metastatic solid tumor may be advanced UC, RCC, castration-recurrent prostate cancer (CRPC) and non-small cell lung cancer (NSCLC).

Another aspect is directed to a method of treating locally advanced or a metastatic solid tumor, comprising administering a patient in need of such treatment compound 1:

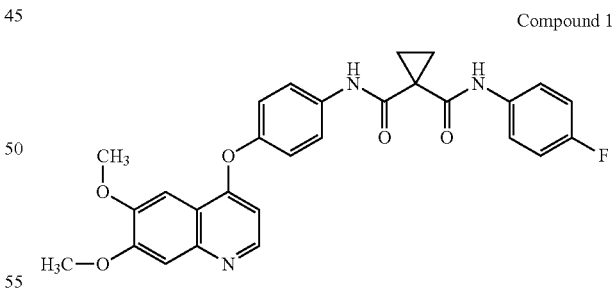

Compound 1 or a pharmaceutically acceptable salt thereof or a pharmaceutical composition comprising compound 1 or a pharmaceutically acceptable salt thereof and a pharmaceutically acceptable carrier, in combination with atezolizumab. The locally advanced or a metastatic solid tumor may be advanced UC, RCC, CRPC, and NSCLC.

In another aspect, the invention comprises a pharmaceutical dosage form comprising a compound of formula I or compound 1, or a pharmaceutically acceptable salt thereof, with atezolizumab.

Definitions

| | |
|---|---|
| ACTH | adrenocorticotropic hormone |
| ADT | androgen deprivation therapy |
| AE | adverse event |
| AESI | adverse event of special interest |
| AIDS | acquired immunodeficiency syndrome |
| ALK | anaplastic lymphoma kinase |
| ALP | alkaline phosphatase |
| ALT | alanine aminotransferase |
| ANC | absolute neutrophil count |
| AST | aspartate aminotransferase |
| AUC | area under the plasma drug concentration-vs-time curve |
| BP | blood pressure |
| BSR | bone scan response |
| BUN | blood urea nitrogen |
| C#D# (eg, C1D1) | Cycle # Day # |
| CAP | chest/abdomen/pelvis |
| CBC | complete blood count |
| CFR | Code of Federal Regulations |
| CI | confidence interval |
| CNS | central nervous system |
| CR | complete response |
| CRC | Cohort Review Committee |
| CRF | case report form |
| CRPC | castration-recurrent prostate cancer |
| CT | computerized tomography |
| CTCAE | Common Terminology Criteria for Adverse Events |
| CTEP | Cancer Therapy Evaluation Program |
| CYP | cytochrome P450 |
| ddMVAC | dose-dense methotrexate, vinblastine, doxorubicin, and cisplatin |
| DILI | drug-induced liver injury |
| DLT | dose-limiting toxicity |
| DOR | duration of response |
| DVT | deep vein thrombosis |
| EC | Ethics Committee |
| ECG | electrocardiogram |
| ECOG | Eastern Cooperative Oncology Group |
| EGFR | epidermal growth factor receptor |
| ESC | Executive Safety Committee |
| FACS | fluorescence-activated cell sorting |
| FDA | Food and Drug Administration |
| FSH | follicle-stimulating hormone |
| FXa | Factor Xa |
| GCP | Good Clinical Practice |
| GFR | glomerular filtration rate |
| GI | gastrointestinal |
| GLP | Good Laboratory Practice |
| GnRH | gonadotropin-releasing hormone |
| GU | genitourinary |
| HBsAg | Hepatitis B surface antigen |
| HCV | Hepatitis C virus |
| HCV Ab | Hepatitis C virus antibody |
| HIV | human immunodeficiency virus |
| HR | hazard ratio |
| ICF | informed consent form |
| ICH | International Conference on Harmonisation |
| ICI | Immune checkpoint inhibitor |
| Ig | immunoglobulin |
| IHC | immunohistochemical |
| IMDC | International Metastatic RCC Database Consortium |
| INR | International Normalized Ratio |
| irAE | immune-related adverse event |
| IRB | Institutional Review Board |
| IRC | independent radiology committee |
| IRF | independent review facility |
| irSAE | immune-related serious adverse events |
| ITT | intent-to-treat |
| IV | intravenous |
| LDH | lactate dehydrogenase |
| LFT | liver function test |
| LH | luteinizing hormone |
| LMWH | low molecular weight heparins |
| MDSC | myeloid-derived suppressor cell |
| MedDRA | Medical Dictionary for Regulatory Activities |
| MHC | major histocompatibility complex |
| MI | myocardial infarction |
| MMR | mismatch repair |
| MRI | magnetic resonance imaging |
| MSI | microsatellite instability |
| MSKCC | Memorial Sloan-Kettering Cancer Center |
| MTC | medullary thyroid cancer |
| MTD | maximum tolerated dose |
| NA | Not applicable |
| NCCN | National Comprehensive Cancer Network |
| NCI | National Cancer Institute |
| NE | not estimable |
| NR | Not reported |
| NSAID | Non-steroid anti-inflammatory drug |
| NSCLC | non-small cell lung cancer |
| ONJ | osteonecrosis of the jaw |
| ORR | objective response rate |
| OS | overall survival |
| PD | progressive disease |
| PD-1 | programmed death receptor 1 |
| PD-L1 | programmed death receptor 1 ligand |
| PFS | progression-free survival |
| PK | pharmacokinetic or pharmacokinetics |
| PO | By mouth |
| PPE | palmar-plantar erythrodysesthesia |
| PPI | proton pump inhibitor |
| PR | partial response |
| PSA | prostate-specific antigen |
| PT | prothrombin time |
| PTT | partial thromboplastin time |
| qd | once daily |
| qod | every other day |
| QTcF | Corrected QT interval calculated by the Fridericia formula |
| RCC | renal cell carcinoma |
| RECIST (1.1) | Response Evaluation Criteria in Solid Tumors (version 1.1) |
| RPLS | reversible posterior leukoencephalopathy syndrome |
| RSI | reference safety information |
| RTK | receptor tyrosine kinase |
| SAE | serious adverse event |
| SAP | statistical analysis plan |
| SD | stable disease |
| SI | Système Internationale |
| SLD | Sum of lesion diameter |
| SNP | single nucleotide polymorphism |
| SoD | Sum of the diameters |
| T3 | triiodothyronine |
| T4 | thyroxine |
| TAM | tumor-assisted macrophage |
| TBS | technetium bone scan |
| TIA | transient ischemic attack |
| TKI | tyrosine kinase inhibitor |
| TPR | time point response |
| $T_{reg}$ | regulatory T-cell |
| TSH | thyroid-stimulating hormone |
| UC | urothelial carcinoma |
| ULN | upper limit of normal |
| UPCR | urine protein/creatinine ratio |
| VAD | ventricular assist device |
| VEGF | vascular endothelial growth factor |
| VEGFR | vascular endothelial growth factor receptor |
| W#D# | Week # Day # |
| WBC | white blood cell |

DETAILED DESCRIPTION

As indicated above, the invention is directed to a method of treating a locally advanced or a metastatic solid tumor, comprising administering a compound of formula I or compound 1 or a pharmaceutically acceptable salt thereof in combination with atezolizumab.

Compound 1 is known by its chemical name N-(4-{[6,7-bis(methyloxy)quinolin-4-yl]oxy}phenyl)-N'-(4-fluorophenyl)cyclopropane-1,1-dicarboxamide and by the name cabozantinib. COMETRIQ™ (Cabozantinib S-Malate oral capsules) has been approved by the Food and Drug Administration (FDA) in the United States for the treatment of patients with progressive, metastatic medullary thyroid cancer (MTC) on Nov. 29, 2012. CABOMETYX™ (Cabozantinib S-Malate oral tablets) has been approved by the Food and Drug Administration (FDA) in the United States for the treatment of advanced renal cell carcinoma (RCC) who have received prior antiangiogenic therapy on Apr. 25, 2016. Cabozantinib is formulated as the L-malate salt of N-(4-{[6,7-bis(methyloxy)quinolin-4-yl]oxy}phenyl)-N'-(4-fluorophenyl)cyclopropane-1,1-dicarboxamide. WO 2005/030140, the entire contents of which is incorporated herein by reference, discloses compound 1 and describes how it is made and also discloses the therapeutic activity of this compound to inhibit, regulate, and/or modulate the signal transduction of kinases (Assays, Table 4, entry 289). In November, 2012, cabozantinib achieved regulatory approval in the United States for the treatment of progressive metastatic medullary thyroid cancer. WO 2005/030140 describes the synthesis of cabozantinib (Example 48) and also discloses the therapeutic activity of this molecule to inhibit, regulate, and/or modulate the signal transduction of kinases (Assays, Table 4, entry 289). Example 48 begins at paragraph [0353] in WO 2005/030140. Information for Compound 1 is available from the FDA at http://www.accessdata.fda.gov/scripts/cder/daf/index.cfm?event=overview.process&ApplNo=208692 (last visited Dec. 19, 2016) and is incorporated herein by reference in its entirety.

Atezolizumab is known by the name TECENTRIQ®, (Genentech Oncology, a subsidiary of Roche Group). Atezolizumab achieved regulatory approval from the Food and Drug Administration (FDA) in the United States on May 18, 2016 for the treatment of locally advanced or metastatic urothelial carcinoma who: have disease progression during or following platinum-containing chemotherapy, and have disease progression within 12 months of neoadjuvant or adjuvant treatment with platinum-containing chemotherapy. Atezolizumab achieved regulatory approval from the Food and Drug Administration (FDA) in the United States on Oct. 18, 2016 for the treatment of Metastatic non-small cell lung cancer in patients with metastatic non-small cell lung cancer (NSCLC) who have disease progression during or following platinum-containing chemotherapy.

Information concerning atezolizumab is available from the FDA at http://www.fda.gov/Drugs/InformationOnDrugs/ApprovedDrugs/ucm525780.html (last visited Dec. 19, 2016), and is incorporated herein by reference in its entirety.

In these and other embodiments, the compound of formula I or compound 1, or a pharmaceutically acceptable salt thereof, is administered as a pharmaceutical composition, wherein the pharmaceutical composition additionally comprises a pharmaceutically acceptable carrier, excipient, or diluent. In a specific embodiment, the compound of formula I is compound 1, or a pharmaceutically acceptable salt thereof.

The compound of formula I or compound 1, or a pharmaceutically acceptable salt thereof as described herein, includes both the recited compounds as well as individual isomers and mixtures of isomers. In each instance, the compound of formula I includes the pharmaceutically acceptable salts, hydrates, and/or solvates of the recited compounds and any individual isomers or mixture of isomers thereof.

In other embodiments, the compound of formula I or compound 1 can be the (L)-malate salt (also referred to as the S-malate salt), or the (D)-malate salt (also referred to as the R-malate salt). The malate salt of the compound of formula I and of compound 1 is disclosed in PCT/US2010/021194 and U.S. Patent Application Ser. No. 61/325,095, the entire contents of each of which are incorporated herein by reference.

In other embodiments, the compound of formula I can be malate salt.

In other embodiments, the compound of formula I can be the (D)-malate salt.

In other embodiments, the compound of formula I can be the (L)-malate salt.

In other embodiments, compound 1 can be the malate salt.

In other embodiments, compound 1 can be (D)-malate salt.

In other embodiments, compound 1 can be the (L)-malate salt.

In another embodiment, the malate salt is in the crystalline N-1 form of the (L) malate salt and/or the (D) malate salt of the compound 1 as disclosed in U.S. Patent Application Ser. No. 61/325,095. See also WO 2008/083319 for the properties of crystalline enantiomers, including the N-2 crystalline forms of the (L)-malate salt, (also referred to as the S-malate salt) or the (D)-malate salt, (also referred to as the R-malate salt) and/or the N-1 crystalline forms of the (L)-malate salt, (also referred to as the S-malate salt) or the (D)-malate salt, (also referred to as the R-malate salt) of compound 1. Methods of making and characterizing such forms are fully described in PCT/US10/21194, which is incorporated herein by reference in its entirety.

In one embodiment the compound of formula I or compound 1, or a pharmaceutically acceptable salt thereof is administered concurrently (at the same time) or sequentially (one after the other) with atezolizumab. In a further embodiment, compound 1 or a pharmaceutically acceptable salt thereof is administered once daily, and atezolizumab is administered once every three weeks (q3wk). In a further embodiment, a compound of formula I or compound 1, or a pharmaceutically acceptable salt thereof, is administered with fasting (i.e., without eating) for approximately two hours before and 1 hour after administration. The compound of formula I, or compound 1, or a pharmaceutically acceptable salt thereof is preferably administered with a glass of water (approximately 8 ounces or 240 mL).

In another embodiment, the compound of formula I or compound 1, or a pharmaceutically acceptable salt thereof is administered orally once daily as a tablet or capsule. In another embodiment, atezolizumab is administered intravenously (IV) once every three weeks (q3wk) as an infusion.

In another embodiment, compound of formula I or compound 1, or a pharmaceutically acceptable salt thereof is administered orally as its free base or malate salt as a capsule or tablet.

The amounts of the compound of formula I or compound 1, or a pharmaceutically acceptable salt thereof that are administered will vary. In one embodiment, the compound of formula I or compound 1, or a pharmaceutically acceptable salt thereof is administered as one 60 mg tablet. In another embodiment, the amount of the compound of formula I or compound 1, or a pharmaceutically acceptable salt thereof is administered as one 40 mg tablet. In another embodiment, the amount of the compound of formula I or compound 1, or a pharmaceutically acceptable salt thereof is administered as one 20 mg tablet. In each of these embodiments, the amount of atezolizumab administered is 1200 mg, which is administered intravenously (IV) as an infusion.

In these and other embodiments, the compound of formula I or compound 1, or a pharmaceutically acceptable salt thereof is administered orally once daily as its free base or as the malate salt as a capsule or tablet. In a further embodiment, compound 1 is administered as the (L)-malate salt (also referred to as the S-malate salt), or the (D)-malate salt (also referred to as the R-malate salt). In a further embodiment:

up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In these and other embodiments, up to and including 1,200 mg of atezolizumab is administered once every three weeks (q3wk) in combination with Compound 1 which is administered orally once daily with fasting as its free base or as a malate salt ((L)-malate salt (also referred to as the S-malate salt), or the (D)-malate salt (also referred to as the R-malate salt)) as a capsule or tablet. In a further embodiment:

up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In these and other embodiments, up to and including 1,100 mg of atezolizumab is administered once every three weeks (q3wk) in combination with Compound 1 which is administered orally once daily with fasting as its free base or as a malate salt ((L)-malate salt (also referred to as the S-malate salt), or the (D)-malate salt (also referred to as the R-malate salt)) as a capsule or tablet. In a further embodiment:

up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;

up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In these and other embodiments, up to and including 1,000 mg of atezolizumab is administered once every three weeks (q3wk) in combination with Compound 1 which is administered orally once daily with fasting as its free base or as a malate salt ((L)-malate salt (also referred to as the S-malate salt), or the (D)-malate salt (also referred to as the R-malate salt)) as a capsule or tablet containing:
up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In these and other embodiments, up to and including 900 mg of atezolizumab is administered once every three weeks (q3wk) in combination with Compound 1 which is administered orally once daily with fasting as its free base or as a malate salt ((L)-malate salt (also referred to as the S-malate salt), or the (D)-malate salt (also referred to as the R-malate salt)) as a capsule or tablet containing:
up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In other embodiments, 1,500 mg, or 1,400 mg, or 1,300 mg, or 1,200 mg, or 1,100 mg, or 1,000 mg, 900 mg, or 800 mg, or 700 mg, or 600 mg of atezolizumab is administered once every three weeks (q3wk) in combination with Compound 1 or a pharmaceutically acceptable salt thereof as a tablet or capsule formulation containing 60, 40, or 20 mg of Compound 1 which is administered orally once daily with fasting as its free base or as a malate salt ((L)-malate salt (also referred to as the S-malate salt), or the (D)-malate salt (also referred to as the R-malate salt)).

In other embodiments, 1,300 mg of atezolizumab is administered once every three weeks (q3wk) in combination with Compound 1 as a tablet or capsule formulation containing 60, 40, or 20 mg of Compound 1, which is administered orally once daily with fasting as its free base or as a malate salt ((L)-malate salt (also referred to as the S-malate salt) or the (D)-malate salt (also referred to as the R-malate salt)).

In other embodiments, 1,200 mg atezolizumab is administered once every three weeks (q3wk) in combination with Compound 1 as a tablet or capsule formulation containing 60, 40, or 20 mg of Compound 1, which is administered orally once daily with fasting as its free base or as a malate salt ((L)-malate salt (also referred to as the S-malate salt), or the (D)-malate salt (also referred to as the R-malate salt)).

In other embodiments, 1,100 mg of atezolizumab is administered once every three weeks (q3wk) in combination with Compound 1 as a tablet or capsule formulation containing 60, 40, or 20 mg of Compound 1, which is administered orally once daily with fasting as its free base or as a malate salt ((L)-malate salt (also referred to as the S-malate salt), or the (D)-malate salt (also referred to as the R-malate salt)).

In another embodiment, the treatment comprises administering 1,300 mg, or 1,200 mg, or 1,100 mg of atezolizumab once every three weeks intravenously as an IV infusion in combination with cabozantinib (S)-malate, which is administered orally, once daily with fasting as a tablet comprising cabozantinib(S)-malate, microcrystalline cellulose, anhydrous lactose, hydroxypropyl cellulose, croscarmellose sodium, colloidal silicon dioxide magnesium stearate, and film coating comprising hypromellose, titanium dioxide, triacetin, and iron oxide yellow.

In a further embodiment, the cabozantinib(S)-malate is administered as a tablet formulation comprising approximately:
- 30-32 percent by weight of cabozantinib, (S)-malate salt;
- 38-40 percent by weight of microcrystalline cellulose;
- 18-22 percent by weight of lactose;
- 2-4 percent by weight of hydroxypropyl cellulose;
- 4-8 percent by weight of croscarmellose sodium;
- 0.2-0.6 percent by weight of colloidal silicon dioxide;
- 0.5-1 percent by weight of magnesium stearate; and further comprising:
- a film coating material comprising hypromellose, titanium dioxide, triacetin, and iron oxide yellow.

In a further embodiment, the cabozantinib(S)-malate is administered as a tablet formulation comprising approximately (% w/w):
- 31-32 percent by weight of cabozantinib, (S)-malate salt;
- 39-40 percent by weight of microcrystalline cellulose;
- 19-20 percent by weight of lactose;
- 2.5-3.5 percent by weight of hydroxypropyl cellulose;
- 5.5-6.5 percent by weight of croscarmellose sodium;
- 0.25-0.35 percent by weight of colloidal silicon dioxide;
- 0.7-0.8 percent by weight of magnesium stearate; and further comprising:
- 3.9-4.1 percent by weight of a film coating material comprising hypromellose, titanium dioxide, triacetin, and iron oxide yellow.

In a further embodiment, the cabozantinib(S)-malate is administered as a tablet formulation containing 20, 40, or 60 mg of cabozantinib orally once daily with fasting.

In a further embodiment, the cabozantinib(S)-malate is administered as a tablet formulation selected from the group consisting of:

| Ingredient | Theoretical Quantity (mg/unit dose) | | |
|---|---|---|---|
| | 20-mg Tablet | 40-mg Tablet | 60-mg Tablet |
| Cabozantinib (S)-malate | 25.34 | 50.69 | 76.03 |
| Microcrystalline Cellulose, PH-102 | 31.08 | 62.16 | 93.24 |
| Lactose Anhydrous, 60M | 15.54 | 31.07 | 46.61 |
| Hydroxypropyl Cellulose, EXF | 2.400 | 4.800 | 7.200 |
| Croscarmellose Sodium | 4.800 | 9.600 | 14.40 |
| Colloidal Silicon Dioxide | 0.2400 | 0.4800 | 0.7200 |
| Magnesium Stearate (Non-Bovine) | 0.6000 | 1.200 | 1.800 |
| Opadry ® Yellow (03K92254) | 3.200 | 6.400 | 9.600 |
| Total tablet weight | 83.20 | 166.4 | 249.6 |

In a further embodiment, the cabozantinib (S)-malate is administered orally once daily.

In a further embodiment, the amount of cabozantinib(S)-malate that is administered orally once daily is 60 mg.

In a farther embodiment, the amount of cabozantinib (S)-malate that is administered orally once daily is 40 mg.

In a further embodiment, the amount of cabozantinib(S)-malate that is administered orally once daily is 20 mg.

In a further embodiment, the cabozantinib (R)-malate is administered orally once daily.

In a further embodiment, the amount of cabozantinib (R)-malate that is administered orally once daily is 60 mg.

In a further embodiment, the amount of cabozantinib (R)-malate that is administered orally once daily is 40 mg.

In a further embodiment, the amount of cabozantinib (R)-malate that is administered orally once daily is 20 mg.

In another embodiment, compound 1 is administered orally as its free base or a malate salt ((L)-malate salt (also referred to as the S-malate salt), or the (D)-malate salt (also referred to as the R-malate salt)) once daily as a tablet as provided in the following table.

| Ingredient | (% w/w) |
|---|---|
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, compound 1 is administered orally as its free base or a malate salt ((L)-malate salt (also referred to as the S-malate salt), or the (D)-malate salt (also referred to as the R-malate salt)) once daily as a tablet as provided in the following table.

| Ingredient | Theoretical Quantity (mg/unit dose) |
|---|---|
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, compound 1 is administered orally as its free base or a malate salt ((L)-malate salt (also referred to as the S-malate salt), or the (D)-malate salt (also referred to as the R-malate salt)) once daily as a tablet as provided in the following table.

| Ingredient | Function | % w/w |
|---|---|---|
| Cabozantinib Drug Substance (25% drug load as free base) | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disintegrant | 6.0 |
| Colloidal Silicon Dioxide, | Glidant | 0.3 |
| Magnesium Stearate | Lubricant | 0.75 |

-continued

| Ingredient | Function | % w/w |
|---|---|---|
| Opadry Yellow Film Coating which includes: | | |
| HPMC 2910/Hypromellose 6 cp<br>Titanium dioxide<br>Triacetin<br>Iron Oxide Yellow | Film Coating | 4.00 |

In some embodiments, atezolizumab is administered as an infusion intravenously (IV) containing 1,200 mg of the fully humanized IgG1 isotype monoclonal antibody. The dosage of atezolizumab used as part of the combination treatment with a compound of formula I or compound 1, or a pharmaceutically acceptable salt thereof, for example as the malate salt, for example, the (L)-malate salt (also referred to as the S-malate salt), or the (D)-malate salt (also referred to as the R-malate salt), is 1,200 mg/20 mL (60 mg/mL) as a single dose vial which may be diluted with 0.9% Sodium Chloride injection only diluent, and mixed gently by gentle inversion and infused into the patient in need thereof over 60 minutes or 30 minutes.

Any of the tablet formulations provided above can be adjusted according to the dose of compound 1 or a pharmaceutically acceptable salt thereof desired. Thus, the amount of each of the formulation ingredients can be proportionally adjusted to provide a tablet formulation containing various amounts of compound 1 or a pharmaceutically acceptable salt thereof as provided in the previous paragraphs. In another embodiment, the formulations can contain 20, 40, 60, or 80 mg of compound 1 or a pharmaceutically acceptable salt thereof.

EMBODIMENTS

The invention is further defined by the following non-limiting embodiments.

Embodiment 1. A method of treating locally advanced or metastatic solid tumors, comprising administering a patient in need of such treatment a compound of formula I:

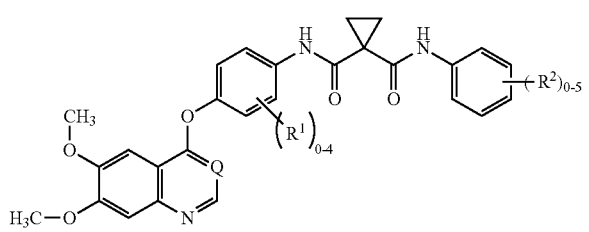

Formula I or a pharmaceutically acceptable salt thereof or a pharmaceutical composition comprising the compound of formula I or the pharmaceutically acceptable salt thereof, and a pharmaceutically acceptable carrier, wherein:

$R^1$ is halo;
$R^2$ is halo; and
Q is CH or N;

In combination with atezolizumab.

Embodiment 2. The method of embodiment 1, wherein the compound of formula I is compound 1, or a pharmaceutically acceptable salt thereof.

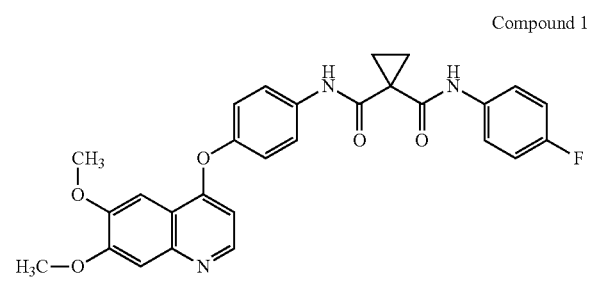 [SMILES: COc1cc2nccc(Oc3ccc(NC(=O)C4(C(=O)Nc5ccc(F)cc5)CC4)cc3)c2cc1OC]

Compound 1

Embodiment 3. The method of embodiment 2, wherein compound 1 is administered as the L-malate salt.

Embodiment 4. The method of embodiment 2, wherein compound 1 is administered as the S-malate salt.

Embodiment 5. The method of embodiments 2-4 wherein atezolizumab is administered intravenously (IV).

Embodiment 6. The method of embodiments 1-5, wherein the locally advanced or metastatic solid tumors is advanced UC, RCC, CRPC, and NSCLC.

Embodiment 7. The method of embodiments 2-6, wherein Compound 1 or a pharmaceutically acceptable salt thereof and atezolizumab are administered concurrently or sequentially.

Embodiment 8. The method of embodiment 6, wherein up to and including 1,200 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg, or compound 1, or a pharmaceutically acceptable salt thereof, once daily with fasting.

Embodiment 9. The method of embodiment 8, wherein up to and including 1,200 mg of atezolizumab is administered to the patient once every three weeks in combination with 60 mg, 40 mg, or 20 mg of compound 1, or a pharmaceutically acceptable salt thereof once daily with fasting.

Embodiment 10. The method of embodiment 6, wherein up to and including 1,100 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof once daily with fasting.

Embodiment 11. The method of embodiment 10, wherein up to and including 1,100 mg of atezolizumab is administered to the patient once every three weeks in combination with 60 mg, 40 mg, or 20 mg of compound 1, or a pharmaceutically acceptable salt thereof once daily with fasting.

Embodiment 12. The method of embodiment 6, wherein up to and including 1,000 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof once daily with fasting.

Embodiment 13. The method of embodiment 12, wherein up to and including 1,000 mg of atezolizumab is administered to the patient once every three weeks in combination with 60 mg, 40 mg, or 20 mg of compound 1, or a pharmaceutically acceptable salt thereof once daily with fasting.

Embodiment 14. The method of embodiment 6, wherein up to and including 900 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof once daily with fasting.

Embodiment 15. The method of embodiment 14, wherein up to and including 900 mg of atezolizumab is administered to the patient once every three weeks in combination with 60 mg, 40 mg, or 20 mg of compound 1, or a pharmaceutically acceptable salt thereof once daily with fasting.

Embodiment 16. The method of embodiments 8-15, wherein Compound 1 or a pharmaceutically acceptable salt thereof and atezolizumab are administered concurrently or sequentially.

Embodiment 17. The method of embodiments 7-16, wherein the atezolizumab is administered intravenously via infusion over 60 minutes or 30 minutes.

Embodiment 18. The method of embodiments 1-17, wherein a complete serological response is observed in patients being treated with the combination.

Embodiment 19. The method of embodiments 1-17, wherein a serological partial response is observed in patients being treated with the combination.

Embodiment 20. The method of embodiments 1-17, wherein stable disease is observed in patients being treated with the combination.

Preparation of Compound 1

Preparation of 1-(4-Fluorophenylcarbamoyl)cyclopropanecarboxylic acid (Compound A-1)

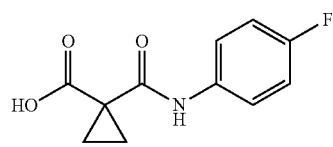

The stating 1,1-cyclopropanedicarboxylic acid was treated with thionyl chloride (1.05 equivalents) in approximately 8 volumes of isopropyl acetate at 25° C. for 5 hours. The resulting mixture was then treated with a solution of 4-fluoroaniline (1.1 equivalents) and triethylamine (1.1 equivalents) in isopropyl acetate (2 volumes) over 1 hour. The product slurry was quenched with 5N NaOH solution (5 volumes), and the aqueous phase was discarded. The organic phase was extracted with 0.5N NaOH solution (10 volumes), and the basic extract was washed with heptane (5 volumes) and subsequently acidified with 30% HCl solution to give a slurry. Compound A-1 was isolated by filtration.

Compound A-1 was prepared on a 1.00 kg scale using 1,1-cyclopropanedicarboxylic acid as the limiting reagent to furnish 1.32 kg of Compound A-1 (77% isolated yield; 84% mass balance) with 99.92% purity (HPLC) and 100.3% assay.

Preparation of N-(4-{[6,7-bis(methyloxy)quinolin-4-yl]oxy}phenyl)-N'-(4-fluorophenyl)cyclopropane-1,1-dicarboxamide (Compound 1) and the (L)-malate salt Thereof A synthetic route that can be used for the preparation of N-(4-{([6,7-bis(methyloxy)quinolin-4-yl]oxy}phenyl)-N'-(4-fluorophenyl)cyclopropane-1,1-dicarboxamide and the (L)-malate salt thereof is depicted in Scheme 1.

Scheme 1
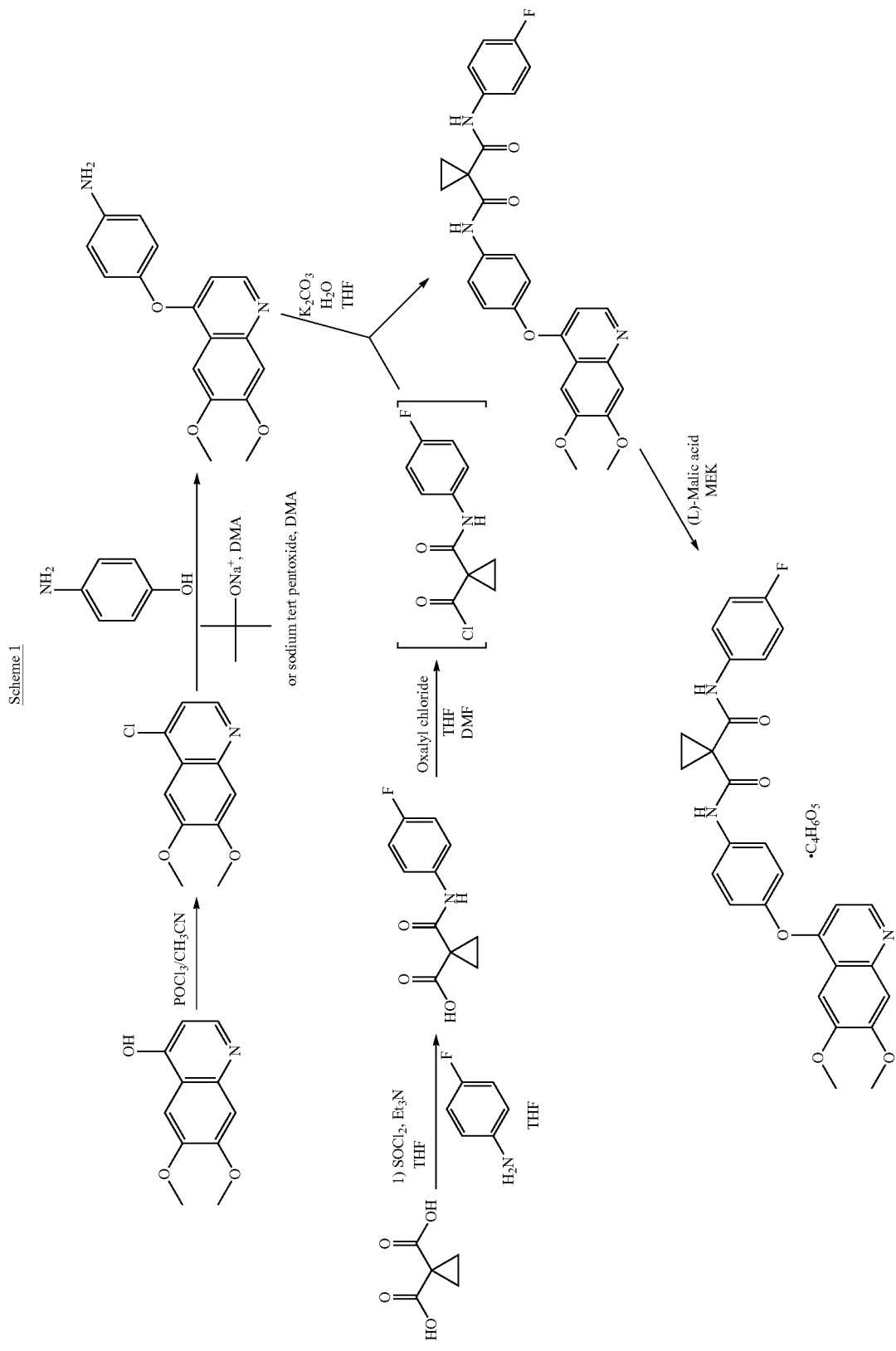

Another synthetic route that can be used for the preparation of N-(4-{[6,7-bis(methyloxy)quinolin-4-yl]oxy}phenyl)-N'-(4-fluorophenyl)cyclopropane-1,4-dicarboxamide and the (L)-malate salt thereof is depicted in Scheme 2.

than 3% of the starting material remained, as measured by in-process high-performance liquid chromatography [HPLC] analysis. The reaction mixture was cooled to approximately 2 to 7° C. and then quenched into a chilled solution of dichloromethane (DCM, 482.8 kg), 26% NH$_4$OH

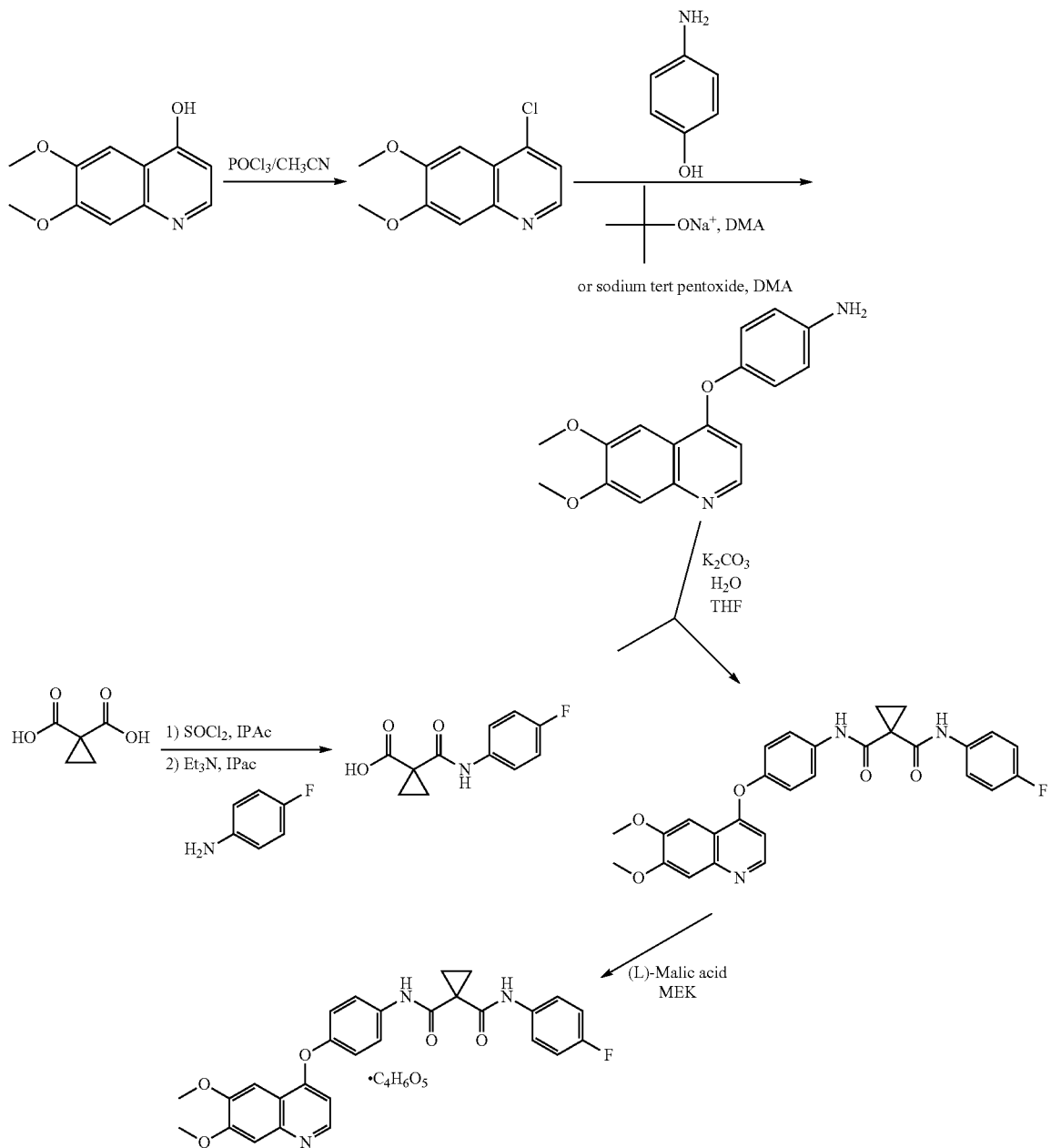

Scheme 2

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less (251.3 kg), and water (900 L). The resulting mixture was warmed to approximately 20 to 25° C., and phases were separated. The organic phase was filtered through a bed of AW hyflo super-cell NF (Celite; 5.4 kg), and the filter bed was washed with DCM (118.9 kg). The combined organic phase was washed with brine (282.9 kg) and mixed with water (120 L). The phases were separated, and the organic phase was concentrated by vacuum distillation with the removal of solvent (approximately 95 L residual volume).

DCM (686.5 kg) was charged to the reactor containing organic phase and concentrated by vacuum distillation with the removal of solvent (approximately 90 L residual volume). Methyl t-butyl ether (MTBE, 226.0 kg) was then charged, and the temperature of the mixture was adjusted to −20 to −25° C. and held for 2.5 hours resulting in solid precipitate, which was then filtered, washed with n-heptane (92.0 kg), and dried on a filter at approximately 25° C. under nitrogen to afford the title compound (35.6 kg).

Preparation of 4-(6, 7-Diethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20-25° C. This mixture was then heated to 100–105° C. for approximately 13 hours. After the reaction was deemed complete as determined using in-process HPLC analysis (less than 2% starting material remaining), the reactor contents were cooled at 15 to 20° C., and water (pre-cooled, 2 to 7° C., 587 L) was charged at a rate to maintain 15 to 30° C. temperature. The resulting solid precipitate was filtered, washed with a mixture of water (47 L) and DMA (89.1 kg), and finally washed with water (214 L). The filter cake was then dried at approximately 25° C. on filter to yield crude 4-(6, 7-dimethoxy-quinoline-4-yloxy)-phenylamine (59.4 kg wet, 41.6 kg dry calculated based on LOD). Crude 4-(6, 7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour, then cooled to 0 to 5° C., and aged for approximately 1 hour, after which time the solid was filtered, washed with THF (147.6 kg), and dried on a filter under vacuum at approximately 25° C. to yield 4-(6,7-dimethoxy-quinoline-4-yloxy)-phenylamine (34.0 kg).

Alternative Preparation of 4-(6, 7-Dimethoxy-quinoline-4-yloxy)-phenylamine 4-chloro-6,7-dimethoxyquinoline (34.8 kg), 4-Aminophenol (30.8 kg), and sodium tert pentoxide (1.8 equivalents) 88.7 kg, 35 weight percent in THF) were charged to a reactor, followed by NN-dimethylacetamide (DMA, 293.3 kg). This mixture was then heated to 105 to 115° C. for approximately 9 hours. After the reaction was deemed complete as determined using in-process HPLC analysis (less than 2% starting material remaining), the reactor contents were cooled at 15 to 25° C., and water (315 kg) was added over a two hour period while maintaining the temperature between 20 and 30° C. The reaction mixture was then agitated for an additional hour at 20 to 25° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used, and the reaction temperature was increased from 110 to 120° C. In addition, the cool down temperature was increased to 35 to 40° C., and the starting temperature of the water addition was adjusted to 35 to 40° C., with an allowed exotherm to 45° C.

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl chloride A reactor was charged with 1-fluoro-phenylcarbamoyl)-cyclopropanecarboxylic acid (35 kg), DMF (344 g), and THF (175 kg). The reaction mixture was adjusted to 12 to 17° C., and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by THF (412.9 kg). To the reaction mixture was charged a solution of $K_2CO_3$ (48.3 kg) in water (169 kg). The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped, and the phases of the mixture were allowed to separate. The lower aqueous phase was removed and discarded. To the remaining upper organic phase was added water (804 kg). The reaction was left stirring at 15 to 25° C. for a minimum of 16 hours.

The product precipitated. The product was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30 to 35° C. for approximately 30 minutes. Water (456 kg) was then added to the solution, as well as SDAG-1 ethanol (20 kg, ethanol denatured with methanol over two hours). The mixture was agitated at 15 to 25° C. for at least 16 hours. The product was filtered and washed with a mixture of water (143 kg and 126.7 kg THF (143 kg) in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, cabozantinib (L) malate salt Cyclopropane-1,1-dicarboxylicacid [4-(6,7-dimethoxy-quinoline-4-yloxy)-phenyl]-amide (4-fluoro-phenyl)-amide (13.3 kg), L-malic acid (4.96 kg), methyl ethyl ketone (MEK; 188.6 kg) and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of cyclopropane-1,1-dicarboxylic acid [4-(6,7-dimethoxy-quinoline-4-yloxy)-phenyl]-amide (4-fluoro-phenyl)-amide (13.3 kg), L-Malic acid (4.96 kg), MEK (198.6 kg), and water (37.2 kg). The combined filtrate was azeotropically dried at atmospheric pressure using MEK (1133.2 kg)(approximate residual volume 711 L; KF<0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylicacid [4-(6,7-dimethoxy-quinoline-4-yloxy)-phenyl]-amide (4-fluoro-phenyl)-imide (47.9 kg), L-malic acid (17.2 kg), methyl ethyl ketone (658.2 kg), and water (129.1 kg) were charged to a reactor, and the mixture was heated 50 to 55° C. for approximately 1 to 3 hours and then at 55 to 60° C. for an additional 4 to 5 hours. The mixture was clarified by filtration through a 1 μm cartridge. The reactor temperature was adjusted to 20 to 25° C. and vacuum distilled with a vacuum at 150 to 200 mm Hg with a maximum jacket temperature of 55° C. to the volume range of 558 to 731 L.

The vacuum distillation was performed two more times with the charge of 380 kg and 380.2 kg methyl ethyl ketone, respectively. After the third distillation, the volume of the batch was adjusted to 18 v/w of Cyclopropane-1, 1-dicarboxylic acid [4-(6,7-dimethoxy-1-quinoline-4-yloxy)-phenyl]-amide (4-fluoro-phenyl)-amide by charging methyl ethyl ketone (159.9 kg) to give a total volume of 880 L. An additional vacuum distillation was carried out by adjusting methyl ethyl ketone (245.7 kg). The reaction mixture was left with moderate agitation at 20 to 25° C. for at least 24 hours. The product was filtered and washed with methyl ethyl ketone (415.1 kg) in three portions. The product was dried under a vacuum with the jacket temperature set point at 45° C.

In an alternative procedure, the order of addition was changes so that a solution of L-malic acid (17.7 kg) dissolved in water (129.9 kg) was added to Cyclopropane-1, 1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Cabozantinib (XL184) is a potent inhibitor of multiple receptor tyrosine kinases (RTKs) known to play important roles in tumor cell proliferation and/or tumor neovascularization including MET, vascular endothelial growth factor receptor (VEGFR), AXL, and RET. Increased expression of MET and AXL has been implicated in the development of resistance to VEGFR inhibitors in preclinical models of several cancers (Shojaei et al 2010, Zhou et al 2015, Sennino et al 2012, Ciamporcero et al 2015). In addition, targets of cabozantinib are implicated in promoting tumor-immune suppression including TYRO3, MER, and AXL (tumor-assisted macrophage [TAM] family kinases). Cabozantinib capsules (140 mg) are approved for the treatment of progressive, metastatic medullary thyroid cancer (MTC) in the United States and the European Union (Elisei et al 2013; Cometriq™ US PI and EMA SmPC).

Cabozantinib tablets (60 mg) are approved in the United States and the European Union for the treatment of advanced RCC after prior anti-angiogenic/VEGFR-targeted therapy (Choueiri et al 2016, Cabometyx™ US PI and EMA SmPC). Cabozantinib is also listed as recommended therapy in patients with untreated RCC of intermediate- and poor-risk (NCCN 2017), and is currently under review by regulatory agencies in the US and the European Union based on statistically improved progression-free survival (PFS) compared with sunitinib (Choueiri et al [J Clin Oncol] 2017, Choueiri et al [Ann Oncol] 2017).

Cabozantinib (60 mg) has also demonstrated clinical activity in a Phase 2 study of subjects with relapsed or refractory metastatic UC (Apolo et al [J Clin Oncol]2016) and in a Phase 3 trial of subjects with CRPC after prior docetaxel and antiandrogen-receptor therapy (Smith et al 2016). Although the primary endpoint of overall survival (OS) in the Phase 3 CRPC study was not met, treatment with cabozantinib resulted in a significant improvement of PFS compared with prednisone and other clinical benefits and biomarker changes such as improvement in bone scan response (BSR) and bone turn-over markers, decrease in incidence of skeletal-related events, as well as reduction of circulating tumor cells. Encouraging clinical activity of cabozantinib has also been observed in several early phase clinical trials in advanced NSCLC (Drilon et al 2016, Neal et al 2016, Hellerstedt et al 2012, Wakelee et al 2017; Schöffski et al. 2017). The objective response rate (ORR) in heavily pre-pretreated unselected NSCLC was approximately 10%, and 28% in RET-rearranged NSCLC. Median PFS and median OS were comparable to standard of care chemotherapy in this patient population (Alimta [pemetrexed] US PI, Taxotere [docetaxel] US PI).

Preclinical studies (Kwilas et al 2014, Song et al 2015, Lu et al 2017) and clinical observations on circulating immune suppressive cells and immune effector cells (Apolo et al 2014) suggest that cabozantinib promotes an immune-permissive environment through inhibition of immune-modulatory targets on immune cells. This might present an opportunity for synergistic effects from combination treatment with ICIs. In an ongoing Phase 1 study in genitourinary (GU) cancers, cabozantinib is being evaluated in combination with the ICI nivolumab, a monoclonal antibody to PD-1. The dose escalation stage has been completed and no dose-limiting toxicities (DLTs) were reported. The recommended dose for phase 2 (R2PD) was determined to be 40 mg daily (qd) for cabozantinib in combination with 3 mg/kg of nivolumab (intravenous [IV], every other week [q2w]). At the data cutoff, the ORR was 39% among a variety of different GU tumor types. Among subjects with UC, a 44% ORR was reported, and among nine enrolled CRPC subjects 67% achieved stable disease and one subject had a partial response (Nadal et al 2017). The combination of cabozantinib with ICIs may also provide a strategy to overcome resistance to ICI therapy. This is based on a recent observation in a clinical trial where re-treatment with an ICI in combination with the VEGFR-TKI sitravatinib that has a target profile similar to cabozantinib, resulted in reversal of prior ICI resistance in NSCLC patients (Leal et al 2017). These results suggest that combining ICIs with cabozantinib may result in a tumor micro-environment that is conducive to re-sensitization to ICI therapy after prior progression on a ICI.

The Dose Escalation Stage of the current study (XL184-021) has been initiated and is ongoing in subjects with advanced UC or RCC. In Cohort 1 of the Dose Escalation Stage, no DLTs were identified for the combination of 40 mg cabozantinib qd and 1200 mg atezolizumab q3w. Cohort 2 is currently evaluating the combination of 60 mg cabozantinib qd and 1200 mg atezolizumab q3w. After a recommended cabozantinib dose for the combination therapy with a standard dose of atezolizumab has been established, the Expansion Stage with tumor-specific cohorts in UC, RCC, CRPC, and NSCLC will be enrolled in order to further evaluate the safety and efficacy of this combination in these tumor indications.

Example 1. Summary of an Experimental Clinical Trial Studying the Combination of Cabozantinib (XL184) with Atezolizumab in Subjects with Locally Advanced or Metastatic Solid Tumors Such as Advanced UC, RCC, CRPC and NSCLC Rationale Multi-targeted tyrosine kinase inhibitors (TKIs) and immune checkpoint inhibitors (ICIs) represent two systemic modalities that have been instrumental in the recent advancements of anticancer treatment over the past several years. Both classes of therapies have demonstrated broad clinical effects leading to new approved treatment options across multiple tumor types including renal cell carcinoma (RCC), urothelial carcinoma (UC), melanoma, non-small-cell lung cancer (NSCLC), and others. The success of these therapy types as single agents with distinct mechanisms of action has naturally led to interest in evaluating combinations of TKIs with ICIs in search of further, possibly synergistic, anticancer clinical effects.

Atezolizumab is a humanized immunoglobulin (Ig) G1 monoclonal antibody that targets programmed death receptor 1 ligand (PD-L1) and inhibits the interaction between PD-L1 and its receptors, programmed death receptor 1 (PD-1) and B7-1 (also known as CD80), both of which function as inhibitory receptors expressed on T cells. It is approved in the United States and the European Union for the treatment of patients with localized advanced or metastatic UC after prior platinum-containing chemotherapy or who we considered cisplatin-ineligible (Rosenberg et al 2016, Loriot et al 2016). Atezolizumab is also approved for patients with locally advanced or metastatic NSCLC after prior chemotherapy (Fehrenbacher et al 2016; Tecentriq US Prescribing Information; EMA SmPC). Patients with epidermal growth factor receptor (EGFR) activating mutations or anaplastic lymphoma kinase (ALK)-positive tumour mutations should also have received targeted therapy before receiving atezolizumab. Further, atezolizumab has demonstrated clinical activity in treatment-naïve and chemotherapy experienced PD-L1 positive advanced-stage NSCLC (Peters et al 2017) and in advanced RCC as single agent (McDermott et al 2016) and in combination with a vascular endothelial growth factor (VEGF)-targeting antibody, bevacizumab (Sznol et al 2015). In addition, atezolizumab is currently being evaluated in combination with enzalutamide in metastatic castration-recurrent prostate cancer (CRPC; NCT03016312). Resistance to enzalutamide in CRPC has been associated with upregulated PD-L1 expression (Bishop et al 2015) and early clinical data suggest that ICI therapy may provide clinical benefits in CRPC patients following progression on enzalutamide (Graff et al 2016).

Cabozantinib (XL184) is a potent inhibitor of multiple receptor tyrosine kinases (RTKs) known to play important roles in tumor cell proliferation and/or tumor neovascularization including MET, vascular endothelial growth factor receptor (VEGFR), AXL, and RET. Increased expression of MET and AXL has been implicated in the development of resistance to VEGFR inhibitors in preclinical models of several cancers (Shojaei et al 2010, Zhou et al 2015, Sennino et al 2012, Ciamporcero et al 2015). In addition, targets of cabozantinib are implicated in promoting tumor-immune suppression including TYRO3, MER, and AXL (tumor-assisted macrophage [TAM] family kinases). Cabozantinib capsules (140 mg) are approved for the treatment of progressive, metastatic medullary thyroid cancer (MTC) in the United States and the European Union (Elisei at al 2013; Cometriq™ US PI and EMA SmPC).

Cabozantinib tablets (60 mg) are approved in the United States and the European Union for the treatment of advanced RCC after prior anti-angiogenic/VEGFR-targeted therapy (Choueiri et al 2016, Cabometyx™ US PI and EMA SmPC). Cabozantinib is also listed as recommended therapy in patients with untreated RCC of intermediate- and poor-risk (NCCN 2017), and is currently under review by regulatory agencies in the US and the European Union based on statistically improved progression-free survival (PFS) compared with sunitinib (Choueiri et al [J Clin Oncol]2017, Choueiri et al [Ann Oncol] 2017).

Cabozantinib (60 mg) has also demonstrated clinical activity in a Phase 2 study of subjects with relapsed or refractory metastatic UC (Apolo et al [J Clin Oncol]2016) and in a Phase 3 trial of subjects with CRPC after prior docetaxel and antiandrogen-receptor therapy (Smith et al 2016). Although the primary endpoint of overall survival (OS) in the Phase 3 CRPC study was not met, treatment with cabozantinib resulted in a significant improvement of PFS compared with prednisone and other clinical benefits and biomarker changes such as improvement in bone scan response (BSR) and bone turn-over markers, decrease in incidence of skeletal-related events, as well as reduction of circulating tumor cells. Encouraging clinical activity of cabozantinib has also been observed in several early phase clinical trials in advanced NSCLC (Drilon et al 2016, Neal et al 2016, Hellerstedt et al 2012, Wakelee et al 2017; Schöffski et al. 2017). The objective response rate (ORR) in heavily pre-pretreated unselected NSCLC was approximately 10%, and 28% in RET-rearranged NSCLC. Median PFS and median OS were comparable to standard of care chemotherapy in this patient population (Alimta [pemetrexed] US PI, Taxotere [docetaxel] US PI).

Preclinical studies (Kwilas at al 2014, Song et al 2015, Lu et al 2017) and clinical observations on circulating immune suppressive cells and immune effector cells (Apolo et al 2014) suggest that cabozantinib promotes an immune-permissive environment through inhibition of immune-modulatory targets on immune cells. This might present an opportunity for synergistic effects from combination treatment with ICIs. In an ongoing Phase 1 study in genitourinary (GU) cancers, cabozantinib is being evaluated in combination with the ICI nivolumab, a monoclonal antibody to PD-1. The dose escalation stage has been completed and no dose-limiting toxicities (DLTs) were reported. The recommended dose for phase 2 (R2PD) was determined to be 40 mg daily (qd) for cabozantinib in combination with 3 mg/kg of nivolumab (intravenous [IV], every other week [q2w]). At the data cutoff, the ORR was 39% among a variety of different GU tumor types. Among subjects with UC, a 44% ORR was reported, and among nine enrolled CRPC subjects 67% achieved stable disease and one subject had a partial response (Nadal et al 2017). The combination of cabozantinib with ICIs may also provide a strategy to overcome resistance to ICI therapy. This is based on a recent observation in a clinical trial where re-treatment with an ICI in combination with the VEGFR-TKI sitravatinib that has a target profile similar to cabozantinib, resulted in reversal of prior ICI resistance in NSCLC patients (Leal et al 2017). These results suggest that combining ICIs with cabozantinib may result in a tumor micro-environment that is conducive to re-sensitization to ICI therapy after prior progression on a ICI.

The Dose Escalation Stage of the current study (XL184-021) has been initiated and is ongoing in subjects with advanced UC or RCC. In Cohort 1 of the Dose Escalation Stage, no DLTs were identified for the combination of 40 mg cabozantinib qd and 1200 mg atezolizumab q3w. Cohort 2 is currently evaluating the combination of 60 mg cabozantinib qd and 1200 mg atezolizumab q3w. After a recommended cabozantinib dose for the combination therapy with a standard dose of atezolizumab has been established, the Expansion Stage with tumor-specific cohorts in UC, RCC, CRPC, and NSCLC will be enrolled in order to further evaluate the safety and efficacy of this combination in these tumor indications.

Objectives

Dose-Escalation Stage:

The primary objective is as follows:

To determine the maximum tolerated dose (MTD) and/or recommended dose and schedule for the subsequent Expansion Stage of daily oral administration of cabozantinib in subjects with solid tumors when taken in combination with atezolizumab.

The secondary objective is as follows:

To evaluate the plasma pharmacokinetics (PK) of daily oral administration of cabozantinib in subjects with solid tumors when given in combination with atezolizumab.

To assess safety for the combination therapy through the evaluation of incidence and severity of nonserious adverse events (AEs) and serious adverse events (SAEs), including immune-related adverse events (irAEs) and adverse events of special interest (AESIs).

The exploratory objective is as follows:

Correlation of immune cell, tumor cell, and blood biomarker analyses with clinical outcome Expansion Stage:

The primary objective and endpoint is as follows:

To evaluate preliminary efficacy by estimating the ORR assessed by the Investigator per Response Evaluation Criteria in Solid Tumors (version 1.1)(RECIST 1.1)

The secondary objective is as follows:

To assess safety for the combination therapy through the evaluation of incidence and severity of nonserious AEs and SAEs, including irAEs and AESIs.

The exploratory objectives and endpoints are as follows:

ORR as assessed by the Investigator per modified RECIST for immune response.

Duration of response (DOR) as assessed by the Investigator per RECIST 1.1

Progression-free survival as assessed by the Investigator per RECIST 1.1

Overall Survival

Correlation of immune cell, tumor cell, and blood biomarker analyses with clinical outcome Changes in tumor infiltration and/or histology or other molecular changes as determined from optional tumor biopsy.

To further evaluate the plasma pharmacokinetics (PK) of daily oral administration of cabozantinib in subjects with solid tumors when given in combination with atezolizumab.

For CRPC only: changes in prostate-specific antigen (PSA) and evaluation of mismatch repair (MMR) and microsatellite instability (MSI) status Study Design This is a multicenter, open-label Phase 1b study to assess safety, tolerability, preliminary efficacy, and PK of cabozantinib taken in combination with atezolizumab in subjects with advanced UC, RCC, CRPC, and NSCLC. This study consists of two stages:

Dose Escalation Stage: to determine the schedule and MTD and/or recommended Expansion Stage dose of cabozantinib when taken in combination with a standard dosing regimen of atezolizumab (1200 mg infusion, once every 3 weeks). Three cabozantinib tablet daily dose levels will be considered for evaluation: 20 mg, 40 mg, and 60 mg. Subjects will accrue in escalation cohorts of 3-6 subjects using a "3 plus 3" design and dosing will begin at the 40 mg dose level of cabozantinib. Subjects with either advanced UC or RCC will be eligible for these Dose Escalation cohorts, and cohorts may comprise mixtures of subjects with those tumor types. During this stage the decision to open a new cohort will be made by the Cohort Review Committee (CRC) when all subjects in the current cohort have been followed for at least 21 days following first dose of atezolizumab (defined as the DLT Evaluation Period). All available safety and PK data will be considered in a decision to dose escalate or de-escalate the next cohort or to expand the current cohort. An MTD of cabozantinib will be defined as the highest evaluated dose level at which not more than 1 out of 6 subjects experiences a DLT. The recommended dose and schedule for the Expansion Stage will be determined by the CRC based on DLTs and other relevant safety information.

| Relative Dose Level | Cabozantinib | Atezolizumab |
|---|---|---|
| 2 | 60 mg oral qd | 1200 mg IV q3w |
| 1 | 40 mg oral qd | 1200 mg IV q3w |
| −1 | 20 mg oral qd | 1200 mg IV q3w |

IV, intravenous;
qd, once daily;
q3w, once every three weeks

Dose-limiting toxicity will be determined by the CRC upon review of all available data and is defined as any of the following occurring during the DLT Evaluation Period:

Any related AE that in the opinion of the CRC is of potential clinical significance such that further dose escalation of cabozantinib would expose subjects to unacceptable risk.

Any related ≥Grade 3 AE which is unexpected in severity and/or duration compared with the known safety profiles of cabozantinib and atezolizumab when used as single agents, and that cannot be managed by dose modification (reduction or interruption) and adequate supportive care, and requires permanent discontinuation of cabozantinib and/or atezolizumab.

Inability to take ≥75% of the total planned cabozantinib dose for the DLT Evaluation Period because of a treatment-related AE leading to dose reductions and/or interruptions.

Subjects in the Dose Escalation Stage will receive study treatment on one of two dosing schedules: the Standard Dosing Schedule or the Cabozantinib Run-In Dosing Schedule. The Dose Escalation Stage will be initiated with the Standard Dosing Schedule. The Cabozantinib Run-In Dosing Schedule may be implemented upon request of the CRC if no recommended Expansion Stage dose is identified after the evaluation of the Standard Dosing Schedule.

Standard Dosing Schedule: Initial dose escalation cohorts will receive the combination regimen on a "Standard Dosing Schedule" with the first infusion of atezolizumab given on the same day as the first dose of cabozantinib (on Cycle 1 Day 1 [C1D1]).

Cabozantinib Run-In Dosing Schedule: If review of safety data for all enrolled subjects who received the Standard Dosing Schedule does not yield a recommended dose for the Expansion Stage, the CRC may decide to enroll additional cohorts treated on a "Cabozantinib Run-In Dosing Schedule." Subjects in these cohorts will receive the first infusion of atezolizumab on C2D1, 21 days after their first dose of single-agent cabozantinib (same possible dose levels as described above). The subjects will only be evaluated for DLTs during the 21-day period after receiving the first infusion of atezolizumab (the DLT Evaluation Period). These cohorts would be enrolled according to the "3+3" strategy described above, but the CRC may include additional subjects at one or more dose levels in order to ensure enough subjects reach the DLT Evaluation Period while still receiving the assigned cohort dose (ie, experienced no dose reductions in the Cabozantinib Run-In Dosing Schedule). Administration of the first dose of atezolizumab is not to occur while cabozantinib treatment is interrupted; the start of Cycle 2 is to be delayed until after cabozantinib treatment has resumed, is well-tolerated, and the investigator determines that atezolizumab can be administered safely. Subjects who discontinue cabozantinib treatment during Cycle 1 on the Cabozantinib Run-In Dosing Schedule will not be eligible to receive atezolizumab on study. The purpose of this dosing schedule is to help the CRC assess whether subjects would have improved tolerability to the combination of cabozantinib and atezolizumab if first given the opportunity to optimize their tolerability to cabozantinib alone during a three week run-in period. Thus, the CRC will consider safety data from all Dose Escalation cohorts when determining the recommended Expansion Stage dose and schedule.

Expansion Stage. Once the CRC identifies the recommended dose and schedule of cabozantinib in combination with the standard dose of atezolizumab, the study will enter the Expansion Stage. In this stage, eight expansion cohorts in subjects with advanced UC, RCC, CRPC, and NSCLC will be enrolled to obtain additional efficacy safety, PK, and pharmacodynamic data at the recommended dose and schedule. Only one dose level and dosing schedule will be evaluated in the Expansion Stage (the Standard Dosing Schedule or the Cabozantinib Run-In Dosing Schedule).

The following is an abbreviated description of the Expansion Cohorts 1-8:

| Cohort | Tumor Type (Histology) | Abbreviated Eligibility Description | Initial Cohort Size (n) | Potential Additional Enrollment (n) |
|---|---|---|---|---|
| 1 | RCC (clear cell) | No prior systemic anticancer therapy | 30 | — |
| 2 | UC (transitional cell) | Prior platinum-containing chemotherapy | 30 | — |
| 3 | UC (transitional cell) | Cisplatin-ineligible but no prior systemic anticancer therapy | 30 | — |
| 4 | UC (transitional cell) | Cisplatin-eligible but no prior systemic anticancer therapy | 30 | — |
| 5 | UC (transitional cell) | Prior immune checkpoint inhibitor therapy | 30 | 50 |
| 6 | CRPC (adeno) | Prior enzalutamide and/or abiraterone therapy | 30 | — |
| 7 | NSCLC (non-squamous) | Prior immune checkpoint inhibitor therapy | 30 | 50 |
| 8 | NSCLC (non-squamous) | No prior immune checkpoint inhibitor therapy | 30 | — |
| | Total enrollment | | 240 | 340 |

All Expansion cohorts will initially enroll 30 subjects. Because of the high unmet need of patients who have progressed on prior ICI therapy, the Study Oversight Committee of the study may decide after reviewing data of Expansion Cohorts 5 and 7 to allow for additional enrollment of each 50 subjects to further assess the clinical activity and safety of cabozantinib in combination with atezolizumab following ICI progression. All subjects enrolled in the Expansion Cohort will be following the same schedule of assessments and dosing instructions. For more detail regarding the eligibility of subjects for this study refer to inclusion and exclusion criteria. Rationales for enrollment in each Expansion Cohort are provided in Section 1.3.1.

Treatment Periods for Both Stages:

Each subject's course of treatment will consist of the following periods:

Pre-Treatment Period: Potential subjects will be screened to determine if they meet the required eligibility criteria. Qualifying screening assessments must be performed within 28 days before first dose of study treatment unless otherwise specified.

Treatment Period: Eligible subjects will receive open-label combination treatment. Cabozantinib (20, 40, or 60 mg depending on study stage and dose-escalation cohort) will be orally administered qd. The date of the first dose of cabozantinib will be defined to be C1D1. Atezolizumab (1200 mg infusion) will be administered once every three weeks (−2 days) on Day 1 of each cycle starting on C1D1 for the Standard Dosing Schedule or C2D1 for the Cabozantinib Run-In Dosing Schedule.

Permitted study drug modifications comprise dose reductions (from 60 mg to 40 mg qd, from 40 mg to 20 mg qd, or from 20 mg qd to 20 mg every other day [qod]) or interruptions for cabozantinib and dose delays for atezolizumab.

Subjects will receive study treatment as long as they continue to experience clinical benefit in the opinion of the investigator or until there is unacceptable toxicity or the need for subsequent systemic anticancer treatment. Treatment may continue after radiographic progression as long as the investigator believes that the subject is still receiving clinical benefit from study treatment and that the potential benefit of continuing study treatment outweighs potential risk. Following Sponsor notification, subjects may be allowed to discontinue one component of the study treatment but continue to receive the other.

Post-Treatment Period: The final safety assessment will occur at the post-treatment follow-up visit 30 (+14) days after the date of the decision to discontinue treatment. If a subject is experiencing an SAE, AESI, or Grade 3 or 4 AE or at the time of that visit, the subject will continue to be followed until the AE has resolved, the AE has improved to Grade 2 or lower, or the investigator determines that the event has become stable or irreversible.

Maintenance Phase: When sufficient data have been collected to adequately evaluate all study endpoints, and upon site notification by the Sponsor, subjects remaining on study treatment will enter the study Maintenance Phase. In the Maintenance Phase subjects will continue to receive study treatment until a protocol-defined criterion for discontinuation has been met. Following Sponsor notification, subjects may be allowed to discontinue one component of the study treatment but continue to receive the other.

In the Maintenance Phase, subjects are to undergo periodic safety assessments (including local laboratory tests) and tumor assessments; the nature and frequency of these assessments are to be performed per standard of care if allowed per local regulations. In order to continue to collect important safety information on subjects still enrolled in the study, reporting of SAEs; AEs (including irAEs), whether serious or not, leading to dose modifications or treatment discontinuation; AESIs; and other reportable events (pregnancy and medication errors with sequelae) is to continue per protocol requirements specific to the Maintenance Phase.

Assessments in the Post-Treatment Period (including the post-treatment follow-up visit) are not required for subjects who discontinue study treatment in the Maintenance Phase (such subjects are to be followed per standard of care).

Only data collected prior to implementation of Maintenance Phase will be reported in a clinical study report.

Study Completion by Country or by Site: After sufficient data have been collected to adequately evaluate all study endpoints and upon site notification by the Sponsor, the study will be considered complete at sites and in countries that no longer have active subjects.

Number of Subjects

In the dose escalation stage 9 to 36 subjects may be treated. In the Dose Expansion Stage between approximately 240 and 340 subjects will be treated across eight different tumor cohorts: All Expansion Cohorts will enroll initially each approximately 30 subjects. Enrollment in Cohorts S and 7 may be further expanded by additional 50 subjects to approximately 80 subjects each upon Study Oversight Committee decision confirming that clinically meaningful activity was observed which warrants further evaluation of the safety and efficacy of the combination therapy in these cohorts.

Target Population

To be eligible for the study the subject must meet all of the inclusion and none of the exclusion criteria. The Sponsor will not grant exceptions to these eligibility criteria:

Inclusion Criteria

1. Cytologically or histologically and radiologically confirmed solid tumor that is inoperable locally advanced, metastatic, or recurrent:

Dose-Escalation Stage:

Subjects with UC (including renal pelvis, ureter, urinary bladder, urethra) after prior platinum-based therapy, or Subjects with RCC (clear cell, non-clear cell histology) with or without prior systemic anticancer therapy Expansion Stage:

Expansion Cohort 1: Subjects with RCC with clear cell histology (including those with mixed sarcomatoid component) and without prior systemic anticancer therapy.

Expansion Cohort 2: Subjects with UC with transitional cell histology (including renal pelvis, ureter, urinary bladder, urethra) who have radiographically progressed on or after platinum-containing chemotherapy including subjects who received prior neoadjuvant or adjuvant platinum-containing therapy with disease recurrence <12 months from the end of last therapy.

Expansion Cohort 3: Subjects with UC with transitional cell histology (including renal pelvis, ureter, urinary bladder, urethra) who are ineligible for cisplatin-based chemotherapy and have not received prior systemic anticancer therapy for inoperable locally advanced or metastatic disease.

Ineligible for cisplatin-based chemotherapy is defined by meeting one of the following criteria:

Impaired renal function (glomerular filtration rate [GFR]>30 mL/min/1.73 m2 and <60 mL/min/1.73 m2, hearing loss of ≥25 dB at two contiguous frequencies, or ≥Grade 2 peripheral neuropathy per Common Terminology Criteria for Adverse Events (CTCAE) v4.

Prior neoadjuvant or adjuvant platinum-based chemotherapy is allowed if disease recurrence took place >12 months from end of last therapy.

Expansion Cohort 4: Subjects with UC with transitional cell histology (including renal pelvis, ureter, urinary bladder, urethra) eligible for cisplatin-based chemotherapy and have not received prior systemic anticancer therapy for inoperable locally advanced or metastatic disease.

Prior neoadjuvant or adjuvant platinum-based chemotherapy is allowed if disease recurrence took place >12 months from end of last therapy.

Expansion Cohort 5: Subjects with UC with transitional cell histology (including renal pelvis, ureter, urinary bladder, urethra) who have radiographically progressed on or after one prior immune checkpoint inhibitor (anti-PD-1 or anti-PD-L1) as the most recent therapy for the treatment of inoperable locally advanced or metastatic disease.

Allowed are up to 2 lines of prior systemic anticancer therapy to treat locally advanced or metastatic UC including prior treatment with an anti-CTLA-4 agent.

Excluded are subjects who had a prior combination therapy of an immune checkpoint inhibitor (anti-PD-1 or anti-PD-L1) with a VEGFR-targeting TKI.

Expansion Cohort 6: Subjects with metastatic CRPC (adenocarcinoma of the prostate without neuroendocrine differentiation or small cell features) who have radiographically progressed in soft tissue on or after enzalutamide and/or abiraterone acetate for metastatic disease. (Note: PSA progression or bone progression alone are not allowed to determine eligibility).

Prior chemotherapy is not allowed with the exception of docetaxel given in combination with androgen deprivation therapy (ADT) for progressive castration-naïve disease prior to treatment with enzalutamide and/or abiraterone acetate.

Prior radium Ra 223 dichloride is not allowed.

Subject must have castrate-level testosterone (<50 ng/dL [<2 nM]) following bilateral orchiectomy or by ongoing androgen deprivation therapy with a gonadotropin-releasing hormone (GnRH) analog that was initiated ≥4 weeks prior to first dose of study treatment and must be continued throughout the study.

Expansion Cohort 7: Subjects with Stage IV non-squamous NSCLC who have radiographically progressed on or after treatment with one prior immune checkpoint inhibitor (anti-PD-1 or anti-PD-L1) as the most recent therapy for metastatic disease.

Allowed are up to 2 lines of prior systemic anticancer therapy to treat metastatic NSCLC including prior treatment with an anti-CTLA-4 agent.

Excluded are subjects who had a prior combination therapy of an immune checkpoint inhibitor (anti-PD-1 or anti-PD-1) with a VEGFR-targeting TKI and subjects who have been diagnosed with an EGFR mutation, ALK translocation, ROS1 rearrangement, or BRAF V600E mutation.

Expansion Cohort 8: Subjects with Stage IV non-squamous NSCLC who have not received prior immune checkpoint inhibitor therapy (anti-PD-1 or anti-PD-L1).

One line of prior systemic anticancer therapy to treat metastatic NSCLC is allowed.

Excluded are subjects who have been diagnosed with an EGFR mutation, ALK translocation, ROS1 rearrangement, or BRAF V600E mutation.

2. Measurable disease per RECIST 1.1 as determined by the investigator. Measurable disease must be outside the radiation field if prior radiation therapy was administered.

3. Tumor tissue material available (archival or recent tumor biopsy)

4. Recovery to baseline or ≤Grade 1 CTCAE v4 from toxicities related to any prior treatments, unless AE(s) are clinically nonsignificant and/or stable on supportive therapy.

5. Age eighteen years or older on the day of consent.

6. Eastern Cooperative Oncology Group (ECOG) Performance Status of 0 or 1.

7. Adequate organ and marrow function, based upon meeting all of the following laboratory criteria within 14 days before first dose of study treatment:

Absolute neutrophil count (ANC)≥1500/mm3 (≥1.5 GI/L) without granulocyte colony-stimulating factor support within 2 weeks before screening laboratory sample collection.

White blood cell count ≥2500/mm3 (≥2.5 GI/L).

Platelets ≥100,000/mm3 (≥100 OIL) without transfusion within 2 weeks before screening laboratory sample collection.

Hemoglobin ≥9 g/dL (≥90 g/L) without transfusion within 2 weeks before screening laboratory sample collection.

Alanine aminotransferase (ALT), aspartate aminotransferase (AST), and alkaline phosphatase (ALP)≤3× upper limit of normal (ULN). ALP ≤5☐ ULN with documented bone metastases.

Total bilirubin ≤1.5×ULN (for subjects with Gilbert's disease ≤3☐ ULN).

Serum creatinine ≤2.0×ULN or calculated creatinine clearance ≥30 mL/min (≥0.5 mL/sec) using the Cockcroft-Gault equation (see Table 5-2 for Cockcroft-Gault formula).

Urine protein/creatinine ratio (UPCR) ≤1 mg/mg (≤113.2 mg/mmol) for subjects with RCC, CRPC, or NSCLC; and ≤2 mg/mg (≤226.4 mg/mmol) creatinine for subjects with UC.

8. Capable of understanding and complying with the protocol requirements and must have signed the informed consent document.

9. Sexually active fertile subjects and their partners must agree to use medically accepted methods of contraception (eg, barrier methods, including male condom, female condom, or diaphragm with spermicidal gel) during the course of the study and for S months after the last dose of study treatment.

10. Female subjects of childbearing potential must not be pregnant at screening. Females of childbearing potential are defined as premenopausal females capable of becoming pregnant (ie, females who have had any evidence of menses in the past 12 months, with the exception of those who had prior hysterectomy). However, women who have been amenorrhea for 12 or more months are still considered to be of childbearing potential if the amenorrhea is possibly due to prior chemotherapy, antiestrogens, low body weight, ovarian suppression or other reasons.

Exclusion Criteria

Prior treatment with cabozantinib or ICIs including anti-CTLA-4, anti-PD-1, anti-PD-L1, anti-PD-L2, anti-OX-40, anti-CD137 therapy except for Expansion Cohorts 5 and 7 in which prior anti-PD-1 or anti-PD-L1 therapy is required for eligibility (see Inclusion Criteria 1g and 1i, respectively, for details).

Receipt of any type of small molecule kinase inhibitor (including investigational kinase inhibitor) within 2 weeks before first dose of study treatment.

For CRPC subjects: receipt of flutamide or nilutamide within 4 weeks or bicalutamide within 6 weeks before first dose of study treatment.

4. Receipt of any type of anticancer antibody (including investigational antibody) or systemic chemotherapy within 4 weeks before first dose of study treatment, except in Expansion Cohorts 5 and 7 for which receipt of a PD-1, PD-L1, or CTLA-4 targeting antibody is permitted within 4 weeks before first dose of study treatment.

5. Radiation therapy for bone metastasis within 2 weeks, any other radiation therapy within 4 weeks before first dose of study treatment. Subjects with clinically relevant ongoing complications from prior radiation therapy are not eligible.

6. Known brain metastases or cranial epidural disease unless adequately treated with radiotherapy and/or surgery (including radiosurgery) and stable for at least 4 weeks before first dose of study treatment. Eligible subjects must be neurologically asymptomatic and without corticosteroid treatment at the time of first dose of study treatment.

7. Concomitant anticoagulation with oral anticoagulants (eg, warfarin, direct thrombin and Factor Xa inhibitors) or platelet inhibitors (eg, clopidogrel).

Allowed anticoagulants are the following:

Low-dose aspirin for cardioprotection (per local applicable guidelines) and low-dose low molecular weight heparins (LMWH).

Anticoagulation with therapeutic doses of LMWH in subjects without known brain metastases who are on a stable dose of LMWH for at least 6 weeks before first dose of study treatment, and who have had no clinically significant hemorrhagic complications from the anticoagulation regimen or the tumor.

8. Diagnosis of immunodeficiency or is receiving systemic steroid therapy or any other form of immunosuppressive therapy within 2 weeks prior to first dose of study treatment. Inhaled and topical corticosteroids and mineralocorticoids are allowed.

9. Administration of a live, attenuated vaccine within 30 days before first dose of study treatment.

10. The subject has uncontrolled, significant intercurrent or recent illness including, but not limited to, the following conditions:

a. Cardiovascular Disorders:

Congestive heart failure New York Heart Association Class 3 or 4, unstable angina pectoris, serious cardiac arrhythmias.

Uncontrolled hypertension defined as sustained blood pressure (BP)>150 mm Hg systolic or >100 mm Hg diastolic despite optimal antihypertensive treatment.

Stroke (including transient ischemic attack [TIA]), myocardial infarction (MI), or other ischemic event, or thromboembolic event (eg, deep venous thrombosis [DVT], pulmonary embolism) within 6 months before first dose. Subjects with a diagnosis of DVT within 6 months are allowed if stable, asymptomatic, and treated with LMWH for at least 6 weeks before first dose.

b. Gastrointestinal (01) disorders including those associated with a high risk of perforation or fistula formation:

Tumors invading the GI-tract, active peptic ulcer disease, inflammatory bowel disease, diverticulitis, cholecystitis, symptomatic cholangitis or appendicitis, acute pancreatitis or acute obstruction of the pancreatic or biliary duct, or gastric outlet obstruction.

Abdominal fistula, GI perforation, bowel obstruction, or intra-abdominal abscess within 6 months before first dose.

Note: Complete healing of an intra-abdominal abscess must be confirmed before first dose.

Clinically significant hematuria, hematemesis, or hemoptysis of >0.5 teaspoon (2.5 mL) of red blood, or other history of significant bleeding (eg, pulmonary hemorrhage) within 12 weeks before first dose.

Cavitating pulmonary lesion(s) or known endobronchial disease manifestation.

Lesions invading major pulmonary blood vessels.

Other clinically significant disorders such as:

i. Active or history of autoimmune disease or immune deficiency, including, but not limited to, myasthenia gravis, myositis, autoimmune hepatitis, systemic lupus erythematosus, rheumatoid arthritis, psoriatic arthritis, inflammatory bowel disease, antiphospholipid antibody syndrome, Wegener granulomatosis, Sjögren's syndrome, Guillain-Barré syndrome, or multiple sclerosis (see Appendix D for a more comprehensive list of autoimmune diseases and immune deficiencies). Subjects with the following conditions are eligible for the study:

A history of autoimmune-related hypothyroidism and on thyroid replacement hormone.

Controlled Type 1 diabetes mellitus and on an insulin regimen.

Asthma that require intermittent use of bronchodilators.

Eczema, psoriasis, lichen simplex chronicus, or vitiligo with dermatologic manifestations only provided all of following are true:

Rash covers <10% of body surface area.

Disease is well controlled at baseline and requires only low-potency topical corticosteroids.

No occurrence of acute exacerbations of the underlying condition requiring psoralen plus ultraviolet A radiation, methotrexate, retinoids, biologic agents, oral calcineurin inhibitors, or high potency or oral corticosteroids within the previous 12 months.

Active infection requiring systemic treatment, infection with human immunodeficiency virus (HIV) or acquired immunodeficiency syndrome (AIDS)-related illness, or acute or chronic hepatitis B or C infection, or positive test for tuberculosis.

History of idiopathic pulmonary fibrosis, organizing pneumonia (eg, bronchiolitis obliterans), drug-induced pneumonitis, idiopathic pneumonitis, or evidence of active pneumonitis on screening chest computerized tomography (CT) scan. History of radiation pneumonitis in the radiation field (fibrosis) is permitted.

Serious non-healing wound/ulcer/bone fracture.

Malabsorption syndrome.

Uncompensated/symptomatic hypothyroidism.

Moderate to severe hepatic impairment (Child-Pugh B or C).

Requirement for hemodialysis or peritoneal dialysis.

History of solid organ or allogenic stem cell transplant.

Major surgery (eg, GI surgery, removal or biopsy of brain metastasis) within 8 weeks before first dose of study treatment, except prior nephrectomy within 6 weeks before first dose. Complete wound healing from major surgery must have occurred 3 weeks before first dose and from minor surgery (eg, simple excision, tooth extraction) at least 10 days before first dose. Subjects with clinically relevant ongoing complications from prior surgery are not eligible.

Corrected QT interval calculated by the Fridericia formula (QTcF)>500 ms per electrocardiogram (ECG) within 28 days before first dose of study treatment (see Section 5.6.4 for Fridericia formula).

Note: If a single ECG shows a QTcF with an absolute value >500 ms, two additional ECGs at intervals of approximately 3 min must be performed within 30 min after the initial ECG, and the average of these three consecutive results for QTcF will be used to determine eligibility.

Pregnant or lactating females.

Inability to swallow tablets.

Previously identified allergy or hypersensitivity to components of the study treatment formulations.

Diagnosis of another malignancy within 2 years before first dose of study treatment, except for superficial skin cancers, or localized, low grade tumors deemed cured and not treated with systemic therapy. Incidentally diagnosed prostate cancer is allowed in UC subjects if assessed as stage ≤T2N0M0, Gleason score ≤6, and PSA undetectable.

Estimated Length of Subject Participation

It is estimated that subjects with advanced previously treated UC, CRPC, NSCLC may receive study treatment for an average of 6 months, and subjects with advanced treatment-nave UC, RCC, NSCLC may receive study treatment for an average of 9 months. Subjects will however be followed until death, withdrawal of consent, or Sponsor decision to no longer collect these data.

Estimated Study Duration

It is estimated that 6 months will be required to enroll the subjects and determine the recommended dose and schedule in the Dose-Escalation Stage. It is estimated that 16 months will be required to enroll the eight cohorts in the Expansion Stage.

Investigational Regimen Dose/Route/Interval

Cabozantinib will be supplied as 60-mg and 20-mg tablets (expressed as freebase weight). In the Dose-Escalation Stage, cabozantinib will be administered orally daily at dose levels of 20, 40, or 60 mg.

Atezolizumab will be administered at a standard dosing regimen of 1200 mg as an IV infusion once every 3 weeks (q3w). The initial infusion of atezolizumab will be given over 60 (±15) minutes without premedication for potential infusion-related reactions. Subsequent IV infusions may be given over 30 (±10) minutes if the initial infusion is tolerated. Premedication for infusion-reaction is allowed after the initial infusion. No bolus or IV push of atezolizumab is allowed.

Initial cohorts in the Dose Escalation Stage will receive the combination regimen on a Standard Dosing Schedule with the first infusion of atezolizumab given on the same day as the first dose of cabozantinib. If deemed necessary, the CRC may decide to enroll additional cohorts in the Dose Escalation Stage on a Cabozantinib Run-In Dosing Schedule with the first infusion of atezolizumab given on Cycle 2 Day 1 (C2D1), 21 days after their first dose of single-agent cabozantinib. In the Expansion Stage, all subjects will receive cabozantinib at the recommended dose and schedule as determined by the CRC.

Safety Assessments

Safety evaluations will include assessments of AEs (including irAEs and AESIs), vital signs, ECGs, laboratory tests, and concomitant medications. Adverse event seriousness, severity grade, relationship to study treatment, and relationship to immune effects (ie, irAEs) will be assessed by the investigator. Severity grade will be defined by the NCI CTCAE version 4.

Tumor Assessments

Tumor response will be assessed using RECIST 1.1 (Appendix F). Additional exploratory efficacy evaluation will include the application of modified RECIST for immune response (Appendix 0). Subjects will be assessed using a magnetic resonance imaging (MRI) or a CT scan from the date of the first dose of study treatment until the later of radiographic disease progression per RECIST 1.1 as determined by the investigator or the date of the decision to permanently discontinue study treatment. Radiographic tumor assessments will continue on the protocol-defined schedule, regardless of whether study treatment is reduced, interrupted, delayed, or discontinued.

Chest/Abdomen/Pelvis (CAP): CT of CAP or CT chest and MRI abdomen/pelvis will be performed in all subjects at screening and every 6 weeks (±5 days) after initiation of study treatment throughout the first 12 months on study. Upon completion of 12 months on study, these assessments will be performed every 12 weeks (±7 days).

Brain: MRI (or CT) of the brain will be performed at screening in all subjects with RCC and NSCLC and for subjects with CRPC or UC who have a history or clinical symptoms of brain metastasis. After study treatment initiation MRI (or CT) scans of the brain are only required in subjects with known brain metastasis or if clinically indicated by signs and symptoms suggestive of new central nervous system (CNS) metastases. Assessments will be performed every 12 weeks (±7 days). MRI is the preferred imaging method for brain. If CT of the brain is performed instead of MRI ambiguous results must be confirmed by MRI. Subjects without documented brain metastasis during the screening assessment are not required to undergo brain imaging after C1D1 unless clinically indicated. In order to meet the eligibility requirements of the study, brain metastasis must have been treated and stable for at least 4 weeks before first dose.

Bone scans: Technetium bone scans (TBS) will be performed at screening in all subjects with CRPC and for subjects with RCC, UC, or NSCLC who have a history or clinical symptoms (ie, bone pain) of bone metastases. After study treatment initiation bone scans are only required in subjects with documented bone lesions or if clinically indicated by signs and symptoms suggestive of new bone metastases. Assessments after the first dose will follow routine clinical practice (approximately every 12 weeks throughout the first 12 months and every 24 weeks thereafter). Lesions identified on bone scan are not to be recorded as target, non-target, or new lesions. Bone scans are to be used to direct corroborative imaging with CT/MRI if necessary (these CT/MRI findings will be used for RECIST v1.1 evaluation), and bone scan findings alone should not be used for the determination of progression in this study.

Overall Survival Follow-Up Assessments

Subjects will be contacted approximately every 12 weeks after the post-treatment follow-up visit to assess survival status and to document receipt of subsequent anticancer therapy unless consent to participate in survival follow-up is withdrawn or the Sponsor deems sufficient efficacy data have been collected for the study.

Pharmacokinetic Assessments

Dose-Escalation Stage:

For subjects on the Standard Dosing Schedule, blood samples for PK analysis will be obtained on the date of first dose of study treatment (C1D1; prior to study treatment administration [cabozantinib and atezolizumab], approximately 5 min after completion of the atezolizumab infusion, and at 2 h, 4 h, and 6-8 h after cabozantinib dosing), and prior to study treatment dosing on C1D10, C2D1, and C3D1. For subjects on the Cabozantinib Run-In Dosing Schedule, blood samples for PK analysis will be obtained on the date of first dose (C1D1; samples taken prior to study treatment administration [cabozantinib and atezolizumab], and at 2 h, 4 h, and 6-8 h after cabozantinib dosing), and prior to study treatment on C2D1, C2D10, and C3D1.

Expansion Stage:

For subjects on the Standard Dosing Schedule, blood samples for PK analysis will be obtained on the date of first dose of study treatment (C1D1; prior to study treatment administration [cabozantinib and atezolizumab], approximately 5 min after completion of the atezolizumab infusion, and 2 h after the first dose of cabozantinib) and prior to study treatment dosing on C2D and C3D1. For subjects on the Cabozantinib Run-In Dosing Schedule, blood samples for PK analysis will be obtained on the date of first dose (C1D1; samples taken prior to study treatment administration [cabozantinib and atezolizumab] and 2 h after the first dose of cabozantinib) and prior to study treatment on C2D1 and C3D1.

In both stages, samples will be analyzed for cabozantinib concentration; concentrations of atezolizumab may be measured if needed. Collection of PK samples may be halted early or sampling frequency may be modified at the discretion of the Sponsor.

Biomarker Assessments

Peripheral blood and tumor tissue will be collected and may be assessed for exploratory biomarker analyses. Peripheral blood samples will be obtained as specified in the Schedule of Assessments. Tumor tissue (archival) will be obtained prior to first dose of study treatment, and optional fresh tumor tissue biopsies may also be performed. Exploratory analyses may include the following: MET, AXL, and PD-L1 in tumor specimens for association with clinical outcomes.

Immune cell infiltration and tumor characteristics (ie, mutational load assessment) in tumor specimens and blood for association with clinical outcome Circulating immune cells in peripheral blood (ie, lymphocyte subset analyses by flow cytometry)

Blood biomarkers (ie, cytokines/chemokines, VEGF)

For CRPC only: Changes in PSA and evaluation of MMR and MSI status response (PR) per RECIST 1.1 as determined by the investigator. ORR will be evaluated independently within each of the Expansion Cohorts.

The primary purpose of estimating ORR is to assess if the true response rate with this combination regimen is better than that expected with monotherapy. Thus, 2-sided 80% and 60% Blyth-Still-Casella confidence intervals (CIs) will be constructed for ORR, providing 90% and 80% 1-sided confidence, respectively, when interpreting the lower bound. The sample size of 30 subjects for the Expansion Cohorts was chosen to ensure the lower bound of the 2-sided 80% CI extended no more than 12 percentage points from the point estimate. Example 80% and 60% 2-sided CIs, with the 1-sided interpretations of the lower bound, are shown in the table below for a range of potential values for observed ORR.

Example Blyth-Stir-Casella Confidence Intervals for ORR for the Expansion Cohorts of 30 Subjects with 1-Sided Interpretations of the Lower Bound

| Observed Responses (Total N = 30) | Observed ORR | 80% 2-Sided CI | | | 60% 2-Sided CI | | |
|---|---|---|---|---|---|---|---|
| | | LCL | UCL | True ORR$^a$ (90% Confidence) | LCL | UCL | True ORR$^a$ (80% Confidence) |
| 17 | 0.57 | 0.44 | 0.69 | ≥44% | 0.47 | 0.66 | ≥47% |
| 15 | 0.50 | 0.38 | 0.62 | ≥38% | 0.41 | 0.59 | ≥41% |
| 12 | 0.40 | 0.28 | 0.53 | ≥28% | 0.31 | 0.47 | ≥31% |
| 11 | 0.37 | 0.25 | 0.50 | ≥25% | 0.28 | 0.44 | ≥28% |
| 10 | 0.33 | 0.23 | 0.46 | ≥23% | 0.25 | 0.41 | ≥25% |
| 9 | 0.30 | 0.19 | 0.42 | ≥19% | 0.24 | 0.38 | ≥24% |
| 8 | 0.27 | 0.16 | 0.38 | ≥16% | 0.19 | 0.34 | ≥19% |
| 7 | 0.23 | 0.15 | 0.34 | ≥15% | 0.16 | 0.31 | ≥16% |
| 6 | 0.20 | 0.11 | 0.31 | ≥11% | 0.13 | 0.28 | ≥13% |
| 5 | 0.17 | 0.09 | 0.28 | ≥9% | 0.12 | 0.24 | ≥12% |
| 4 | 0.13 | 0.06 | 0.25 | ≥6% | 0.08 | 0.19 | ≥8% |

CI, confidence interval;
LCL, lower confidence limit;
ORR objective response rate;
UCL, upper confidence limit.
$^a$Per 1-sided interpretation of the lower bound.

Collection of biomarker samples may be halted early or sampling frequency may be modified at the discretion of the Sponsor.

For NSCLC subjects, available tumor mutation analysis reports should be provided at screening.

Statistical Methods

Dose-Escalation Stage:

The number of subjects per dose escalation cohort has been chosen based on a well-established Phase 1 dose-escalation trial design. Subjects are accrued into cohorts in a "3 plus 3" fashion with each cohort consisting initially of 3 subjects and potentially expanding to 6 subjects based upon the number of DLTs observed. A total of 9 to 36 subjects are expected to be enrolled in this stage, depending upon the number of escalation cohorts and subjects required to establish an MTD or recommended Expansion Stage dose and schedule.

Summaries will focus on AEs and tumor response by cohort. A narrative will also be prepared to describe the accrual and expansion of dose-escalation cohorts, subject replacement, the DLTs observed, CRC decisions and the final rationale for the recommended Expansion Stage dose and schedule.

Expansion Stage:

Objective Response Rate: The objective of the Expansion Stage is to estimate ORR, defined as the proportion of subjects with a confirmed complete response (CR) or partial The planned enrollment of 30 subjects each in Expansion Cohorts 5 and 7 will be divided between 15 subjects with ICI refractory disease (PD as best response to prior ICI therapy) and 15 subjects with ICI resistant disease (CR, PR, stable disease [SD] as best response to prior ICI therapy). The sample size of 15 subjects was chosen to ensure the lower bound of the 2-sided 80% CI extended no more than 19 percentage points from the point estimate. Example 80% and 60% 2-sided CIs, with the 1-sided interpretations of the lower bound, are shown in the table below for a range of potential values for observed ORR. Should the subjects who are ICI refractory and/or ICI resistant reach a clinically meaningful ORR as defined by the Study Oversight Committee, approximately 50 subjects may be added to Cohort 5 and/or 7 (ie, up to a total of 80 subjects per cohort) to further investigate the safety and clinical benefit of the combination in this treatment setting that has high unmet need and a novel mechanism of action of re-sensitizing to ICI therapy. Decisions regarding the clinical meaningfulness of the achieved ORR in Expansion Cohorts 5 and 7 by the Study Oversight Committee will be based on the lower bound of 80% CI for the entire Cohort of 30 subjects or 15 subjects with ICI refractory disease and 15 subjects with ICI resistant disease, as appropriate. A target observed ORR of 20-25% for Expansion Cohort 5 and 15-20% for Expansion Cohort 7 may be used as guidance by the Study Oversight Committee. This generally corresponds to 80% confidence the true ORR is ?11% for n=15 or ≥13% for n=30. The expansion of Cohort 5 and/or 7 with 50 additional subjects may be limited to either ICI refractory or ICI resistant subjects or may include subjects from both groups depending on the observed ORR.

Example Blyth-Still-Casella Confidence Intervals for ORR for the Expansion Cohorts of 15 Subjects with 1-Sided Interpretations of the Lower Bound

| Observed Responses (Total N = 15) | Observed ORR | 80% 2-Sided CI | | | 60% 2-Sided CI | | |
|---|---|---|---|---|---|---|---|
| | | LCL | UCL | True ORR$^a$ (90% Confidence) | LCL | UCL | True ORR$^a$ (80% Confidence) |
| 9 | 0.60 | 0.42 | 0.77 | ≥43% | 0.46 | 0.70 | ≥46% |
| 7 | 0.47 | 0.28 | 0.64 | ≥28% | 0.33 | 0.61 | ≥33% |
| 6 | 0.40 | 0.23 | 0.57 | ≥23% | 0.30 | 0.54 | ≥30% |
| 5 | 0.33 | 0.20 | 0.51 | ≥20% | 0.23 | 0.46 | ≥23% |
| 4 | 0.27 | 0.12 | 0.44 | ≥12% | 0.16 | 0.39 | ≥16% |
| 3 | 0.20 | 0.10 | 0.36 | ≥10% | 0.11 | 0.33 | ≥11% |
| 2 | 0.13 | 0.06 | 0.28 | ≥6% | 0.08 | 0.23 | ≥8% |
| 1 | 0.07 | 0.01 | 0.23 | ≥1% | 0.03 | 0.16 | ≥3% |

CI, confidence interval;
LCL, lower confidence limit;
ORR objective response rate;
UCL, upper confidence limit.
$^a$Per 1-sided interpretation of the lower bound.

PFS and OS: Median PFS and OS will be estimated using Kaplan-Meier methods.

DOR: DOR medians will be estimated using Kaplan-Meier analysis and will be limited to patients who experienced a confirmed objective response.

Safety: Summaries of AEs, irAEs, AESIs, and SAEs will be tabulated by cohort according to system organ class and preferred term by overall incidence; worst reported severity; and relationship to study treatment. Selected laboratory test results will be summarized by treatment group to evaluate worst post Example 2. A Phase Ib Study of Cabozantinib with Atezolizumab for the Treatment of Locally Advanced or a Metastatic Solid Tumors 1. Background and Rationale
1.1 Background Multi-targeted tyrosine kinase inhibitors (TKIs) and immune checkpoint inhibitors (ICIs) immunotherapies represent two systemic modalities that have been instrumental in the recent advancements of anticancer treatment over the past several years. Both classes of therapies have demonstrated broad clinical effects leading to new approved treatment options across multiple tumor types including renal cell carcinoma (RCC), urothelial carcinoma (UC), melanoma, non-small cell lung cancer (NSCLC), and others. The success of these therapy types as single agents with distinct mechanisms of action has naturally led to interest in evaluating combinations of TKIs with ICIs in search of further, possibly synergistic, anticancer clinical effects.

1.1.1 Atezolizumab

Atezolizumab is a humanized immunoglobulin (Ig) 01 monoclonal antibody which potently and selectively inhibits binding of programmed death receptor 1 ligand (PD-L1) on tumor cells and tumor infiltrating immune cells in the tumor microenvironment (McDermott at al 2016). Through this interaction, atezolizumab interrupts the negative regulatory effects of PD-L1 on T-cell proliferation and function that result from PD-L1 binding to programmed death receptor 1 (PD-1) and B7.1 (CD80) expressed on T lymphocytes and other immune cells. The result is an increase in the susceptibility of tumor cells to T-cell-mediated immune response, an effect that has been demonstrated in clinical activity across several tumor types.

Atezolizumab has been approved in the United States and the European Union for the treatment of patients with localized advanced or metastatic UC after prior platinum-containing chemotherapy or who are considered cisplatin-ineligible (Rosenberg et al 2016, Loriot et al 2016). Atezolizumab is also approved for patients with locally advanced or metastatic NSCLC after prior chemotherapy (Fehrenbacher et al 2016; Tecentriq US Prescribing Information and EMA SmPC). Patients with epidermal growth factor receptor (EGFR) activating mutations or anaplastic lymphoma kinase (ALK)-positive tumour mutations should also have received targeted therapy before receiving atezolizumab. In these tumor indications, atezolizumab has either prolonged overall survival (OS) or induced durable disease responses. Notably, similar to other ICIs, the effects of atezolizumab on progression-free survival (PFS) were modest suggesting the possibility of delayed anticancer immune effects contributing to the observed survival benefit (Fehrenbacher et al 2016). Like other ICIs, treatment with atezolizumab is generally well-tolerated but can be associated with immune-related adverse events (irAEs) including pneumonitis, hepatitis, colitis, endocrinopathies including hypophysitis, ocular toxicity, myocarditis, and pancreatitis (Michot et al 2016).

1.1.1.1 Clinical Experience in Urothelial Carcinoma

Regulatory approval of atezolizumab in locally advanced or metastatic UC was received based on results from a multicenter, open-label, Phase 2 study using objective response rate (ORR) per Response Evaluation Criteria in Solid Tumors (version 1.1)(RECIST 1.1) by independent review facility (IRF) as primary endpoint, and based on the results from a randomized multicenter Phase 3 study comparing atezolizumab with standard of care chemotherapy in subjects previously treated with a platinum-based chemotherapy.

In cohort 2 of the Phase 2 study, which enrolled UC subjects who had received prior platinum-based chemotherapy, the overall ORR by IRF was 14.8%(95% confidence interval [CI]: 11.1, 19.3), for subjects with ? 5% PD-L1 expression 26.0% [95% CI: 17.7, 35.7], and for subjects with <5% PD-L1 expression 9.5% [95% CI: 5.9, 14.3] (Rosenberg et al 2016; TECENTRIQ® US Prescribing Information). Median PFS for the overall population was 2.1 months (95% CI: 2.1, 2.1); subgroup analysis of PFS yielded similar results irrespective of PD-L1 expression level. Median OS for the overall population was 7.9 months (95% CI: 6.6, 9.3); however, survival was longer in subjects with 5% PD-L1 expression with a median OS of 11.9 months [95% CI: 9.0, not estimable {NE}] (Loriot et al 2016). Atezolizumab was well-tolerated in this study population; the most frequently reported adverse events (AEs) in descending order of frequency were fatigue, decreased appetite, nausea, urinary tract infection, pyrexia, and constipation. Adverse events led to treatment discontinuation in 3.2% of subjects. The most frequently reported irAEs (2% each) were pneumonitis and aspartate aminotransferase (AST) increased. Treatment-emergent anti-therapeutic antibodies were detected in 41.5% of subjects at one or more post-dose time points. However, the presence of these antibodies did not appear to have a clinically significant impact on pharmacokinetics (PK), safety or efficacy.

In the Phase 3 study, which also enrolled UC subjects after prior platinum-based chemotherapy, the results of atezolizumab were generally consistent with the Phase 2 study data. The overall ORR was 13%(95% CI: 11, 17) and for subjects with 5% PD-L1 expression 23.0% [95% CI: 16, 32]. The duration of response (DOR) in the overall population for the atezolizumab arm was 21.7 months compared with 7.4 months on the chemotherapy arm. Although the primary endpoint of OS in this study in the PD-L1 positive (5% expression level) was not met, there were numerical improvements in OS in the overall population (HR=0.85; 95% CI 0.73, 0.99) confirming the clinical benefit of atezolizumab in this patient population compared to standard of care chemotherapy. In addition, the safety profile of atezolizumab in this study was more favorable than for chemotherapy (Powles et al 2017).

In cohort 1 of the Phase 2 study, which enrolled treatment-naïve subjects with cisplatin-ineligible UC, the overall ORR by IRF was 23% (95% CI: 16, 31), for subjects with ≥5% PD-L1 expression 28% (95% CI: 14, 47), and for subjects with <5% PD-L1 21% (Bellmunt et al 2016). The median OS for all subjects irrespective of PD-L1 expression level was 15.9 months (95% CI: 10.4, NE). The safety experience in treatment-naïve UC subjects was similar to subjects who had received prior platinum-based therapy.

A multi-center, randomized Phase 3 study evaluating atezolizumab as single-agent or in combination with platinum-based chemotherapy in subjects with treatment-naïve advanced UC (cisplatin-eligible and cisplatin-ineligible) is ongoing and results from this study are not yet available (NCT02807636).

1.1.1.2 Clinical Experience in Renal Cell Carcinoma

Safety, tolerability, and preliminary clinical activity of single-agent atezolizumab in subjects with advanced RCC of clear cell or non-clear cell histology was demonstrated in a Phase 1 study (McDermott et al 2016). Approximately 10% of subjects in this study had not received prior systemic treatment for RCC. The ORRs for clear cell RCC ranged from 9 to 18% depending on PD-L1 expression status. Overall median PFS and median OS for subjects with clear cell RCC were 5.6 months (95% CI: 3.9, 8.2) and 28.9 months (95% CI: 20.0, NE), respectively. One subject with non-clear cell RCC experienced a response per immune-related response criteria. Treatment-related Grade 3 events were reported for 17% of subjects, and there were no Grade 4 or 5 treatment-related AEs.

Atezolizumab has also demonstrated encouraging clinical activity in combination with the vascular endothelial growth factor (VEGF)-targeting antibody bevacizumab in a randomized Phase 2 study in treatment-naïve metastatic RCC (Atkins et al 2017). The ORR regardless of PD-L1 expression level was 32% and in PD-L1 positive subjects (≥1% PD-L1 expression) was 46%. Median PFS regardless of PD-L1 expression level was 11.7 months (95% CI: 8.4-17.3) and in PD-L1 positive subjects 14.7 months (95% CI: 8.2-25.1). The safety profile of this combination therapy was consistent with the safety profiles of the individual treatment components.

A multicenter, randomized Phase 3 study comparing atezolizumab in combination with bevacizumab with sunitinib as first-line therapy in advanced RCC is ongoing (NCT01984242). Recently, a positive topline result of the co-primary endpoint PFS was announced. The combination of atezolizumab with bevacizumab demonstrated a statistically significant improvement of investigator-assessed PFS compared with sunitinib in patients with PD-L1 expression (Roche data on file), 1.1.13 Clinical Experience in No-Small Cell Lung Cancer Regulatory approval of atezolizumab in platinum-pretreated NSCLC was received based on results from a multicenter, randomized Phase 3 study of atezolizumab compared with docetaxel (Rittmeyer et al 2017). Subjects received either atezolizumab (1200 mg) or docetaxel (75 mg/m$^2$) every 3 weeks. Coprimary endpoints were OS in the ITT population and PD-L1 positive population (2 1% PD-L1 expression). Overall survival was significantly improved with atezolizumab compared with docetaxel in the ITT population (median OS: 13.8 vs 9.6 months; hazard ratio [HR]=0.73, p=0.0003) and the PD-L1 positive population (median OS: 15.7 vs 10.3 months; HR=0.74, p=0.0102). The ORR was similar for the treatment arms (14% for atezolizumab vs 13% for docetaxel) in the ITT population; however, median DOR was longer with atezolizumab (16.3 months vs 6.2 months). Fewer subjects discontinued treatment due to AE in the atezolizumab arm (8%) versus the docetaxel arm (19%). The most common AEs of any grade for subjects on the atezolizumab arm were fatigue (14%), nausea (9%), decreased appetite (9%), and asthenia (8%). Immune-related AEs reported with atezolizumab included pneumonitis (four subjects, all Grade 3), hepatitis (two subjects, both Grade 4), and colitis (two subjects, both Grade 2). Fewer subjects had treatment-related Grade 3 or 4 AEs with atezolizumab (15%) than with docetaxel (43%).

Encouraging clinical activity of atezolizumab as first-line therapy in advanced NSCLC was demonstrated in a multi-center Phase 2 study (Peters et al 2017). Enrollment was selected on the basis of PD-L1 expression (2 5%) on tumor cells or immune cells. In untreated NSCLC patients with PD-L1 expression of 250% on tumor cells or 210% on immune cells (PD-L1 high group) the ORR (31%) per IRF was comparable to standard of care chemotherapy in this treatment setting. Median OS (26.9 months) in the PD-L1 high group was longer compared with standard of care chemotherapy in this treatment setting. Median duration of response in the PD-L1 high group was ~10 months and median PFS was 5.4 months. Subgroup analyses supported the hypothesis that results in radiographic endpoints PFS and ORR were dependent on the PD-L1 expression status; however, the observed OS benefit deemed to be independent of the PD-L1 expression status. Treatment-related AEs of Grade 3 or 4 of atezolizumab monotherapy occurred in 9% of subjects. There was no treatment-related Grade 5 event. Adverse events leading to treatment discontinuation occurred in 7% of subjects and included Grade 3 or 4 pneumonitis (1%) and any grade pneumonia (1%).

Ongoing multicenter, randomized Phase 3 trials in chemotherapy-naïve advanced NSCLC are evaluating atezolizumab versus chemotherapy (non-squamous NSCLC: NCT02409342, squamous NSCLC: NCT02409355), atezolizumab in combination with chemotherapy versus chemotherapy (non-squamous NSCLC: NCT02367781; squamous NSCLC: NCT02367794), or atezolizumab in combination with chemotherapy and bevacizumab versus chemotherapy and bevacizumab (non-squamous NSCLC: NCT02366143). Recently, positive topline results were announced for the combination of atezolizumab/chemotherapy/bevacizumab. The combination of atezolizumab chemotherapy/bevacizumab demonstrated an improvement of the co-primary endpoint PFS compared with chemotherapy/bevacizumab in non-squamous NSCLC subjects (median PFS 8.3 months vs 6.8 months; HR 0.617 (95% CI: 0.517, 0.737; P<0.0001). A PFS benefit was also observed in subjects with EGFR and ALK genetic alterations, PD-L1-negative tumors, and liver metastases. At the time of the PFS analysis the coprimary OS data was not mature (Reck et al 2017).

1.1.1.4 Clinical Experience in Castration-Recurrent Prostate Cancer

Prostate cancer patients who progress on androgen-deprivation therapy (castration-recurrent prostate cancer, CRPC) have a poor prognosis. At this stage of disease, standard treatment options include anti-androgen therapy (eg, enzalutamide, abiraterone), chemotherapy (eg, docetaxel, cabazitaxel), and radionuclides (eg, radium 223). There is emerging evidence that certain types of immunotherapy may provide clinical benefits to patients with advanced prostate cancer. For example, Sipuleucel T, a cancer vaccine, has been approved for minimally symptomatic metastatic CRPC (Kantoff et al 2010). Recently, immune checkpoint inhibitors (ICIs) have been evaluated as potential new treatment modality for patients with CRPC. For example, the PD-1 inhibitor pembrolizumab has shown encouraging preliminary clinical activity in CRPC patients following progression on the anti-androgen blocker enzalutamide with normalization of prostate-specific antigen (PSA), radiographic responses, and resolution of cancer pain (Graff et al 2016). A possible explanation of the observed clinical activity is based on the observation of upregulated PD-L1 expression by exposure to enzalutamide (Bishop et al 2015). These data suggest that the likelihood of a response to immunotherapy in CRPC may be improved after progression on enzalutamide therapy. In addition, targeting immunosuppressive cell subsets found in both the tumor and peripheral blood may be important in augmenting anti-tumor immune responses in prostate cancer patients (Miller et al 2010; Idorn et al. 2014).

A multicenter, randomized Phase 3 trial of the combination of atezolizumab with enzalutamide after failure of an androgen synthesis inhibitor in CRPC is ongoing; results from this study are not yet available (NCT03016312).

1.2 Cabozantinib

Cabozantinib (XL184) is a potent inhibitor of multiple receptor tyrosine kinases (RTKs) known to play important roles in tumor cell proliferation and/or tumor neovascularization including MET, vascular endothelial growth factor receptor (VEGFR), AXL, and RET. Increased expression of MET and AXL has been implicated in the development of resistance to VEGFR inhibitors in preclinical models of several cancers (Shojaei et al 2010, Zhou et al 2016, Sennino et al 2012, Ciamporcero et al 2015). In addition, targets of cabozantinib are implicated in promoting tumor-immune suppression including TYRO3, MER, and AXL (tumor-assisted macrophage [TAM] family kinases). Cabozantinib has demonstrated broad preclinical and clinical activity across several tumor types including RCC, UC, CRPC, and NSCLC. In the United States and the European Union, cabozantinib capsules (140 mg) are approved for the treatment of progressive, metastatic medullary thyroid cancer (Elisei et al 2013; Cometriq™ US PI and EMA SmPC) and cabozantinib tablets (60 mg) are approved for patients with advanced RCC after prior anti-angiogenic/VEGFR-targeted therapy (Choueiri et al 2015, Choueiri et al 2016, Cabometyx™ US PI and EMA SmPC). Cabozantinib is also listed as recommended therapy in patients with untreated RCC of intermediate- and poor-risk (NCCN 2017), and is currently under review by regulatory agencies in the US and the European Union based on statistically improved PFS compared with sunitinib (Choueiri et al [J Clin Oncol]2017, Choueiri et al [Ann Oncol]2017).

Summaries of cabozantinib pharmacology, toxicology, PK, and clinical data are contained in the Investigator's Brochure supplied by the Sponsor (or designee), which must be reviewed before initiating the study.

1.2.1 Nonclinical Toxicology

Cabozantinib nonclinical toxicology has been characterized in single- and repeat-dose studies in multiple species. Details can be found in the Investigator's Brochure.

1.2.2 Clinical Experience in Renal Cell Carcinoma

The cabozantinib approval in previously treated RCC was based on the results of a multicenter, randomized, controlled Phase 3 study comparing open-label cabozantinib (60 mg, tablets) with everolimus in 658 subjects (330 cabozantinib, 328 everolimus) with advanced disease who had received prior therapy with at least one VEGFR-TKI (Choueiri et al 2015, Choueiri et al 2016, Cabometyx US PI and EMA SmPC). Cabozantinib demonstrated statistically significant improvements in the primary endpoint (PFS) and both secondary endpoints (ORR, OS) compared with the standard-of-care in the control arm (everolimus). In the primary PFS analysis performed in the first 375 subjects randomized (Primary Endpoint Intent-to-Treat population), the HR per independent radiology committee (IRC) adjusted for stratification factors was 0.58 (95% CI: 0.45, 0.74; stratified log-rank p-value <0.0001), and the Kaplan-Meier estimates for median duration of PFS were 7.4 months in the cabozantinib arm vs 3.8 months in the everolimus arm. In the primary analysis of ORR per IRC conducted in the intent-to-treat (ITT) population at the time of the primary analysis of PFS, the ORRs for the cabozantinib and everolimus arms, were 17% (95% CI: 13, 22) and 3% (95% CI: 2, 6), respectively (unstratified p-value <0.0001). In a subsequent unplanned interim OS analysis with a prospectively-defined cutoff date providing a minimum follow-up of 13 months from the last subject randomized, a highly statistically significant prolongation of OS for subjects in the cabozantinib arm compared with the everolimus arm was demonstrated: the HR, adjusted for stratification factors was 0.66 (95% CI: 0.53, 0.83; stratified log-rank p-value 0.0003). Kaplan-Meier estimates for median duration of OS were 21.4 months in the cabozantinib arm and 16.5 months in the everolimus arm. Results for extensive subgroup analyses of PFS, OS, and ORR showed a consistent benefit for cabozantinib treatment versus everolimus. The observed clinical activity of cabozantinib was applicable to subjects in all risk categories per Memorial Sloan-Kettering Cancer Center (MSKCC) criteria and was irrespective of previous treatments and the extent of tumor burden. Consistent with the known safety profile for cabozantinib, the most frequently reported AEs for subjects who received cabozantinib on study in decreasing order of frequency were diarrhea, fatigue, nausea, decreased appetite, palmar-plantar erythrodysesthesia (PPE), hypertension, vomiting, weight decreased, and constipation (Cabometyx US Prescribing Information). Adverse events were generally adequately managed with dose modifications (reductions and interruptions) with dose reductions from 60 mg to 40 mg occurring in 60% of subjects and further dose reductions from 40 mg to 20 mg occurring in 20% of subjects. Treatment discontinuations due to AEs were similar between the two treatment arms (10% incidence in each arm), and the most frequent AEs leading to treatment discontinuation in the cabozantinib arm were decreased appetite and fatigue.

In addition, study results were positive from a randomized Phase 2 trial of cabozantinib (60 mg) in 157 subjects (79 cabozantinib, 78 sunitinib) with previously-untreated RCC conducted as part of a collaboration with the National Cancer Institute's (NCI) Cancer Therapy Evaluation Program (CTEP; Choueiri et al [J Clin Oncol] 2017). The trial met its primary endpoint, demonstrating a statistically-significant and clinically-meaningful improvement in PFS for cabozantinib compared with sunitinib in previously untreated subjects with advanced RCC of intermediate- or poor-risk per International Metastatic RCC Database Consortium criteria. The median PFS per Investigator for the cabozantinib arm was 8.2 months (95% CI 6.2, 8.8) compared with 5.6 months (95% CI 3.4, 8.1) on the sunitinib arm. Cabozantinib reduced the rate of disease progression or death by 34% compared with sunitinib (adjusted HR, 0.66, 95% CI 0.46 to 0.95; Choueiri et al [J Clin Oncol] 2017). Median PFS per IRC for the cabozantinib arm was 8.6 months (95% CI 6.8, 14.0) compared with 5.3 months (95% CI 3.0, 8.2) on the sunitinib arm (Choueiri et al [Ann Oncol]2017). Median OS was 26.6 months on the cabozantinib arm and 21.2 months on the sunitinib arm (HR 0.79, 95% CI 0.53, 1.2; two-sided p=0.27). Adverse events of ≥Grade 3 regardless of causality occurred in 68% of cabozantinib subjects and 65% of sunitinib subjects; these events included diarrhea (cabozantinib 10%, sunitinib 11%), fatigue (6%, 17%), hypertension (28%, 21%), PPE (8%, 4%), and hematological events (2%, 21%). In both study arms, 16 subjects (20% cabozantinib, 21% sunitinib) discontinued study treatment due to an AE. The safety data in the cabozantinib-treated arm of the study were consistent with those observed in previous studies in subjects with advanced RCC.

1.2.3 Clinical Experience in Urothelial Carcinoma

Cabozantinib (60 mg) has been evaluated as a single agent in an open-label Phase 2 study of subjects with relapsed or refractory metastatic UC (NCT01688999, Apolo et al [J Clin Oncol] 2016). A total of 67 eligible subjects with diagnoses of progressive metastatic carcinoma of the bladder, urethra, ureter, or renal pelvis were enrolled in three cohorts. The largest cohort (Cohort 1) enrolled 50 subjects with metastatic UC. In Cohort 1, the primary endpoint of ORR for 42 evaluable subjects was 19.1% with 7 PRs and 1 complete response (CR) for single-agent cabozantinib. Median PFS and median OS for these subjects were 3.7 months (95% CI: 3.1, 6.5) and 8.0 months (95% CI: 5.2, 10.3), respectively. Across all cohorts (n=67), the most frequent (5% incidence) Grade 3 AEs related to cabozantinib treatment were fatigue (9%), hypertension (7%), and hypophosphatemia (6%). Cabozantinib-related Grade 4 AEs were reported for hypomagnesemia (3%) and lipase increased (1%).

In an ongoing Phase 1 clinical trial in subjects with refractory metastatic UC and other genitourinary (GU) tumors, cabozantinib has been evaluated in combination with nivolumab, a monoclonal antibody to PD-1 (referred to as doublet), and in combination with nivolumab and ipilimumab, a monoclonal antibody targeting CTL4-A (referred to as triplet)(Apolo et al 2016, Nadal et al 2017). The doublet and triplet combinations were well tolerated and no dose-limiting toxicities (DLTs) were reported (Apolo et al 2016). The recommended phase 2 doses for the doublet combination were cabozantinib 40 mg daily (qd) with nivolumab 3 mg/kg IV every other week (q2w), and for the triplet combination cabozantinib 40 mg qd with nivolumab 3 mg/kg IV q2w and ipilimumab 1 mg/kg IV every third week (q3w; maximum 4 doses). At the data cutoff, 42 subjects across both the doublet and triplet combinations were evaluable for safety and response analyses. The ORR across all subjects with heavily pre-treated GU tumors was 33% (Nadal et al 2017). Among the metastatic UC subjects, a 38% ORR was reported with 15% achieving a CR. Also, subjects with rare UC types such as urachal adenocarcinoma and squamous cell carcinoma of the bladder responded to this combination therapy. After a median follow up of 16 months, median DOR was not reached with approximately 70% ongoing responses; the median OS was 20 months among enrolled GU cancers. Grade 3 or 4 treatment-related AEs across all different dose levels explored for the doublet combination (n=24 subjects) were fatigue (12%), hypertension (8%), diarrhea (4%), nausea or vomiting (4%), abdominal pain (4%), thromboembolic events (4%), and kidney infection (4%). Most frequent Grade 3 or 4 treatment-related AEs across all different dose levels explored for the triplet combination (n=18 subjects) were fatigue (11%), hypertension (17%), diarrhea (5%), anorexia (5%), oral mucositis or sore throat (5%), thromboembolic events (5%). Immune-related Grade 3 or Grade 4 AEs on the doublet combination arm comprised one case of aseptic meningitis, and on the triplet combination arm one event of colitis and hepatitis each. Grade 3 or 4 laboratory abnormalities reported in 2 subjects on the doublet arm across all explored dose levels were decreased neutrophil count (n=6), hypophosphatemia (n=5), increased lipase (n=4), decreased platelet count (n=2), hyponatremia (n=2), and proteinuria (n=2). Grade 3 or 4 laboratory abnormalities reported in 2 subjects on the triplet arm across all explored dose levels were hypophosphatemia (n=4), increased lipase (n=4), decreased lymphocyte count (n=3), hyponatremia (n=2), hypocalcemia (n=2), alanine aminotransferase (ALT) increased (n=2, both Grade 3), AST increased (n=1, Grade 3), and amylase increased (n=1). There was no Grade 5 AE. This trial is currently enrolling additional subjects with GU cancers in expansion cohorts.

1.2.4 Clinical Experience in Castration-Recurrent Prostate Cancer

Following encouraging preliminary results for cabozantinib-treated CRPC subjects in a Phase 2 study (Smith et al 2013, Smith et al 2014, Basch et al 2015), a randomized, double-blind, comparator controlled Phase 3 study was conducted in heavily pretreated subjects with advanced CRPC with bone metastases. Subjects were randomized to receive either cabozantinib or prednisone, and the primary endpoint was OS. The prespecified primary analysis of OS was based on an ITT analysis of all randomized subjects and did not demonstrate a statistically significant improvement for subjects in the cabozantinib arm compared with the prednisone arm (HR=0.90 [95% CI: 0.76, 1.06; stratified log-rank p-value 0.213]); the Kaplan-Meier estimates for median duration of OS were 11.0 months in the cabozantinib arm and 9.8 months in the prednisone arm (Smith et al 2016). Although, the study failed to meet its primary endpoint, encouraging activity was still demonstrated in secondary and exploratory endpoints. The secondary efficacy endpoint was the proportion of subjects with a bone scan response (BSR; defined as a ≥30% decrease in total bone-scan lesion area compared with baseline without soft-tissue disease progression) per IRC at Week 12. The analysis demonstrated a statistically significant improvement of BSR in the cabozantinib arm compared with the prednisone arm (42% vs 3%; stratified Cochran-Mantel-Haenszel [CMH] p-value <0.001). The median duration of BSR was 5.8 vs 1.8 months. Median PFS per investigator (exploratory endpoint) was 5.6 months in the cabozantinib arm and 2.8 months in the prednisone arm (HR=0.48 [95% CI: 0.40, 0.57; stratified log-rank p-value <0.0001]). Cabozantinib treatment was also associated with improvements in bone-related biomarkers and incidence of skeletal-related events.

Additional encouraging preliminary results in CRPC subjects have been observed in the ongoing Phase 1 study combining cabozantinib with the ICI nivolumab (+/−ipilimumab). One of nine enrolled subjects with metastatic CRPC (11%) experienced a PR, and 67% had stable disease as their best response. (Nadal et al 2017). These results warrant further evaluation of the combination of cabozantinib with ICIs in CRPC.

1.2.5 Clinical Experience in Non-Small Cell Lung Cancer

Cabozantinib has been evaluated as a single agent or in combination in several early stage clinical trials in patients with advanced NSCLC.

In an open-label, randomized Phase 2 study, 125 NSCLC subjects without EGFR genetic alterations received cabozantinib, erlotinib, or both agents in combination as second or third line treatment (Neal et al 2016). Compared with erlotinib alone, the primary endpoint PFS was significantly improved in subjects receiving cabozantinib as single agent (4.3 vs 1.8 months; HR=0.39, p=0.0003) and in combination with erlotinib (4.7 vs 1.8 months; HR=0.37, p=0.0003). The estimated median OS for cabozantinib treated subjects was 9.2 months (95% CI 5.1, 15.0), for cabozantinib with erlotinib was 13.3 months (95% CI 7.6, NR), and for erlotinib alone was 5.1 months (95% CI 3.3-9.3). The ORR for subjects treated with cabozantinib alone was 11%, with the combination of cabozantinib with erlotinib was 3%, and with erlotinib alone was 3%. Notably, progression as best response was reported for 66% of subjects treated with erlotinib alone compared with 23-24% for subjects treated with cabozantinib alone or in combination with erlotinib. The most common Grade 3 or 4 AEs for single-agent cabozantinib were hypertension (25%), fatigue (15%), oral mucositis (10%), diarrhea (8%), and thromboembolic event (8%). One death due to respiratory failure assessed as possibly related to study drug occurred in the cabozantinib arm, and one death due to pneumonitis assessed as related to either study drug or the combination occurred in the erlotinib plus cabozantinib arm.

In a randomized discontinuation Phase 2 study, 60 subjects with advanced NSCLC were enrolled and received cabozantinib as single agent therapy (Schöffski et al 2017). The ORR was 10% and 48.3% of subjects experienced stable disease as their best response. Median PFS in this study was 4.0 months.

In a single-arm, open-label Phase 2 trial, 26 subjects with advanced RET-rearranged NSCLC received cabozantinib as single-agent therapy (Drilon et al 2016). The study met its primary endpoint, with an overall response rate of 28%(95% CI 12, 49). The median duration of treatment was 4.7 months. The median PFS was 5.5 months (95% CI 3.8 to 8.4). The median OS was 9.9 months (95% CI 8.1 to not reached). The most common Grade 3 treatment-related AEs were lipase elevation (15%), increased ALT (8%), increased AST (8%), decreased platelet count (8%), and hypophosphataemia (8%). No treatment-related deaths were reported.

1.2.6 Immunological Effects

Cabozantinib is a potent inhibitor of multiple RTKs known to play important roles in tumor cell proliferation and/or tumor neovascularization including MET, VEGFR, and RET. In addition, targets of cabozantinib are implicated in promoting tumor immune suppression including TYRO3, MER, and AXL (TAM family kinases). Through preclinical and preliminary clinical evaluation, cabozantinib treatment has been shown to affect tumor cells and the tumor microenvironment in a manner that would potentially make them more sensitive to immune-mediated attack. In vitro and in vivo experiments employing a murine colon carcinoma cell line (MC38-CEA) demonstrated that cabozantinib treatment altered immune modulation and immune subset conditioning (Kwilas et al 2014). Specifically, treatment of tumor cells with cabozantinib in vitro led to increased tumor-cell expression of major histocompatibility complex (MHC) class 1 antigen and greater sensitivity of tumor cells to T-cell-mediated killing. In a mouse MC38-CEA tumor model, cabozantinib treatment led to increased peripheral CD8+ T-cell counts, decreased regulatory T-cells$_{(Tregs)}$ and myeloid-derived suppressor cells (MDSCs), and decreased$_{Treg}$ suppressor activity. Further, synergistic effects including increased CD8+ T-cell infiltration and decreased infiltration by MDSCs and TAMs were observed when a poxviral-based cancer vaccine was administered in addition to cabozantinib in the mouse tumor model.

In the clinical setting, reductions in immunosuppressive-$_{Treg}$ lymphocytes following treatment with cabozantinib were observed in the Phase 2 study of subjects with advanced refractory UC discussed in Section 1.2.3 (Apolo et al 2014). In a Phase 2 study in metastatic triple-negative breast cancer, cabozantinib-treated subjects experienced a persistent increase in the fraction of circulating CD3+T lymphocytes and a persistent decrease in the CD14+ monocytes possibly reflecting activation of systemic antitumor immunity (Tolaney et al 2016).

Together, the preclinical and clinical observations presented above suggest that cabozantinib promotes an immunopermissive environment which might present an opportunity for synergistic effects from combination treatment with PD-1 checkpoint inhibitors.

13 Rationale 13.1 Rationale for the Study and Study Design

Rationale for Treatment Combination:

Through potent inhibition of RTKs including MET, VEGFR, and RET, cabozantinib has demonstrated clinical activity as a single agent across multiple tumor types including advanced UC, RCC, CRPC, and NSCLC. In addition, targets of cabozantinib are implicated in promoting tumor-immune suppression including TYRO3, MER, AXL (TAM family kinases). Preclinical studies (Kwilas et al 2014, Song et al 2015, Lu et al 2017) and clinical observations on circulating immune suppressive cells and immune effector cells (Apolo et al [J Clin Oncol] 2014) suggest that cabozantinib promotes an immune-permissive environment which might present an opportunity for synergistic effects from combination treatment with ICIs which may be independent of tumor PD-L1 expression. Atezolizumab, a potent PD-L1 inhibitor that has also demonstrated clinical activity in multiple tumor types, including advanced UC, RCC, and NSCLC, is an appropriate combination therapy for this evaluation.

Rationale for Dose Escalation Stage:

In the Dose Escalation Stage of the study, an appropriate cabozantinib dose and treatment schedule for the combination of cabozantinib with the standard dosing regimen of atezolizumab will be established in subjects with advanced UC or RCC. This will be achieved through the implementation of a traditional "3 plus 3" dose-escalation study design evaluating three possible cabozantinib dose levels and two possible treatment schedules.

The Dose Escalation Stage has been initiated with the Standard Dosing Schedule. Three subjects have been accrued in Cohort 1 at dose level 1 (cabozantinib 40 mg qd with atezolizumab 1200 mg IV q3w). At the time of the CRC review of Cohort 1, there were no dose-limiting toxicities (DLTs), irAEs, AESIs, or SAEs in the first three subjects; all three subjects had completed the DLT Evaluation Period, and safety follow-up to Cycle 4 was available for the first enrolled subject. The following AEs related to cabozantinib were reported in Cohort 1 (in one subject each): stomatitis, PPE, dyspepsia (each Grade 1); hypertension (Grade 3). The following laboratory abnormalities related to cabozantinib were reported (In one subject each unless otherwise noted): AST increased, lipase increased, hyponatremia, hypoalbuminemia, serum creatinine increased, proteinuria, alkaline phosphatase (ALP) increased (two subjects), absolute neutrophil decreased (each Grade 1); hypophosphatemia (Grade 2). There were no Grade 4 or 5 events. Accrual is continuing in Cohort 2 at dose level 2 (cabozantinib 60 mg qd with atezolizumab 1200 mg IV q3w) and in Cohort 1 with additional 3 subjects at dose level 1.

Rationale for Evaluating Selected Tumor Types:

In the Expansion Stage, eight tumor-specific cohorts in UC, RCC, CRPC, and NSCLC will be enrolled to receive the combination treatment in order to further evaluate the safety and efficacy in these tumor indications on the recommended dose and schedule. The rationale for the planned Expansion Cohorts is based on available single-agent clinical activity and safety of both drugs in these solid tumors. Single-agent activity of cabozantinib has been demonstrated in untreated and pretreated RCC (Choueiri et al 2015; Choueiri et al 2016; Choueiri et al [Clin Oncol] 2017), pretreated UC (Apolo et al [J Clin Oncol] 2016), pretreated CRPC (Smith et al 2013, Smith et al 2014, Basch et al 2015, Smith et al 2016), and NSCLC (Neal et al 2016, Drilon et al 2016, Schöffski et al 2017). Atezolizumab has demonstrated clinical activity as a single agent in platinum-pretreated and cisplatin-ineligible untreated UC (Rosenberg et al 2016; Loriot et al 2016), in pretreated RCC (Bellmunt et al 2016; McDermott et al 2016), as well as in chemotherapy untreated and chemotherapy pretreated NSCLC (Peters et al 2017; Rittmeyer et al 2017; Fehrenbacher et al 2016, Reck et al 2017). In addition, atezolizumab showed encouraging clinical activity in combination with a VEGF-targeting antibody in untreated RCC (Atkins et al 2017).

In addition to exploring cabozantinib in combination with atezolizumab in subjects who had already received standard of care cancer therapy, Expansion Cohorts 1, 3, and 4 will include subjects who are treatment naïve. This is supported by the observed single-agent activity of both cabozantinib and atezolizumab in these tumor indications and the evolving treatment landscape in which ICI therapy is being explored in treatment-naïve and pretreated cancer patients.

Rationale for Expansion Cohort 1:

In Expansion Cohort 1 subjects with advanced untreated RCC will be evaluated. Current treatment guidelines for patients with advanced RCC include VEGFR-targeted agents as initial systemic anticancer therapy (Escudier et al 2016; Sutent [sunitinib] SmPC; Votrient [pazopenib] SmPC). Cabozantinib has been approved in RCC after prior VEGFR-targeted therapy (Choueiri et al 2015; Choueiri et al 2016; Cabometyx [cabozantinib] SmPC). Recently, cabozantinib demonstrated improved clinical outcome compared with sunitinib in untreated patients with clear cell RCC of intermediate- or poor-risk per International Metastatic RCC Database Consortium (IMDC) criteria (Choueiri et al [Clin Oncol]2017; Choueiri et al [Ann Oncol] 2017). Based on these results, cabozantinib has been listed as recommended therapy in untreated RCC of intermediate- and poor-risk (NCCN 2017). In addition, the PD-1 inhibitor nivolumab has been approved as single agent after prior therapy (Opdivo [nivolumab] SmPC), and more recently, the combination of nivolumab and ipilimumab (a CTLA-4 antagonist) demonstrated improved OS compared with sunitinib in untreated RCC patients of intermediate- and poor-prognosis (Escudier et al 2017; NCT02231749). Atezolizumab has also demonstrated preliminary clinical activity as single agent or in combination with the VEGF targeting agent bevacizumab in subjects with advanced RCC (McDermott et al 2016; Atkins et al 2017). In addition, several Phase 3 studies of ICIs in combination with agents targeting CTLA-4 or in combination with VEGF(R)-targeted therapy are ongoing (NCT02231749; NCT02684006; NCT02811861; NCT02853331; NCT02420821; NCT03141177). These clinical observations hold promise for clinical activity of the combination of cabozantinib and atezolizumab in subjects with advanced untreated RCC.

Rationale for Expansion Cohorts 2, 3, 5, and 7:

As discussed above, cabozantinib and atezolizumab have both demonstrated clinical activity as single agents in patients with previously treated advanced UC, RCC, and NSCLC. Evaluation of the combination of the two agents in these patient populations may serve to identify synergistic effects that provide greater clinical benefit to patients. In cohorts 5 (UC) and 7 (NSCLC) enrolling patients who have previously progressed on ICI therapy, the combination of cabozantinib with atezolizumab is used as a strategy to re-sensitize to ICI therapy with the goal to prolong DOR and survival of cancer patients. ICIs are standard of care therapies in both advanced UC and NSCLC in the first-line setting as well the second-line setting (Davarpanah et al 2017, Hanna et al 2017). Depending on the treatment setting, tumor type and PD-L1 expression level, between 20-45% of patients respond initially to single agent ICI therapy. Despite this clinical benefit, a large number of patients become resistant to ICI therapy and develop disease progression. In addition, a subset of patients does not respond and is a priori refractory to ICI therapy (progressive disease [PD] as best response). There is a high unmet need to overcome resistance to ICI therapy. In a recent study enrolling patients with NSCLC, resistance to prior ICI therapy could be reversed by a VEGFR-TKI (sitravatinib) that has a target profile similar to cabozantinib in combination with nivolumab (Leal et al 2017). These observations support the rationale of evaluating the combination cabozantinib and atezolizumab in subjects who have progressed on or after prior ICI therapy in cohorts 5 and 7.

Rationale for Expansion Cohort 4:

In Expansion Cohort 4 subjects with cisplatin-eligible untreated UC will be evaluated. Current treatment guidelines for UC patients include cisplatin-based chemotherapies (Milowsky et al 2017; Witjes et al 2017). However, cisplatin-based therapy is associated with considerable toxicities and therefore only applicable for "fit" patients (Eastern Cooperative Oncology Group [ECOG] 0-1, kidney function with GFR ≥65 mL/min, absence of hearing impairment and peripheral neuropathy [both less than Grade 2 per Common Terminology Criteria for Adverse Events {CTCAE} v4]). In addition, the majority of patients with invasive UC are older than 65 years. The treatment of elderly patients with cisplatin-based chemotherapies is challenging due to the presence of comorbid conditions. In patients who are able to receive first-line cisplatin-based chemotherapy, median survival is approximately 15 months, median PFS is approximately 8 months, and ORR is approximately 50% (von der Maase et al 2000, von der Maase et al 2005). Despite the availability of cisplatin-based combination chemotherapies, the 5-year survival rate is currently only approximately 15% and is less than 10% in patients who present with visceral disease (Sternberg et al 2006; von der Maase et al 2005). This indicates that more effective first line therapies are needed for the treatment of UC. Recently, ICI therapies targeting the PD-1 or PD-L1 signaling pathway of immune cells and tumor cells have demonstrated clinical efficacy, safety, and tolerability in platinum-pretreated and cisplatin ineligible patients with UC (Tecentriq [atezolizumab] SmPC; Keytruda [pembrolizumab] SmPC). In addition, ICIs are currently being evaluated as single agents or as combinations in untreated cisplatin-eligible patients in several Phase 3 studies (NCT02807636, NCT02853305, NCT02516241, NCT03036098). Further, in a Phase 1 study of cabozantinib in combination with the PD-1 inhibitor nivolumab, encouraging clinical activity was observed in subjects with GU tumors (Nadal et al 2017). These clinical observations hold promise for clinical activity of the combination therapy of cabozantinib with atezolizumab in Expansion Cohort 4.

Rationale for Expansion Cohort 6:

In Expansion Cohort 6, subjects with CRPC who have previously received enzalutamide and/or abiraterone acetate and experienced radiographic disease progression in soft tissue will be enrolled. PD-L1 overexpression after exposure to enzalutamide has been associated with immunological anti-tumor response to ICI therapy (Graff et al 2016, Bishop et al 2015). In addition, targeting immune suppressive cells has been suggested as a treatment strategy to further augment anti-tumor immune response in patients with prostate cancer. For example, MET inhibition has been shown to impede neutrophil recruitment to tumors and lymph nodes and this activity potentiates T cell anti-tumor immunity (Glodde et al 2017). Preclinical studies in PTEN/p53 deficient mice treated with cabozantinib showed rapid elimination of invasive prostate cancer through a neutrophil mediated anticancer innate immune response (Patnaik et al 2017). Also, high levels of circulating MDSCs, which are involved in tumor immune evasion (Gabrilovich and Nagaraj 2009), have been associated with PSA levels and metastasis (Vuk-Pavlović et al 2010, Brusa et al 2013, Hossain et al 2015, Idorn at al. 2014). In addition, high levels of immunosuppressive peripheral blood regulatory T cells (Treg) have been identified in patients with prostate cancer and may hamper the anti-tumor response (Miller et al 2010). Combined therapy of cabozantinib and ICIs were demonstrated to be potentially relevant in a preclinical CRPC model, where the combination induced a robust response in both primary and metastatic sites by reducing the immunosuppressive activity of MDSC in the tumor microenvironment (Lu et al 2017). The collective preclinical evidence support the combination of cabozantinib with atezolizumab as a therapeutic strategy for CRPC.

Rationale for Expansion Cohort 8: In Expansion Cohort 8, subjects with advanced Stage IV non-squamous NSCLC without a tumor genetic alteration (EGFR, ALK, ROS1, BRAF V600E) who have not received prior ICI therapy will be enrolled. Current treatment guidelines for this subset of NSCLC patients include single agent pembrolizumab as first-line therapy in patients with high PD-L1 expression (tumor proportion score ≥50%) (Reck et al 2016, Hanna et al 2017). Cabozantinib has demonstrated single-agent activity in unselected pretreated NSCLC subjects with results comparable to second line standard of care chemotherapy (Neal et al 2016; Schöffski et al 2017). Encouraging single-agent activity of cabozantinib has also been demonstrated in untreated and pretreated NSCLC subjects with RET-rearrangement (Drilon at al 2016). Atezolizumab has been approved in chemotherapy-pretreated NSCLC based on improving OS compared with docetaxel (Rittmeyer et al 2017). Clinically meaningful activity of atezolizumab single agent was also demonstrated in unselected untreated NSCLC subjects. For example, OS for atezolizumab-treated patients compared favorably to historical data with combination chemotherapy (23.5 months with atezolizumab vs 1012 months with platinum-based chemotherapy). Objective response rate in untreated and pretreated NSCLC subjects was dependent of PD-L1 status (Peters et al 2017). Preliminary results in patients with GU cancers suggest that the combination of cabozantinib with ICIs may unfold synergistic effects with greater clinical benefit (Nadal at al ESMO 2017). These clinical observations hold promise for clinical activity of the combination therapy of cabozantinib with atezolizumab in NSCLC patients in Expansion Cohort 8. Recently, the combination of atezolizumab/chemotherapy/bevacizumab demonstrated a statistically significant improvement of the co-primary endpoint PFS compared with chemotherapy/bevacizumab. At the time of the PFS analysis, the data of for the co-primary endpoint of OS was not mature (Reck et al 2017)

1.3.2 Rationale for Dosage Selection and Treatment Schedule

In accordance with the US prescribing information, atezolizumab will be administered at a standard dosing regimen of 1200 mg as an IV infusion over 60 min (15 min) every 3 weeks (−2 days) on Day 1 of each 21-day cycle).

In the Dose-Escalation Stage, cabozantinib will be administered orally at dose levels of 20, 40, or 60 mg in escalation cohorts. Sixty (60) mg is the approved tablet dose level for the single-agent treatment of advanced RCC and was also the dose used for the evaluation of cabozantinib as a single agent in the Phase 2 study of subjects with relapsed or refractory metastatic UC. The Dose-Escalation Stage was initiated at the 40 mg cabozantinib dose level in Cohort 1. This dose is consistent with the average daily dose of 41 mg/day received by subjects on the Phase 3 METEOR study in RCC and was also the recommended dose determined for cabozantinib for the clinical evaluation in combination with nivolumab, another antibody inhibitor of the PD-1/PD-L1 pathway (Apolo et al [Ann Oncol]2016). In Cohort 1 no DLT was identified and enrollment in Cohort 2 at 60 mg cabozantinib and extension of Cohort 1 with three additional subjects is ongoing.

The initial cohorts are using the Standard Dosing schedule where cabozantinib and atezolizumab are started on Day 1 of Cycle 1. After the initial Dose Escalation Cohorts on the Standard Dosing Schedule have been evaluated, the Cohort Review Committee (CRC) may choose to enroll additional cohorts of subjects in the Dose Escalation Stage who will receive their first infusion of atezolizumab 21 days after their first dose of cabozantinib (Cabozantinib Run-In Dosing Schedule). The purpose of allowing the implementation of this schedule is to help the CRC assess whether subjects would have improved tolerability to the combination of cabozantinib and atezolizumab if first given the opportunity to optimize their tolerability to cabozantinib alone. The cabozantinib dose levels for those cohorts will be determined by the CRC but will not exceed 60 mg qd.

After all subjects enrolled in the Dose Escalation Stage have completed the DLT Evaluation Period, the CRC will recommend a cabozantinib dose and schedule for the Expansion Stage based on all safety data available. Subjects who enroll in the Dose Expansion Stage will receive that daily dose of cabozantinib as well as 1200 mg IV infusions of atezolizumab every 3 weeks.

1.4 Overall Risk Benefit Assessment

The study will evaluate the safety, tolerability and preliminary activity of cabozantinib in combination with atezolizumab in tumor indications where both agents as single agents have either received regulatory approval or have demonstrated encouraging clinical activity in early clinical stage trials (refer to Sections 1.1.1 and 1.2). In addition, a scientific rationale for a treatment combination of cabozantinib with an ICI has been established in both the preclinical and clinical settings (Kwilas et al 2014, Apolo et al 2014, Tolaney et al 2016). Further, the safety and preliminary clinical activity of cabozantinib in combination with the PD-1 inhibitor nivolumab in ICI-naïve patients has been demonstrated in a Phase 1 study in subjects with GU cancer including metastatic UC and RCC (Nadal et al [Ann Oncol] 2017). Also, in a recent study it has been demonstrated that nivolumab in combination with a TKI with a similar target profile as cabozantinib (inhibiting targets which regulate the immune system), was able to provide clinical benefit in cancer patients who were progressing on ICI therapy (Leal et al 2017). The latter suggests that combining ICI treatment with cabozantinib may result in a tumor micro-environment that is conducive to re-sensitization to ICI treatment after progression which could potentially address an important unmet need as the majority of cancer patients develop resistance and some patients we a priori refractory to ICI therapy.

The safety profiles of both cabozantinib and atezolizumab are well described based on multiple clinical evaluations. However, it is unknown whether the combination of cabozantinib with atezolizumab has a similarly acceptable safety profile as seen with the individual single agents. During the initial standard "3+3" dose escalation stage, a safe dose and dosing schedule of cabozantinib that can be administered in combination with the standard dose of atezolizumab in this study population will be determined by a CRC (Section 12.1). The recommended dose for phase 2 will be evaluated across all eight tumor cohorts in the Expansion Stage. Throughout the study, all enrolled subjects will have to undergo regular safety visits in order to ensure adequate management and reporting of AEs. A Study Oversight Committee will review safety and efficacy data of the Expansion stage and decide upon further expansion of cohort 5 and 7 after the initial 30 subjects have been enrolled (Section 9.1.2 and 12.2). In addition to the CRC, the Sponsor's Executive Safety Committee (ESC; Section 12.3) will review all safety data from subjects in this study. At the date of the CRC review for the first three subjects enrolled in Cohort 1, Cohort 1 (40 mg cabozantinib in combination with 1200 mg atezolizumab) on the Standard Dosing Schedule of the Dose Escalation Stage was completed with a favorable safety profile. Enrollment in Cohort 2 (60 mg cabozantinib dose) and extension of Cohort 1 with additional subjects is currently ongoing.

In order to minimize the safety risks to participating subjects, this protocol has eligibility criteria appropriate to the populations, and includes allowances for dose reductions (cabozantinib) and treatment delays (cabozantinib, atezolizumab). Periodic clinical assessments (physical examination, vital sign, and electrocardiographic assessments) and clinical laboratory tests will monitor for cabozantinib- and atezolizumab-related toxicities. Subjects will also be carefully monitored for AEs potentially related to inhibition of VEGFR by cabozantinib including gastrointestinal (GI) perforation, fistula formation, wound dehiscence, serious bleeding, proteinuria, hypertension, thromboembolic events, osteonecrosis, and reversible posterior leukoencephalopathy syndrome (RPLS) as well as immune-related side effects related to atezolizumab (pneumonitis, hepatitis, colitis, endocrinopathies, skin disorders, ocular events, neurological toxicity, pancreatitis, and infections).

Based on the activity of cabozantinib and atezolizumab as single agents and the demonstrated tolerability of cabozantinib in combination with another ICI (nivolumab), the potential benefit from cabozantinib in combination with atezolizumab appears to outweigh the potential risks in subjects with advanced UC, RCC, CRPC and NSCLC.

2 Study Objectives

Dose-Escalation Stag:

The primary objective is as follows:

To determine the maximum tolerated dose (MT) and/or recommended dose and schedule for the subsequent Expansion Stage of daily oral administration of cabozantinib in subjects with solid tumors when taken in combination with atezolizumab.

The secondary objective is as follows:

To evaluate the plasma PK of daily oral administration of cabozantinib in subjects with solid tumors when given in combination with atezolizumab.

To assess safety for the combination therapy through the evaluation of incidence and severity of nonserious AEs and serious adverse events (SAEs), including irAEs and AESIs.

The exploratory objective is as follows:

Correlation of immune cell, tumor cell, and blood biomarker analyses with clinical outcome Expansion Stage:

The primary objective and endpoint is as follows:

To evaluate preliminary efficacy by estimating the ORR as assessed by the Investigator per RECIST 1.1

The secondary objective is as follows:

To assess safety for the combination therapy through the evaluation of incidence and severity of nonserious AEs and SAEs, including irAEs and AESIs.

The exploratory objectives and endpoints are as follows:

ORR as assessed by the Investigator per modified RECIST for immune response

DOR as assessed by the Investigator per RECIST 1.1

PFS as assessed by the Investigator per RECIST 1.1

Overall survival

Correlation of immune cell, tumor cell, and blood biomarker analyses with clinical outcome Changes in tumor infiltration and/or histology or other molecular changes as determined from optional tumor biopsy To further evaluate the plasma PK of daily oral administration of cabozantinib in subjects with solid tumors when given in combination with atezolizumab For CRPC only: Changes in PSA and evaluation of mismatch repair (MMR) and microsatellite instability (MSI) status.

3 Study Design
3.1 Overview

This is a multicenter, open-label Phase 1b study to assess safety, tolerability, preliminary efficacy, and PK of cabozantinib taken in combination with atezolizumab in subjects with advanced UC, RCC, CRPC, or NSCLC. This study consists of two stages: the Dose Escalation Stage and the Expansion Stage.

3.2 Study Sites

The Dose-Escalation Stage of this study will be conducted at up to S clinical sites in the United States. Additional US and European sites will be added (approximately 50 total sites) for the Expansion Stage.

3.3 Blinding and Randomization

This is an open-label study with treatment arm assignment based upon currently enrolling dose level in the Dose Escalation Stage and by tumor type and prior anticancer therapy in the Expansion Stage. There will be no blinding or randomization in this study.

3.4 Pretreatment Period

Potential subjects will be screened to determine if they meet eligibility criteria. Qualifying screening assessments must be performed within 28 days before first dose of study treatment unless otherwise stated (certain lab values must be obtained closer to first dose; see the schedules of assessment for details [Dose Escalation Stage, Appendix A; Expansion Stage, Appendix B]).

3.5 Treatment Period

Subjects will receive study treatment as long as they continue to experience clinical benefit in the opinion of the investigator or until there is unacceptable toxicity, the need for subsequent systemic anticancer treatment, or until any other reasons for treatment discontinuation listed in the protocol (Section 3.8). Treatment may continue after radiographic progression as long as the investigator believes that the subject is still receiving clinical benefit from study treatment and that the potential benefit of continuing study treatment outweighs potential risk. Clinical judgment should be used for allowing treatment beyond radiographic progression. Subjects with clinically significant symptomatic deterioration at the time of radiographic progression may not be suitable for further treatment. The possibility of a delayed anti-tumor immune response should be taken into consideration: mixed responses with decreasing and increasing tumor lesion sis at the same imaging time point or the appearance of new lesions prior to achieving a radiological response have been reported with ICI. Discontinuation of one component of the combination study treatment while continuing to receive the other may be allowed with Sponsor notification.

All enrolled subjects will be treated with best supportive care while on study treatment. This excludes systemic nonprotocol anticancer therapy, which requires study treatment to be discontinued. Permitted study drug modifications to manage AEs will comprise dose reductions (from 60 mg to 40 mg daily, from 40 mg to 20 mg daily, or from 20 mg daily to 20 mg every other day [qod]) or interruptions for cabozantinib and dose delays for atezolizumab.

3.5.1 Dose Escalation Stage

The primary objective of the Dose Escalation Stage is to determine the MTD and/or the recommended Expansion Stage dose and schedule for cabozantinib when taken in combination with a standard dosing regimen of atezolizumab (1200 mg infusion, once every 3 weeks).

Three cabozantinib tablet daily dose levels will be considered for evaluation: 20 mg, 40 mg, and 60 mg. Atezolizumab will be administered as a 1200 mg infusion once every 3 weeks (Table 3-1).

The DLT Evaluation Period is defined as the 21 days following administration of the first dose of atezolizumab. Subjects will accrue in escalation cohorts of 3-6 subjects using a "3 plus 3" design, and dosing will begin at the 40 mg dose level of cabozantinib. Subjects with either advanced UC or RCC will be eligible for these cohorts, and cohorts may comprise mixtures of subjects with those tumor types. During this stage, the decision to open a new cohort will be made by the CRC when all subjects in the current cohort have completed the DLT Evaluation Period. Cohort enrollment decisions will depend largely upon DLT reporting for subjects through the DLT Evaluation Period, but all available safety and PK data will be considered in a decision to dose escalate or de-escalate the next cohort or expand the current cohort. Dose escalation/de-escalation decision rules based on DLTs are provided in Table 3-2, and DLT definitions are provided in Section 3.5.1.4. A subject who is withdrawn from the study for failing to receive the first dose of atezolizumab or at least 75% of the mandated doses of cabozantinib during the DLT Evaluation Period for reasons other than safety (eg, withdrawal of consent, noncompliance, disease progression, or AEs assessed as not related to study treatment) may be replaced.

TABLE 3-1

Dosing Combinations for Potential Evaluation during the Dose-Escalation Stage

| Relative Dose Level | Cabozantinib | Atezolizumab |
| --- | --- | --- |
| 2 | 60 mg oral qd | 1200 mg IV q3w |
| 1 | 40 mg oral qd | 1200 mg IV q3w |
| −1 | 20 mg oral qd | 1200 mg IV q3w |

IV, intravenous;
qd, once daily;
q3w, once every three weeks

TABLE 3-2

Dose Escalation Stage Decision Rules

| Number of Subjects per Cohort with DLTs in Current Cohort | Dose Escalation Decision Rule |
| --- | --- |
| 0 out of 3 | Enter three subjects at the next higher dose level. If the current dose level was not at the protocol-defined maximum cabozantinib dose (60 mg), the CRC may decide to enroll an additional three subjects at the current dose level in parallel. If the current cohort was treated at the protocol defined maximum cabozantinib dose (60 mg), enter an additional three subjects at that dose level. |
| 0 out of 6 | Hold further enrollment at the current dose level. |
| 1 out of 3 | Enter three more subjects at the current dose level. |

TABLE 3-2-continued

Dose Escalation Stage Decision Rules

| Number of Subjects per Cohort with DLTs in Current Cohort | Dose Escalation Decision Rule |
|---|---|
| 1 out of 6 | Enter three subjects at the next higher dose level unless evaluation of that dose level is already complete. If current cohort was treated at the protocol defined maximum cabozantinib dose level (60 mg), hold further enrollment in the Dose Escalation Stage. |
| ≥2 out of 3 or 6 | Enter three additional subjects at the next lower dose level unless six subjects have already been treated at that level. If the current cohort was treated at the protocol-defined minimum cabozantinib dose level (20 mg), hold further enrollment in the Dose Escalation Stage. |

CRC, Cohort Review Committee;
DLT, dose-limiting toxicity.

An MTD of cabozantinib will be defined as the highest evaluated dose level at which not more than 1 out of 6 subjects experience a DLT. As cabozantinib dose levels above 60 mg will not be evaluated, an MTD for cabozantinib may not be reached. The recommended dose for the Expansion Stage will be determined by the CRC based on DLTs observed during the DLT Evaluation Period and other relevant safety information.

Subjects in the Dose Escalation Stage may continue to receive study treatment after completing the DLT Evaluation Period. The CRC will evaluate safety and PK data collected during and after the DLT Evaluation Period to make informed decisions on cohort enrollment, dose escalation/de-escalation, and MT or recommended dose and schedule determination.

3.5.1.1 Dosing Schedules

Subjects in the Dose Escalation Stage will receive study treatment on one of two dosing schedules: the Standard Dosing Schedule or the Cabozantinib Run-In Dosing Schedule. Initial Dose Escalation Stage cohorts will follow the Standard Dosing Schedule. Additional Dose Escalation Stage cohorts following the Cabozantinib Run-In Dosing Schedule may be implemented upon request of the CRC if no recommended Expansion Stage dose is identified after the evaluation of the Standard Dosing Schedule. The same cabozantinib dose levels will apply to the Cabozantinib Run-In Dosing Schedule as for the Standard Dosing Schedule (Table 3-1).

3.5.1.2 Standard Dosing Schedule

Initial dose escalation cohorts will receive the combination regimen on a "Standard Dosing Schedule" with the first infusion of atezolizumab given on the same day as the first dose of cabozantinib (on C1D1).

3.5.1.3 Cabozantinib Run-In Dosing Schedule

If review of safety data for all enrolled subjects who received the Standard Dosing Schedule does not yield a recommended dose for the Expansion Stage, the CRC may decide to enroll additional cohorts of subjects in the Dose Escalation Stage treated on a "Cabozantinib Run-In Dosing Schedule." Subjects in these cohorts will initiate treatment with cabozantinib on C1D1 and would receive their first infusion of atezolizumab 21 days later on Cycle 2 Day 1 (C2D1). The subjects would only be evaluated for DLTs in the 21-day period after receiving the first infusion of atezolizumab (the DLT Evaluation Period). These cohorts would be enrolled according to the "3+3" strategy described above, but the CRC may also include additional subjects at one or more dose levels in order to ensure enough subjects reach the DLT Evaluation Period while still receiving the assigned cohort dose (ie, experienced no dose reductions in the Cabozantinib Run-In Dosing Schedule). Administration of the first dose of atezolizumab is not to occur while cabozantinib treatment is interrupted; the start of Cycle 2 is to be delayed until after cabozantinib treatment has resumed, is well-tolerated, and the investigator determines that atezolizumab can be administered safely. Subjects who discontinue cabozantinib treatment during Cycle 1 on the Cabozantinib Run-In Dosing Schedule will not be eligible to receive atezolizumab on study.

The purpose of this dosing schedule is to help the CRC assess whether subjects would have improved tolerability to the combination of cabozantinib and atezolizumab if first given the opportunity to optimize their tolerability to cabozantinib alone during a three week run-in period. The CRC will consider safety data from all Dose Escalation cohorts when determining the recommended Expansion Stage dose and schedule.

3.5.1.4 Dose-Limiting Toxicities

Dose-limiting toxicities will be determined by the CRC upon review of all available cohort data and are defined as any of the following occurring during the DLT Evaluation Period:

1. Any related AE that in the opinion of the CRC is of potential clinical significance such that further dose escalation of cabozantinib would expose subjects to unacceptable risk.
2. Any related ? Grade 3 AE which is unexpected in severity and/or duration compared with the known safety profiles of cabozantinib and atezolizumab when used as single agents, and that cannot be managed by dose modification (reduction or interruption), and adequate supportive care and requires permanent discontinuation of cabozantinib and/or atezolizumab.
3. Inability to take ? 75% of the planned cabozantinib dose during the DLT Evaluation Period because of a treatment-related AE Examples of AEs which will not be considered DLTs:

Transient infusion-related AEs which can be controlled with medical management (ie, flu-like symptoms, fever)

Tumor flare-related AEs (ie, localized pain, irritation at tumor sites)

Any Grade 3 AE (regardless of relationship to study treatment) which the CRC determines is unlikely to compromise the subject's safety and resolves to ≤Grade 1 or is controlled with adequate supportive care including short dose delays or dose reductions. These could include events that are expected to occur with single-agent therapy with cabozantinib or atezolizumab [ie, hypertension, skin toxicity, headache, nausea, fatigue, emesis, diarrhea].

Single laboratory values that are out of normal range and unlikely to be related to study treatment and do not have any clinical correlate.

3.5.2 Expansion Stag

Once the CRC identifies the recommended dose and schedule of cabozantinib in combination with atezolizumab, the study will enter the Expansion Stage. In this stage, eight expansion cohorts in subjects with advanced UC, RCC, CRPC, and NSCLC will be enrolled to obtain additional efficacy safety, PK, and pharmacodynamic data at the recommended dose and schedule (the Standard Dosing Schedule or the Cabozantinib Run-In Dosing Schedule). An abbreviated description of the Expansion Cohorts 1-8 is provided in Table 3-3.

3.6 Post-Treatment Period and Survival Follow-Up

The final safety assessment will occur at the Post-Treatment Follow-Up Visit 30 (+14) days after the date of the decision to discontinue treatment. If a subject is experiencing an SAE, AESI, or Grade 3 or 4 AE or at the time of that visit, the subject will continue to be followed until the AE has resolved, the AE has improved to Grade 2 or lower, or the investigator determines that the event has become stable or irreversible. During the Post-Treatment Period, each subject will continue to be followed for survival. The investigator (or designee) will make contact with the subject at least as frequently as every 12 weeks (t 7 days) after the Post-Treatment Follow-Up Visit, until the subject expires or the Sponsor decides to discontinue collection of these data for the study.

3.7 Maintenance Phase

When sufficient data have been collected to adequately evaluate all study endpoints, and upon site notification by the Sponsor, subjects remaining on study treatment will enter the study Maintenance Phase. In the Maintenance Phase subjects will continue to receive study treatment until

TABLE 3-3

Summary of Expansion Stage Cohorts

| Cohort | Tumor Type (Histology) | Abbreviated eligibility description | Initial Cohort Size (n) | Potential Additional Enrollment (n) |
|---|---|---|---|---|
| 1 | RCC (clear cell) | No prior systemic anticancer therapy | 30 | — |
| 2 | UC (transitional cell) | Prior platinum-containing chemotherapy | 30 | — |
| 3 | UC (transitional cell) | Cisplatin-ineligible but no prior systemic anticancer therapy | 30 | — |
| 4 | UC (transitional cell) | Cisplatin-eligible but no prior systemic anticancer therapy | 30 | — |
| 5 | UC (transitional cell) | Prior immune checkpoint inhibitor therapy | 30 | 50 |
| 6 | CRPC (adeno) | Prior enzalutamide and/or abiraterone therapy | 30 | — |
| 7 | NSCLC (non-squamous) | Prior immune checkpoint inhibitor therapy | 30 | 50 |
| 8 | NSCLC (non-squamous) | No prior immune checkpoint inhibitor therapy | 30 | — |
|  |  | Total enrollment | 240 | 340 |

All Expansion cohorts will initially enroll 30 subjects. Because of the high unmet need of patients who have progressed on prior ICI therapy, the Study Oversight Committee (Section 12.2) of the study may decide after reviewing data of Expansion Cohorts 5 and 7 to allow for additional enrollment of each 50 subjects to further assess the clinical activity and safety of cabozantinib in combination with atezolizumab following ICI progression (Section 9.1.2). All subjects enrolled in the Expansion Cohort will be following the same schedule of assessments and dosing instructions. For more detail regarding the eligibility of subjects for this study refer to inclusion and exclusion criteria (Section 4.2 and 4.3). Rationales for enrollment in each Expansion Cohort are provided in Section 1.3.1.

Only one dose level and dosing schedule will be evaluated in the Expansion Stage: the Standard Dosing Schedule (Section 3.5.1.2) or the Cabozantinib Run-In Dosing Schedule (Section 3.5.1.3). If the Cabozantinib Run-In Dosing Schedule is the CRC-selected dosing schedule for the Expansion Stage, subjects who discontinue cabozantinib treatment during Cycle 1 will not be eligible to receive atezolizumab on study.

a protocol-defined criterion for discontinuation has been met. With Sponsor notification, subjects may be allowed to discontinue one component of the study treatment but continue to receive the other. After implementation of the Maintenance Phase, the study will be considered complete at sites and in countries that no longer have active subjects.

In the Maintenance Phan, subjects are to undergo periodic safety assessments (including local laboratory tests) and tumor assessments; the nature and frequency of these assessments are to be performed per standard of care if allowed by local regulations. It is the Investigator's responsibility to ensure that subject visits occur frequently enough and adequate assessments are performed to ensure subject safety. In order to continue to collect important safety information on subjects still enrolled in the study, reporting of SAEs; AEs (including irAEs), whether serious or not, leading to dose modifications or treatment discontinuation; AESIs; and other reportable events (pregnancy and medication errors with sequelae) is to continue per protocol requirements specific to the Maintenance Phase (Section 5.4).

Assessments in the Post-Treatment Period (including the post-treatment follow-up visit) are not required for subjects who discontinue study treatment in the Maintenance Phase (such subjects are to be followed per standard of care). Further details are available in Appendix C.

3.8 Treatment Discontinuation and Withdrawals

Subjects may discontinue study treatment and assessments or withdraw their consent to participate in the study at any time without prejudice. When subjects withdraw consent, all study treatments will be stopped. The investigator may withdraw a subject from study treatment or from the study if, in his or her clinical judgment, it is in the best interest of the subject or if the subject cannot comply with the protocol. The investigator will also withdraw a subject from study treatment or from the study upon the Sponsor's request or if the Sponsor chooses to terminate the study.

In addition, any of the following conditions require withdrawal of the subject from study treatment:

Subject no longer experiences clinical benefit as determined by the investigator (eg, clinical deterioration attributable to disease progression and unlikely to reverse with continued study treatment and/or supportive care).

Unacceptable side effects the investigator feels may be due to combination study treatment. However, discontinuation of one component of the combination study treatment while continuing to receive the other may be allowed with Sponsor notification in an effort to manage such side effects in subjects experiencing clinical benefit.

The investigator feels it is not in the best interest of the subject to continue on study.

Subject participation in another clinical study using an investigational agent, investigational medical device, or other intervention.

Necessity for treatment with nonprotocol systemic anticancer therapy.

Necessity for interrupting either study drug for greater than 12 weeks for study-treatment related AEs unless approved by the Sponsor.

Refusal of sexually active fertile subjects (excluding subjects who have been sterilized) to use medically accepted methods of contraception.

Female subjects who become pregnant.

Subject request to discontinue study treatment (with or without concurrent withdrawal of informed consent).

Significant noncompliance with the protocol schedule in the opinion of the investigator or the Sponsor.

The Sponsor should be notified of all subject study treatment discontinuations and study withdrawals as soon as possible. The reason for discontinuation or withdrawal will be documented.

For subjects who discontinue study treatment, every effort must be made to undertake protocol-specified follow-up procedures including end-of-treatment assessments, survival follow-up, and subsequent anticancer treatment unless consent to participate in the study is also withdrawn.

If a subject fails to return for the protocol-defined visits, an effort must be made to determine the reason. If the subject cannot be reached by telephone, at the minimum a registered letter should be sent to the subject (or the subject's legal guardian) requesting contact with the clinic.

If a subject is discontinued from study treatment because of an AE (including irAE) considered to be related to study treatment and the event is ongoing 30 days after the last dose of study treatment, the event must be followed until resolution or determination by the investigator that the event has become stable or irreversible.

If a subject withdraws consent to participate in the study, no further study procedures or assessments will be performed and no further study data will be collected for this subject other than the determination of survival status for subjects enrolled in the Expansion Stage. This information may be obtained from public records such as government vital statistics or obituaries, as permitted by local law.

3.9 Subject Replacements

Only subjects who sign the informed consent and receive any study treatment will be considered enrolled.

During the Dose-Escalation Stage, if an enrolled subject fails to receive the first dose of atezolizumab or at least 75% of the mandated doses of cabozantinib during the DLT Evaluation Period for reasons other than safety (eg, withdrawal of consent, noncompliance, disease progression, or AEs assessed as not related to study treatment), he or she will be replaced (ie, an additional subject will be added to the cohort). In addition, subjects on the Cabozantinib Run-In Dosing Schedule who discontinue study treatment for any reason (including safety) prior to receiving their first dose of atezolizumab will be replaced. Subjects who receive atezolizumab but fail to complete DLT Evaluation Period because of an AE related to study treatment will not be replaced. Subjects who are replaced with new subjects will not be considered in making dose escalation decisions, but if possible will be followed for safety and other assessments.

Subjects enrolled in the Expansion Stage will not be replaced.

4 Study Population 4.1 Target Population

This study will enroll subjects with advanced RCC or UC. The precise populations with these tumor types will vary slightly between the Dose Escalation Stage and the Expansion Stage based on prior treatment. Eligibility criteria for this study have been carefully considered to ensure the safety of the study subjects and to safeguard the integrity of the study results. It is imperative that subjects fully meet all inclusion criteria and none of the exclusion criteria. The Sponsor will not grant waivers to study eligibility criteria.

4.2 Inclusion Criteria

A subject must meet all of the following criteria to be eligible for the study:

1. Cytologically or histologically and radiologically confirmed solid tumor that is inoperable locally advanced, metastatic, or recurrent:

Dose-Escalation Stage:
   a. Subjects with UC (including renal pelvis, ureter, urinary bladder, urethra) after prior platinum-based therapy, or
   b. Subjects with RCC (clear cell, non-clear cell histology) with or without prior systemic anticancer therapy Expansion Stage:
   c. Expansion Cohort 1: Subjects with RCC with clear cell histology (including those with mixed sarcomatoid component) and without prior systemic anticancer therapy
   d. Expansion Cohort 2: Subjects with UC with transitional cell histology (including renal pelvis, ureter, urinary bladder, urethra) who have radiographically progressed on or after platinum-containing chemotherapy including subjects who received prior neoadjuvant or adjuvant platinum-containing therapy with disease recurrence <12 months from the end of last therapy
   e. Expansion Cohort 3: Subjects with UC with transitional cell histology (including renal pelvis, ureter, urinary bladder, urethra) who are ineligible for cisplatin-based chemotherapy and have not received prior systemic anticancer therapy for inoperable locally advanced or metastatic disease Ineligible for cisplatin-based chemotherapy is defined by meeting one of the following criteria:

Impaired renal function (glomerular filtration rate [GFR]>30 mL/min/1.73 m2 and <60 mL/min/1.73 m2), hearing loss of ? 25 dB at two contiguous frequencies, or ? Grade 2 peripheral neuropathy per CTCAE v4.

Prior neoadjuvant or adjuvant platinum-based chemotherapy is allowed if disease recurrence took place >12 months from end of last therapy.

f. Expansion Cohort 4: Subjects with UC with transitional cell histology (including renal pelvis, ureter, urinary bladder, urethra) eligible for cisplatin-based chemotherapy and have not received prior systemic anticancer therapy for inoperable locally advanced or metastatic disease.

Prior neoadjuvant or adjuvant platinum-based chemotherapy is allowed if disease recurrence took place >12 months from end of last therapy.

g. Expansion Cohort 5: Subjects with UC with transitional cell histology (including renal pelvis, ureter, urinary bladder, urethra) who have radiographically progressed on or after one prior immune checkpoint inhibitor (anti-PD-1 or anti-PD-L1) as the most recent therapy for the treatment of inoperable locally advanced or metastatic disease.

Allowed are up to 2 lines of prior systemic anticancer therapy to treat locally advanced or metastatic UC including prior treatment with an anti-CTLA-4 agent.

Excluded are subjects who had a prior combination therapy of an immune checkpoint inhibitor (anti-PD-1 or anti-PD-L1) with a VEGFR-targeting TKI.

h. Expansion Cohort 6: Subjects with metastatic CRPC (adenocarcinoma of the prostate without neuroendocrine differentiation or small cell features) who have radiographically progressed in soft tissue on or after enzalutamide and/or abiraterone acetate for metastatic disease.

(Note: PSA progression or bone progression alone are not allowed to determine eligibility).

Prior chemotherapy is not allowed with the exception of docetaxel given in combination with androgen deprivation therapy (ADT) for progressive castration-nave disease prior to treatment with enzalutamide and/or abiraterone acetate.

Prior radium Ra 223 dichloride is not allowed.

Subject must have castrate-level testosterone (<50 ng/dL [<2 nM]) following bilateral orchiectomy or by ongoing androgen deprivation therapy with a gonadotropin-releasing hormone (GnRH) analog that was initiated ≥4 weeks prior to first dose of study treatment and must be continued throughout the study.

i. Expansion Cohort 7: Subjects with Stage IV non-squamous NSCLC who have radiographically progressed on or after prior immune checkpoint inhibitor (anti-PD-1 or anti-PD-L1) as the most recent therapy for the treatment of metastatic disease.

Allowed are up to 2 lines of prior systemic anticancer therapy to treat metastatic NSCLC including prior treatment with an anti-CTLA-4 agent.

Excluded are subjects who had a prior combination therapy of an immune checkpoint inhibitor (anti-PD-1 or anti-PD-1) with a VEGFR-targeting TKI, and subjects who have been diagnosed with an EGFR mutation, ALK translocation, ROS1 rearrangement, or BRAF V600E mutation.

j. Expansion Cohort 8: Subjects with Stage IV non-squamous NSCLC who have not received prior immune checkpoint inhibitor therapy (anti-PD-1 or anti-PD-L1).

One line of prior systemic anticancer therapy to treat metastatic NSCLC is allowed.

Excluded are subjects who have been diagnosed with an EGFR mutation, ALK translocation, ROS1 rearrangement, or BRAF V600E mutation.

2. Measurable disease per RECIST 1.1 as determined by the investigator. Measurable disease must be outside the radiation field if prior radiation therapy was administered.

3. Tumor tissue material available (archival or recent tumor biopsy)

4. Recovery to baseline or ≤Grade 1 CTCAE v4 from toxicities related to any prior treatments, unless AE(s) are clinically nonsignificant and/or stable on supportive therapy.

5. Age eighteen years or older on the day of consent.

6. ECOG Performance Status of 0 or 1.

7. Adequate organ and marrow function, based upon meeting all of the following laboratory criteria within 14 days before first dose of study treatment:

a. Absolute neutrophil count (ANC)≥1500/mm3 (≥1.5 GI/L) without granulocyte colony-stimulating factor support within 2 weeks before screening laboratory sample collection.

b. White blood cell count ≥2500/mm3 (≥2.5 GI/L).

c. Platelets ≥100,000/mm3 (≥100 GI/L) without transfusion within 2 weeks before screening laboratory sample collection.

d. Hemoglobin ≥9 g/dL (≥90 g/L) without transfusion within 2 weeks before screening laboratory sample collection.

e. ALT, AST, and ALP <3× upper limit of normal (ULN). ALP <5× ULN with documented bone metastases.

f. Total bilirubin <1.5×ULN (for subjects with Gilbert's disease <3×ULN).

g. Serum creatinine <2.0×ULN or calculated creatinine clearance 30 mL/min (0.5 mL/sec) using the Cockcroft-Gault equation (see Table 5-2 for Cockcroft-Gault formula).

h. Urine protein/creatinine ratio (UPCR)<1 mg/mg (<113.2 mg/mmol) for subjects with RCC, CRPC, or NSCLC and <2 mg/mg (<226.4 mg/mmol) creatinine for subjects with UC.

8. Capable of understanding and complying with the protocol requirements and must have signed the informed consent document.

9. Sexually active fertile subjects and their partners must agree to use medically accepted methods of contraception (eg, barrier methods, including male condom, female condom, or diaphragm with spermicidal gel) during the course of the study and for 5 months after the last dose of study treatment.

10. Female subjects of childbearing potential must not be pregnant at screening. Females of childbearing potential are defined as premenopausal females capable of becoming pregnant (ie, females who have had any evidence of menses in the past 12 months, with the exception of those who had prior hysterectomy). However, women who have been amenorrheic for 12 or more months are still considered to be of childbearing potential if the amenorrhea is possibly due to prior chemotherapy, antiestrogens, low body weight, ovarian suppression or other reasons.

4.3 Exclusion Criteria

A subject who meets any of the following criteria is ineligible for the study:

1. Prior treatment with cabozantinib or ICIs including anti-CTLA-4, anti-PD-1, anti-PD-L1, anti-PD-L2, anti-OX-40, anti-CD137 therapy except for Expansion Cohorts 5 and 7 in which prior anti-PD-1 or anti-PD-L1 therapy is required for eligibility (see Inclusion Criteria 1g and 1i, respectively, for details).
2. Receipt of any type of small molecule kinase inhibitor (including investigational kinase inhibitor) within 2 weeks before first dose of study treatment.
3. For CRPC subjects: receipt of flutamide or nilutamide within 4 weeks or bicalutamide within 6 weeks before first dose of study treatment.
4. Receipt of any type of anticancer antibody (including investigational antibody) or systemic chemotherapy within 4 weeks before first dose of study treatment, except in Expansion Cohorts 5 and 7 for which receipt of a PD-1, PD-L1, or CTLA-4 targeting antibody is permitted within 4 weeks before first dose of study treatment.
5. Radiation therapy for bone metastasis within 2 weeks, any other radiation therapy within 4 weeks before first dose of study treatment. Subjects with clinically relevant ongoing complications from prior radiation therapy are not eligible.
6. Known brain metastases or cranial epidural disease unless adequately treated with radiotherapy and/or surgery (including radiosurgery) and stable for at least 4 weeks before first dose of study treatment. Eligible subjects must be neurologically asymptomatic and without corticosteroid treatment at the time of first dose of study treatment.
7. Concomitant anticoagulation with oral anticoagulants (eg, warfarin, direct thrombin and Factor Xa inhibitors) or platelet inhibitors (eg, clopidogrel). Allowed anticoagulants are the following:
   a. Low-dose aspirin for cardioprotection (per local applicable guidelines) and low-dose low molecular weight heparins (LMWH).
   b. Anticoagulation with therapeutic doses of LMWH in subjects without known brain metastases who are on a stable dose of LMWH for at least 6 weeks before first dose of study treatment, and who have had no clinically significant hemorrhagic complications from the anticoagulation regimen or the tumor.
8. Diagnosis of immunodeficiency or is receiving systemic steroid therapy or any other form of immunosuppressive therapy within 2 weeks prior to first dose of study treatment. Inhaled and topical corticosteroids and mineralocorticoids are allowed.
9. Administration of a live, attenuated vaccine within 30 days before first dose of study treatment.
10. The subject has uncontrolled, significant intercurrent or recent illness including, but not limited to, the following conditions:
    a. Cardiovascular disorders:
       i. Congestive heart failure New York Heart Association Class 3 or 4, unstable angina pectoris, serious cardiac arrhythmias.
       ii. Uncontrolled hypertension defined as sustained blood pressure (BP) >150 mm Hg systolic or >100 mm Hg diastolic despite optimal antihypertensive treatment.
       iii. Stroke (including transient ischemic attack [TIA]), myocardial infarction (MI), or other ischemic event, or thromboembolic event (eg, deep venous thrombosis [DVT], pulmonary embolism) within 6 months before first dose. Subjects with a diagnosis of DVT within 6 months are allowed if stable, asymptomatic, and treated with LMWH for at least 6 weeks before first dose.
    b. Gastrointestinal (GI) disorders including those associated with a high risk of perforation or fistula formation:
       i. Tumors invading the GI-tract, active peptic ulcer disease, inflammatory bowel disease, diverticulitis, cholecystitis, symptomatic cholangitis or appendicitis, acute pancreatitis or acute obstruction of the pancreatic or biliary duct, or gastric outlet obstruction.
       ii. Abdominal fistula, 01 perforation, bowel obstruction, or intra-abdominal abscess within 6 months before first dose. Note: Complete healing of an intra-abdominal abscess must be confirmed before first dose.
    c. Clinically significant hematuria, hematemesis, or hemoptysis of >0.5 teaspoon (2.5 mL) of red blood, or other history of significant bleeding (eg, pulmonary hemorrhage) within 12 weeks before first dose.
    d. Cavitating pulmonary lesion(s) or known endobronchial disease manifestation.
    e. Lesions invading major pulmonary blood vessels.
    f. Other clinically significant disorders such as:
       i. Active or history of autoimmune disease or immune deficiency, including, but not limited to, myasthenia gravis, myositis, autoimmune hepatitis, systemic lupus erythematosus, rheumatoid arthritis, psoriatic arthritis, inflammatory bowel disease, antiphospholipid antibody syndrome, Wegener granulomatosis, Sjögren's syndrome, Guillain-Barré syndrome, or multiple sclerosis (see Appendix D for a more comprehensive list of autoimmune diseases and immune deficiencies). Subjects with the following conditions are eligible for the study:
          A history of autoimmune-related hypothyroidism and on thyroid replacement hormone
          Controlled Type 1 diabetes mellitus and on an insulin regimen
          Asthma that require intermittent use of bronchodilators
          Eczema, psoriasis, lichen simplex chronicus, or vitiligo with dermatologic manifestations only provided all of following we true:
          Rash covers <10% of body surface area
          Disease is well controlled at baseline and requires only low-potency topical corticosteroids
          No occurrence of acute exacerbations of the underlying condition requiring psoralen plus ultraviolet A radiation, methotrexate, retinoids, biologic agents, oral calcineurin inhibitors, or high potency or oral corticosteroids within the previous 12 months
       ii. Active infection requiring systemic treatment, infection with human immunodeficiency virus (HIV) or acquired immunodeficiency syndrome (AIDS)-related illness, or acute or chronic hepatitis B or C infection, or positive test for tuberculosis.

iii. History of idiopathic pulmonary fibrosis, organizing pneumonia (eg, bronchiolitis obliterans), drug-induced pneumonitis, idiopathic pneumonitis, or evidence of active pneumonitis on screening chest computerized tomography (CT) scan. History of radiation pneumonitis in the radiation field (fibrosis) is permitted.

iv. Serious non-healing wound/ulcer/bone fracture.

v. Malabsorption syndrome.

vi. Uncompensated/symptomatic hypothyroidism.

vii. Moderate to severe hepatic impairment (Child-Pugh B or C).

viii. Requirement for hemodialysis or peritoneal dialysis.

ix. History of solid organ or allogenic stem cell transplant.

11. Major surgery (eg, GI surgery, removal or biopsy of brain metastasis) within 8 weeks before first dose of study treatment, except prior nephrectomy within 6 weeks before first dose. Complete wound healing from major surgery must have occurred 3 weeks before first dose and from minor surgery (eg, simple excision, tooth extraction) at least 10 days before first dose. Subjects with clinically relevant ongoing complications from prior surgery are not eligible.

12. Corrected QT interval calculated by the Fridericia formula (QTcF)>500 ms per electrocardiogram (ECG) within 28 days before first dose of study treatment (see Section 5.6.4 for Fridericia formula).

Note: fa single ECG shows a QTcF with an absolute value >500 ms two additional ECGs at intervals of approximately 3 min must be performed within 30 min after the initial ECG, and the average of these three consecutive results for QTcF will be used to determine eligibility.

13. Pregnant or lactating females.

14. Inability to swallow tablets.

15. Previously identified allergy or hypersensitivity to components of the study treatment formulations.

16. Diagnosis of another malignancy within 2 years before first dose of study treatment, except for superficial skin cancers, or localized, low grade tumors deemed cured and not treated with systemic therapy. Incidentally diagnosed prostate cancer is allowed in UC subjects if assessed as stage ≤T2N0M0, Gleason score ≤6, and PSA undetectable.

5 Study Assessments and Procedures

The study assessment schedules are presented in Appendix A for the Dose Escalation Stage and in Appendix B for the Expansion Stage.

Most study assessments and procedures (including treatment administration) will be performed in cycles. Cycle 1 Day 1 (C1D1) is defined as the date of first dose of any study treatment. A cycle is generally the 21-day interval starting with the date of an atezolizumab infusion and ending with the day before the next atezolizumab infusion. However, under some circumstances no atezolizumab may be dosed during a cycle:

If the Cabozantinib Run-In Dosing Schedule is employed, the period in which cabozantinib is administered prior to the first dose of atezolizumab will be defined as Cycle 1.

If atezolizumab treatment is discontinued but cabozantinib treatment is allowed to continue with the notification of the Sponsor, each consecutive 21-day interval starting with the date of the decision to discontinue atezolizumab will be defined as a cycle. If the decision to discontinue atezolizumab occurs less than 21 days after the last infusion, then the next cycle will begin on the $22^{nd}$ day ater the last infusion.

Cycles may extend beyond 21 days if atezolizumab dosing is delayed. During an atezolizumab dose delay, subjects should return to the site for scheduled safety visits every three weeks from the last dose of atezolizumab. Further, the study site should perform unscheduled visits weekly (or more frequently as clinically indicated) to monitor subject safety and appropriateness for re-treatment with study treatment.

Imaging assessments (CT, magnetic resonance imaging [MRI], bone scan) are to be performed at protocol-defined intervals based the first dose of study treatment (defined as Week 1 Day 1 [W1D1]); all subsequent time points for these assessments will apply the same nomenclature, which will not be modified as a result of modifications or discontinuations of treatment administration. The frequencies of imaging assessments are provided in Appendix A for the Dose Escalation Stage and in Appendix B for the Expansion Stage.

Unless otherwise indicated, in the absence of toxicity all scheduled visits will occur within windows for the protocol-specified visit schedule. If the subject experiences toxicity, study treatment can be modified or delayed as described in Section 6.5. If the subject is unable to have a study assessment taken within the defined time window due to an event outside of his or her control (eg, clinic closure, personal emergency, inclement weather, vacation), the assessment should be performed as close as possible to the required schedule. Laboratory panels for serum chemistry, hematology, and urinalysis are defined in Section 5.6.5.

5.1 Pretreatment Period

Informed consent must be obtained prior to initiation of any clinical screening procedure that is performed solely for the purpose of determining eligibility for research; however, evaluations performed as part of routine care prior to informed consent can be utilized as screening evaluations if permitted by the site's Institutional Review Board (IRB)/Ethics Committee (EC) policies. Informed consent may be obtained greater than 28 days before first dose of study treatment. At informed consent, subjects will be assigned a subject identifier; subject identifiers are not to be re-assigned if a subject is determined to be ineligible, and subjects are to maintain their original identifier if re-screening is required or if the subject experiences a change in study site or investigator.

To determine subject eligibility as stipulated in Section 4, subjects will undergo required screening evaluations as outlined in Appendix A (Dose Escalation Stage) and Appendix B (Expansion Stage) and as described in Section 5.6. Qualifying screening assessments must be performed within 28 days before the first dose of study treatment unless otherwise stated (certain lab values must be obtained closer to first dose of study treatment). Eligibility criteria based on laboratory values will use the central laboratory result (except serum pregnancy test and 24-hour urine protein; see Section 5.6.5). Local laboratory assessments may be obtained and used if the results are required by the investigator in a rapid timeframe to confirm eligibility. Local laboratory results used for confirmation of eligibility must be forwarded to the local laboratory management vendor.

Study eligibility is based on a subject meeting all of the study inclusion criteria and none of the exclusion criteria at screening.

5.2 Treatment Period

While the subject is receiving study treatment, the subject's clinical status is to be evaluated by the treating physician at each clinic visit to confirm that the subject is suitable for continuing study treatment and to make timely decisions regarding the interruption or restarting of study treatment. Clinical laboratory results from samples obtained during clinic visits and tumor assessments from imaging visits are to be reviewed by the treating physician. Also refer to Section 5.6.5 for handling of samples for laboratory assessments.

Subjects will receive study treatment as long as they continue to experience clinical benefit in the opinion of the investigator or until unacceptable toxicity, the need for subsequent systemic anticancer treatment, or until any other reasons for treatment discontinuation listed in the protocol (Section 3.8). Administration of study treatment may continue after radiographic progression per RECIST 1.1 as long as subjects meet all of the following criteria:

Evidence of clinical benefit, as determined by the investigator following a review of all available data Absence of symptoms and signs indicating unequivocal progression of disease (eg, laboratory values, such as clinically significant hypercalcemia for subjects with RCC that cannot be managed by optimizing supportive therapy)

Absence of decline in ECOG performance status that can be attributed to disease progression Absence of tumor progression at critical anatomical sites (eg, leptomeningeal disease) that cannot be managed by protocol-allowed medical interventions.

The investigator should take into consideration the possibility of a delayed anti-tumor immune response with the possibility of regressing and enlarging tumor lesions at the same imaging time point (mixed response) or the appearance of new lesions prior to achieving a radiological response.

Clinic visits for safety evaluations will occur at minimum every 3 weeks (±3 days) after treatment is initiated independent of any dose delays or interruptions. The final assessment will occur at the Post-Treatment Follow-Up Visit unless an AE is determined to be ongoing (see Section 5.3).

If study treatment is interrupted or delayed due to AEs, investigators should perform additional safety assessments weekly (or more frequently as clinically indicated).

Radiographic tumor assessments will be performed as described in Section 5.6.8. The schedule of assessments should be followed regardless of whether study treatment is reduced, interrupted, delayed, or discontinued.

5.2.1 Dose-Escalation Stage

In the Dose Escalation Stage, cohorts will be defined by the starting dose-level of cabozantinib evaluated and the schedule of the first infusion of atezolizumab (either on C1D1 with the first dose of cabozantinib or on C2D1, 21 days after the first dose of cabozantinib; see Section 3.5.1). Eligible subjects will be enrolled in the open cohort, irrespective of tumor type. Subjects in the Dose Escalation Stage will be treated and evaluated according to the schedule of assessments provided in Appendix A.

5.2.2 Expansion Stage

Subjects in the Expansion Stage will be assigned to a treatment cohort based on tumor type and prior cancer history a described in Section 3.5.2. Subjects in the Expansion Stage will be treated at a cabozantinib starting dose level defined by the CRC in combination with atezolizumab.

Study treatment will be administered according to the CRC-recommended dosing schedule; only one dose level and dosing schedule will be evaluated in the Expansion Stage. Expansion Cohort subjects will be evaluated according to the scheduled of assessments provided in Appendix B.

5.3 Post-Treatment Period

Subjects who discontinue from study treatment will return to the site 30 days (+14 days) after the date of the decision to discontinue study treatment for a Post-Treatment Follow-Up Visit. During the Post-Treatment Follow-Up Visit, safety assessments will be performed. Refer to Appendix A (Dose Escalation Stage) or Appendix B (Expansion Stage) for a description of all assessments for the Post Treatment Follow-Up Visit.

Adverse events (including irAEs and AESIs) are to be documented and/or followed as described in Section 8.4.

Subjects will be followed for OS as described in Section 5.6.10. Receipt of nonprotocol anticancer therapy will be collected during survival follow-up. If a subject is lost to follow-up, multiple attempts to contact the study subject or designee must be documented in the subject records.

Radiographic tumor assessments may need to be collected until radiographic progression as described in Section 5.6.8.

These assessments in the Post-Treatment Period (including the Post-Treatment Follow-Up Visit) are not required for subjects who discontinue study treatment in the Maintenance Phase (such subjects are to be followed per standard of care).

5.4 Maintenance Phase

When sufficient data have been collected to adequately evaluate all study endpoints, and upon site notification by the Sponsor, subjects who continue study treatment will enter the study Maintenance Phase. Upon initiation of the Maintenance Phase, the Sponsor considers the safety and efficacy profile of the drug within this study to have been sufficiently established for regulatory purposes. After implementation of the Maintenance Phase, the study will be considered complete at sites and in countries that no longer have active subjects.

In the Maintenance Phase, subjects will continue to receive study treatment until a criterion for protocol-defined discontinuation has been met (Section 3.8). Subjects are to undergo periodic safety assessments (including local laboratory tests) and tumor assessments (Appendix C). The nature and frequency of these assessments are to be performed per standard of care if allowed per local regulations. It is the Investigator's responsibility to ensure that subject visits occur frequently enough and adequate assessments are performed to ensure subject safety.

In order to continue to collect important safety information on subjects still enrolled in the study, reporting of SAEs, AESIs, and other reportable events (pregnancy and medication errors with sequelae) is to continue per protocol (Section 8).

Further, the following AEs (including irAEs), whether serious or not, are to be reported using the same process as for reporting SAEs described in the protocol Section 8.2 (though SAE reporting timeline requirements do not apply to non-serious events reported in these categories):

Adverse events (including irAEs), whether serious or not, leading to study treatment discontinuation Adverse events (including irAEs), whether serious or not, leading to study treatment dose modification (ie, causing study treatment to be interrupted, delayed, or reduced) Study drug accountability is to continue as described in Section 6.4.

Only data collected prior to implementation of Maintenance Phase will be reported in a clinical study report.

5.5 Unscheduled Visits or Assessments

If the investigator determines that a subject should be monitored more frequently or with additional laboratory parameters assessments than indicated by the protocol-defined visit schedule, unscheduled visits or assessments are permitted. The laboratory assessments will be done by the central lab; however, if the results are needed immediately (eg, for AE management), they may be done by the local lab and the results forwarded to the management vendor for handling of local laboratory data. Whenever possible a sample for central lab analysis will also be collected. During a dose interruption due to AE (ie, the time between the last dose and the time drug is restarted), the study site should perform unscheduled visits weekly (or more frequently as clinically indicated) to monitor subject safety and appropriateness for re-treatment with study treatment.

5.6 Procedure Details 5.6.1 Demographics, Medical and Cancer History

Demographics at screening will include age at informed consent, medical and cancer history, surgical history, radiation therapy history, and systemic anticancer treatment history including names of agents and administration dates.

Refer to Appendix A for the schedule of these assessments for the Dose Escalation Stage and Appendix B for the Expansion Stage.

5.6.2 Physical Examination

Physical examinations at screening will include height, weight, performance status, and an assessment of the following systems: skin, head, eyes, ears, nose, throat, respiratory system, cardiovascular system, GI system, neurological condition, blood and lymphatic systems, and the musculoskeletal system. Symptom-directed physical examination will be conducted on C1D1 before the first dose of study treatment and at subsequent safety assessment visits. Any ongoing/intercurrent condition(s) prior to first dose will be recorded in source documents and on case report forms (CRFs).

The Karnofsky performance status will be assessed during screening for subjects with RCC to determine the prognostic risk score according to the MSKCC prognostic criteria (Motzer et al 2004). For all subjects the ECOG performance status will be assessed at screening and at subsequent visits. A table for both performance status scores is included in Appendix E for reference.

Refer to Appendix A for the schedule of physical examination and performance status assessments for the Dose Escalation Stage and Appendix B for the Expansion Stage.

5.6.3 Vital Signs

Vital signs including 5-minute sitting BP, pulse, respiratory rate, and temperature will be assessed at screening, at all scheduled safety visits, and at all unscheduled visits if possible. On atezolizumab infusion days, vital signs should be assessed within 60 min prior to initiation of the infusion, and further vital sign assessment should be performed during and after the infusion as clinically indicated.

Refer to Appendix A for the schedule of these assessments for the Dose Escalation Stage and Appendix B for the Expansion Stage.

5.6.4 Electrocardiogram Assessments

At screening and during the study, single ECG assessments will be performed with standard 12-lead ECG equipment according to standard procedures to determine the corrected QT interval calculated by the Fridericia formula (QTcF). For eligibility, a QTcF ≤ 500 ms per single ECG within 14 days before first dose of study treatment is required. If at any time the single ECG shows a QTcF with an absolute value >500 ms, two additional ECGs at intervals of approximately 3 min must be performed within 30 min after the initial ECG, and the average of these three consecutive results for QTcF will be used (see Section 6.5.2.1.16).

ECGs will be performed at the time points indicated in Appendix A (Dose Escalation Stage) and Appendix B (Expansion Stage).

Abnormalities in the ECG that lead to a change in subject management (eg, dose reduced or interrupted, treatment discontinued; requirement for additional medication or monitoring) or result in clinical signs and symptoms are considered clinically significant for the purposes of this study and will be deemed AEs. If values meet criteria defining them as serious, they must be reported as SAEs (Section 8.2).

The Fridericia formula is depicted below for calculation of QTcF.

$$QTcF = \frac{QT}{RR^{1/3}}$$

5.6.5 Laboratory Assessments

Laboratory analytes that will be measured for this study are listed in Table 5-1. The schedule for laboratory assessments is provided in Appendix A for the Dose Escalation Stage and in Appendix B for the Expansion Stage. Laboratory tests to establish eligibility must be done within 14 days prior to first dose of study treatment unless otherwise stated.

Hematology, serum chemistry, coagulation, UPCR including components, and thyroid function tests are to be performed by a central laboratory for samples collected at scheduled safety visits and at unscheduled visits whenever possible. All central laboratory results will be provided to the investigator. Local laboratory assessments for these panels may be obtained and used if the results are required by the investigator in a rapid timeframe. All local laboratory results must be forwarded to the study local laboratory management vendor if performed in lieu of the central laboratory assessment at any scheduled or unscheduled visit.

Routine (dipstick) urinalysis, microscopic urine examination, and serum and urine pregnancy tests are to be performed by a local laboratory. Results or status from these tests will be recorded on CRFs and will not be submitted to the study local laboratory management vendor.

If performed to determine eligibility or at any scheduled or unscheduled visit, 24-hour urine protein tests are to be performed by a local laboratory and the lab results are to be forwarded to the study local laboratory management vendor.

Serum chemistry, hematology, and urinalysis laboratory samples must be collected and the results must be reviewed within 72 h before any atezolizumab infusion administered on study.

Throughout the study, fasted glucose is to be monitored (no caloric intake for at least 8 hours, consumption of water is allowed).

A serum pregnancy test must be repeated before dosing on C1D1 unless a pregnancy evaluation was done during screening within 7 days prior to C1D1. Urine pregnancy tests will be performed for post-baseline pregnancy evaluations.

Hepatitis B surface antigen and Hepatitis C antibody (with reflex testing of Hepatitis C virus RNA if antibody test is positive) will be assessed at screening.

For CRPC subjects, baseline testosterone and PSA levels will be assessed at screening. After screening, PSA levels will be assessed as described in Section 5.6.8.3 and the schedule of assessments for the dose expansion stage (Appendix B).

TABLE 5-1

Clinical Laboratory Panels

Central Laboratory
If performed by local laboratory in lieu of central lab assessment, submit results to study local laboratory management vendor

| Hematology | Serum Chemistry | Urine Chemistry |
|---|---|---|
| White blood cell (WBC) count with differential (ANC, basophils, eosinophils, lymphocytes, monocytes) hematocrit platelet count red blood cell count hemoglobin Coagulation prothrombin time (PT)/International Normalized Ratio (INR) partial thromboplastin time (PTT) Thyroid function thyroid-stimulating hormone (TSH) Free thyroxine (T4; required at screening; after screening only if TSH is outside normal range) | albumin total alkaline phosphatase (ALP) amylase alanine amino transferase (ALT) aspartate amino transferase (AST) blood urea nitrogen (BUN) corrected calcium bicarbonate chloride creatinine γ-glutamyltranspeptidase (GGT) glucose (fasted) lactate dehydrogenase (LDH) lipase magnesium phosphorus potassium sodium total bilirubin (conjugated and unconjungated if total bilirubin elevated) total protein hepatitis B surface antigen (HBsAg; screening) hepatitis C virus antibody (HCV Ab; HCV RNA reflex testing if antibody positive [screening]) | Protein (spot urine; fully quantitative) Creatinine (spot urine; fully quantitative) Urine protein/creatinine ratio (UPCR; spot urine) Other Analyses (for CRPC subjects in Cohort 6) Testosterone (serum, baseline only) Prostate-specific antigen (PSA) |

Local Laboratory
Submit only 24-hour urine protein test results to study local laboratory management vendor

| Urinalysis (Dipstick or Routine as per institutional standard) investigator based on results or pH specific gravity ketones protein glucose nitrite urobilinogen leukocyte esterase blood | Microscopic Urine Examination Perform at the discretion of the routine urinalysis or as clinically indicated Urine Chemistry 24-hour urine protein: perform at the discretion of the investigator based on increases in UPCR from routine assessments | Pregnancy Blood Test (prior to first dose) 13-human chorionic gonadotropin (13-HCG) Pregnancy Urine or Blood Test (after first dose of study treatment) 13-human chorionic gonadotropin (13-HCG) |

TABLE 5-2

Estimation of the Creatinine Clearance by Cockcroft and Gault

Serum creatinine in conventional units (mg/dL)

Males: $(140 - \text{age}) \times \text{weight (kg)}/(\text{serum creatinine} \times 72)$
Females: $[(140 - \text{age}) \times \text{weight (kg)}/(\text{serum creatinine} \times 72)] \times 0.85$ Serum creatinine in SI units (μmol/L)

Males: $[(140 - \text{age}) \times \text{weight (kg)}/(\text{serum creatinine})] \times 1.23$
Females: $[(140 - \text{age}) \times \text{weight (kg)}/(\text{serum creatinine})] \times 1.04$ Abnormalities in any clinical laboratory test (including tests not required per protocol) that lead to a change in subject management (eg, dose interrupted, delayed, or reduced, treatment discontinued; requirement for additional medication or monitoring) are considered clinically significant for the purposes of this study and will be reported as AEs. If laboratory values constitute part of an event that meets criteria defining it as serious, the event (and associated laboratory values) needs to be reported as an SAE (see Section 8.2).

5.6.6 Pharmacokinetic Assessments

Unless otherwise approved by the Sponsor, PK blood samples will be obtained from all enrolled subjects as described in Section 5.6.6.1 as well as in Appendix A for the Dose Escalation Stage and in Appendix B for the Expansion Stage.

5.6.6.1 Pharmacokinetic Blood Samples

Samples will be collected for the evaluation of cabozantinib PK. The plasma concentrations of cabozantinib will be measured, and the results will be used to confirm exposure to cabozantinib, to identify possible drug-drug interactions between cabozantinib and atezolizumab, and to further characterize the PK for cabozantinib and/or possible relevant break-down products of cabozantinib in these populations. PK analysis may also be run for atezolizumab if deemed appropriate. Collection of PK samples may be halted early or sampling frequency may be modified at the discretion of the Sponsor.

Dose Escalation Stage:

For subjects on the Standard Dosing Schedule, blood samples for PK analysis will be obtained on the date of first dose of study treatment (C1D1; prior to study treatment administration [cabozantinib and atezolizumab], approximately 5 min after completion of the atezolizumab infusion, and at 2 h, 4 h, and 6-8 h after cabozantinib dosing), and prior to study treatment dosing on C1D10, C2D1, and C3D1. For subjects on the Cabozantinib Run-In Dosing Schedule, blood samples for PK analysis will be obtained on the date of first dose (C1D1; samples taken prior to study treatment administration [cabozantinib and atezolizumab], and at 2 h, 4 h, and 6-8 h after cabozantinib dosing), and prior to study treatment on C2D1, C2D10, and C3D1.

Expansion Stage:

For subjects on the Standard Dosing Schedule, blood samples for PK analysis will be obtained on the date of first dose of study treatment (C1D1; prior to study treatment administration [cabozantinib and atezolizumab], approximately 5 min after completion of the atezolizumab infusion, and 2 h after the first dose of cabozantinib) and prior to study treatment dosing on C2D1 and C3D1. For subjects on the Cabozantinib Run-In Dosing Schedule, blood samples for PK analysis will be obtained on the date of first dose (C1D1; samples taken prior to study treatment administration [cabozantinib and atezolizumab] and 2 h after the first dose of cabozantinib) and prior to study treatment on C2D1 and C3D1.

For details refer to Appendix A for the schedule of these assessments for the Dose Escalation Stage and Appendix B for the Expansion Stage.

5.6.7 Biomarker Assessments

Blood and tissue samples will be obtained from consented subjects for analysis of established and/or exploratory biomarkers. Refer to Appendix A for the schedule for these assessments for the Dose Escalation Stage and Appendix B for the Expansion Stage.

The required and optional blood samples will be used to study plasma, serum, and cellular biomarkers. Archival and optional fresh tumor tissue samples will be used to evaluate changes in biomarker expression and genetic/genomic alterations. The analyses will help identify biomarkers that are predictive of response to the study drug, and may help improve understanding of tumor development, tumor microenvironment and effects on peripheral immune activity for the study indications.

Analyses may include, but may not be limited to, sequencing of DNA and/or RNA from tissue and/or blood (plasma) to look for genetic/genomic changes (eg, mutations, copy number variation, mutational burden), immunohistochemical (IHC) assessment of biomarker levels in tissue (eg, MET, AXL, PD-L1), and immune cell profiling by fluorescence-activated cell sorting (FACS) analyses. These studies may use conventional as well as novel technology or methodology. The goal is to correlate modulation of these putative biomarkers to clinical outcome as a consequence of cabozantinib and atezolizumab treatment. The determination of PD-L1 levels is for research/exploratory purposes in this study and will not be shared with investigators as these results will not impact therapeutic decisions. Immune cell profiling by FACS may be conducted at selected sites.

In addition, single nucleotide polymorphism (SNP) genotyping may be performed in order to correlate variations in subject genotype with the safety/tolerability, PK, and/or pharmacodynamics of cabozantinib and atezolizumab.

The biomarker assessment samples may also be used for diagnostic assay development related to study drug and for the discovery of biomarkers that may prove to be valuable surrogates for clinical response as well as to understand the underlying mechanisms of the disease.

For NSCLC subjects, available tumor mutation analysis reports should be provided at screening.

5.6.8 Tumor Assessment 5.6.8.1 Routine Tumor Assessment

Determination of the study endpoints of ORR, DOR, and PFS will be based on tumor assessment by the investigator per RECIST 1.1 (Appendix F). Additional exploratory efficacy evaluation of immune-related response will include the application of modified RECIST (Appendix 0). Independent review of tumor assessments may be requested at the discretion of the study sponsor; this would potentially include submission of all radiographic images from the study (eg, CT/MRI, technetium bone scans) to an independent radiology core laboratory.

Radiographic tumor assessments will include the following:

1. Chest/Abdomen/Pelvis (CAP): CT of CAP or CT chest and MRI of abdomen/pelvis will be performed in all subjects at screening and every 6 weeks (5 days) after initiation of study treatment throughout the first 12 months on study. Upon completion of 12 months on study, these assessments will be performed every 12 weeks (& 7 days).
2. Brain: MRI (or CT) of the brain will be performed at screening in all subjects with RCC and NSCLC and for subjects with CRPC or UC who have a history or clinical symptoms of brain metastasis. After study treatment initiation MRI (or CT) scans of the brain are only required in subjects with documented, treated brain metastasis or if clinically indicated by signs and symptoms suggestive of new central nervous system (CNS) metastases. Assessments after the first dose of study treatment will be performed every 12 weeks (±7 days). MRI is the preferred imagining method for brain. If CT of the brain is performed instead of MRI, ambiguous results must be confirmed by MRI. Subjects without documented brain metastasis during the screening assessment are not required to undergo brain imaging after initiating study treatment unless clinically indicated. In order to meet the eligibility requirements of the study, brain metastasis must have been treated and stable for at least 4 weeks before the first dose of study treatment.
3. Bone scans: Technetium bone scans (TBS) will be performed at screening in all subjects with CRPC and for subjects with RCC, UC, or NSCLC who have a history or clinical symptoms (ie, bone pain) of bone metastases. After study treatment initiation bone scans are only required in subjects with documented bone lesions or if clinically indicated by signs and symptoms suggestive of new bone metastases. Assessments after the first dose will follow routine clinical practice (approximately every 12 weeks throughout the first 12 months and every 24 weeks thereafter). Lesions identified on bone scan are not to be recorded as target, non-target, or new lesions. Bone scans are to be used to direct corroborative imaging with CT/MRI if necessary (these CT/MRI findings will be used for RECIST v1.1 evaluation), and bone scan findings alone should not be used for the determination of progression in this study.

Investigators are encouraged, if any doubt or ambiguities exist about radiographic progression, to continue study treatment if the subject is tolerating it acceptably, repeat radiographic tumor imaging at the next scheduled time point, and delay determination of progression until the findings indicating radiographic progression are unequivocal. Radiographic progression determined by the investigator does not warrant discontinuation of tumor assessments or study treatment (see Section 3.8).

End of radiographic imaging:
- For subjects who discontinue study treatment before radiographic disease progression per RECIST 1.1, regularly scheduled imaging assessments should continue if possible until radiographic progression per RECIST 1.1 or initiation of subsequent anticancer therapy.
- For subjects who discontinue tumor assessments at the time of radiographic progression per RECIST 1.1 no additional tumor imaging is required.
- Bone scan evaluations will end on the date of last CT/MRI scan. If the bone scan schedule doesn't coincide with the last CT/MRI scan, no additional bone scan is needed after the last CT/MRI scan has been performed.

Refer to Appendix A for the schedule for these assessments for the Dose Escalation Stage and Appendix B for the Expansion Stage.

5.6.8.2 Confirmation of Tumor Response and Tumor Progression

For subjects with an overall response of PR or CR per RECIST 1.1 at a given time point, changes in tumor measurements must be confirmed by repeat assessments to be performed no fewer than 4 weeks after the criteria for response are first met.

In order to identify potential delayed immune-mediated tumor response, subjects with an overall response of PD per RECIST 1.1 who continue with study treatment because of evidence of clinical benefit as assessed by the investigator should have tumor measurement outcomes confirmed ≥4 weeks after the initial PD criteria were met. Continuation of study treatment after confirmatory tumor imaging is at the discretion of the investigator. For subjects who continue treatment after the confirmatory tumor imaging, regularly scheduled imaging will continue.

5.6.8.3 PSA Assessment

For subjects with CRPC (Expansion Cohort 6), samples for PSA are to be collected at screening, Day 1 of every third cycle for the first 6 months on study and then Day 1 of every fifth cycle until the earlier of initiation of subsequent systemic anticancer therapy or permanent loss to radiographic follow-up (including hospice admission). The samples will be analyzed by a central laboratory.

PSA assessments should not be used for study treatment descisions.

5.6.9 Subject Daily Dosing Diary

Subjects in the Dose Escalation Stage will be provided a daily dosing diary with instructions to record cabozantinib treatment taken outside the clinic during the DLT Evaluation Period.

For subjects on the Standard Dosing Schedule, the diary will be initially distributed on C1D1, and it will be collected at the beginning of Cycle 2. For subjects on the Cabozantinib Run-In Dosing Schedule, the diary will be initially distributed on C2D1, and it will be collected at the beginning of Cycle 3.

The daily diary is not a CRF. The diary will serve as source documentation and be maintained with other subject clinical source documents. Study site staff should carefully review the diary with the subject and to ensure it is complete and accurate before transcription to the subject's CRFs.

5.6.10 Overall Survival

Following study treatment discontinuation each subject will continue to be followed for survival and subsequent anticancer treatment. The investigator (or designee) will make contact with the subject at least as frequently as every 12 weeks (±7 days) after the Post-Treatment Follow-Up Visit until the subject expires or the Sponsor decides to discontinue collection of these data for the study.

At each contact, the investigator (or designee) will determine if the subject is alive and collect information on nonprotocol anticancer treatments the subject has received. If the subject has died the investigator will record the date and cause of death as best can be determined. All efforts must be undertaken by the study sites to determine the date of death (or date subject last known alive at the time of a data cut-off). This may include, but not necessarily be limited to telephone contacts, communication at study visits, registered letters, and reviews of local obituaries and government death records (if allowed by local laws and regulations).

Refer to Appendix A for the schedule for these assessments for the Dose Escalation Stage and Appendix B for the Expansion Stage.

These assessments are not required for subjects who discontinue study treatment in the Maintenance Phase (such subjects are to be followed per standard of care).

6 Treatments 6.1 Composition, Formulation, and Storage

At study sites, all study medication will be stored as described in the appropriate prescribing information for that country (if applicable) or the pharmacy manual and inventoried in accordance with applicable state and federal regulations.

6.1.1 Investigational Treatment: Cabozantinib

The Sponsor will provide each investigator with adequate supplies of cabozantinib, which will be supplied as 60-mg and 20-mg yellow film-coated tablets. The 60-mg tablets are oval and the 20-mg tablets are round. Doses of 40 mg will comprise two 20-mg tablets. The components of the tablets are listed in Table 6-1.

TABLE 6-1

Cabozantinib Tablet Components and Composition

| Ingredient | Function | % w/w[a] |
|---|---|---|
| Cabozantinib Drug Substance (25% drug load as free base) | Active Ingredient | 31.68 |
| Microcrystalline Cellulose (Avicel ® PH-102) | Filler | 38.85 |
| Lactose Anhydrous (60M) | Filler | 19.42 |
| Hydroxypropyl Cellulose (EXF) | Binder | 3.00 |
| Croscarmellose Sodium (Ac-Di-Sol ®) | Disintegrant | 6.00 |
| Colloidal Silicon Dioxide | Glidant | 0.30 |
| Magnesium Stearate | Lubricant | 0.75 |
| Opadry ® yellow film coating which includes HPMC 2910/hypromellose 6 cp, titanium dioxide, triacetin, and iron oxide yellow | Film Coating | 4.00 |

[a]weight fraction, expressed in percentage;
HPMC, Hydroxypropyl methylcellulose Refer to the Pharmacy Manual for details on storage and handling of cabozantinib.

6.1.2 Combination Treatment: Atezolizumab

Atezolizumab is an Fc-engineered, humanized, monoclonal antibody (non-glycosylated IgG1 kappa immunoglobulin) produced in Chinese hamster ovary cells with a calculated molecular mass of 145 kDa.

The Sponsor will provide each investigator with adequate supplies of atezolizumab, which will be supplied as a 1200 mg/20 mL (60 mg/mL) colorless to slightly yellow solution in single-dose vials. Atezolizumab solution contains the following inactive ingredients: glacial acetic acid, L-histidine, sucrose, and polysorbate 20. Refer to the package insert (or the local label) and the pharmacy manual for additional information and instructions for preparing atezolizumab for infusion. Solution used as diluent (0.9% NaCl) should be sourced by investigative sites if available and permitted by local regulations.

6.2 Schedule of Treatment

Cabozantinib will be administered orally at assigned daily dose levels of 20, 40, or 60 mg. Atezolizumab will be administered at a standard dosing regimen of 1200 mg as an IV infusion once every 3 weeks. Subjects in the Dose Escalation Stage on the Standard Dosing Schedule will receive the combination regimen with the first infusion of atezolizumab given on the same day as the first dose of cabozantinib. On the Cabozantinib Run-In Dosing Schedule (if implemented by the CRC), the first infusion of atezolizumab will be given on C2D1, 21 days after the first dose of single-agent cabozantinib. In the Expansion Stage, all subjects will receive cabozantinib at the recommended dose and schedule as determined by the CRC. Further instructions for treatment administration are provided in Sections 6.2.1 and 6.2.2.

Subjects will receive study treatment with cabozantinib and atezolizumab as long as they continue to experience clinical benefit as assessed by the investigator or until unacceptable toxicity, the need for subsequent systemic anticancer treatment, or until any other reasons for treatment discontinuation listed in the protocol (Section 3.8). Discontinuation of one component of the combination study treatment while continuing to receive the other may be allowed but requires Sponsor notification.

For guidance on dose modifications, interruptions, delays, or discontinuations due to AEs, refer to Section 6.5.1.

6.2.1 Administration at the Clinic

Cabozantinib:

The first dose of cabozantinib will be administered at the clinic. If both study treatments are administered on C1D1, atezolizumab is to be administered first. The subject will be fasted (with the exception of water) for at least 2 hours before receiving cabozantinib. Upon completion of the 2-hour fast, the subject will receive the oral dose of cabozantinib with a minimum of 8 oz (240 mL) of water in the clinic and then the subject will continue to fast for 1 hour while under observation to monitor for potential AEs. For cabozantinib dosing on subsequent dosing days refer to Section 6.22.

Atezolizumab:

Subjects on the Standard Dosing Schedule will receive their first dose of atezolizumab on the same day as the first dose of cabozantinib (C1D1). Subjects on the Cabozantinib Run-In Dosing Schedule (if implemented) will receive their first dose of atezolizumab on C2D1, 21 days after their first dose of cabozantinib.

Doses of atezolizumab will always be administered intravenously at the clinic by infusion on Day 1 of each 21-day cycles (−2 days). Cycles may be longer than 3 weeks if atezolizumab treatment is delayed due to toxicity or other reasons.

The infusion of atezolizumab (1200 mg fixed dose) will be prepared according to local prescribing information or the pharmacy manual. The IV administration of atezolizumab can only occur in a clinical setting with staff experienced in managing of infusion-related reactions and with access to emergency services. The initial intravenous (IV) infusion of atezolizumab will be given over 60 min (±15 min) without premedication for potential infusion-related reactions. Subsequent IV infusions may be given over 30 min (±10 min) if the initial infusion is tolerated. Premedication for infusion-reaction is allowed after the initial infusion. No bolus or IV push of atezolizumab is allowed. Dose delays will be allowed for toxicities suspected to be due to atezolizumab administration. Atezolizumab infusion requirements and guidance we summarized in Table 6-2.

TABLE 6-2

Atezolizumab Infusion Requirements and Guidance

| First Infusion | Subsequent Infusions |
|---|---|
| No premedication is permitted. Vital signs (blood pressure, pulse, respiratory rate, and temperature) should be recorded within 60 min prior to the infusion. Atezolizumab should be infused over 60 (±15) min. If clinically indicated, vital signs should be recorded during the infusion at 15, 30, 45, and 60 min (±5 min for all time points) during the infusion and at 30 (±10) min after the infusion. Subjects should be informed about the possibility of delayed post-infusion symptoms and instructed to contact their study physician if they develop such symptoms. | If the subject experienced an infusion-related reaction with any previous infusion, premedication with antihistamines, antipyretics, and/or analgesics may be administered for subsequent doses at the discretion of the investigator. Vital signs should be recorded within 60 min prior to the infusion. Atezolizumab should be infused over 30 (±10) min if the previous infusion was tolerated without an infusion-related reaction, or 60 (±15) min if the subject experienced an infusion-related reaction with the previous infusion. If the subject experienced an infusion-related reaction with the previous infusion or if clinically indicated, vital signs should be recorded during the infusion and at 30 (±5) min after the infusion. |

After the IV administration of the first dose of atezolizumab in the clinic, the subject will wait for at least 1 hour before taking cabozantinib. If the subject develops a transfusion reaction, the oral administration of cabozantinib will be delayed or interrupted until the subject has recovered and the investigator believes that it is safe to administer cabozantinib. For management of infusion-related reactions refer to Appendix H.

If the first dose of atezolizumab cannot be given for any reason, the following is to occur:

On the Standard Dosing Schedule, no oral treatment with cabozantinib is to be initiated.

On the Cabozantinib Run-In Dosing Schedule, cabozantinib is to be interrupted (if not already the case) and discontinuation of study treatment is to be considered. Continued treatment with cabozantinib as a single agent may be allowed with notification of the Sponsor.

6.2.2 Cabozantinib Administration Outside the Clinic

The subject should take cabozantinib outside the clinic at approximately the same time every day, preferentially before going to bed, and should adhere to the fasting requirements described in this section.

Subjects should fast (with the exception of water) for at least 2 hours after eating the evening meal before taking their dose. After the 2-hour fast and before going to bed, subjects are to take cabozantinib with a full glass of water (minimum of 8 oz or 240 mL) with no more food intake for one hour post-dose. If the subject's schedule requires taking cabozantinib during the day, the subject is to be instructed to follow the same fasting recommendations.

Cabozantinib tablets should not be crushed or chewed. Grapefruit and Seville oranges (and products made from them) should be avoided while being treated with cabozantinib.

Subjects are to be instructed to not make up vomited doses and to maintain the planned dosing schedule. Subjects are not to make up for missed doses if more than 12 hours have elapsed after the time the subject would usually take cabozantinib. In the event of missed doses, subjects are not to take 2 doses to make up for the one the subject missed.

Subjects enrolled in the Dose Escalation Stage will be expected to complete a cabozantinib-administration diary during the DLT Evaluation Period (Section 5.6.8.3).

Any unused study treatment must be returned to the study site for drug accountability and disposal.

6.3 Compliance

Subject compliance with outpatient study treatment will be assessed by the site using drug dispensing and return records, progress notes about dose reductions/interruptions, subject interview, and the subject daily diary (DLT Evaluation Period of the Dose Escalation Stage cohorts only, Section 5.6.8.3). These data will not be directly recorded in the CRF; rather, the CRF will capture intervals of constant dose and reasons for changes in dose level (eg, a new record completed each time dose level changes, including periods where no dose was taken, and the reason for a dose level change).

6.4 Study Treatment Accountability

The investigator or designee will maintain accurate records of receipt of all study treatment including dates of receipt. In addition, accurate records will be kept regarding when and how much study treatment is dispensed and used by each subject in the study. Reasons for deviation from the expected dispensing regimen must also be recorded. At completion of the study, to satisfy regulatory requirements regarding drug accountability, all unused study treatment will be reconciled and destroyed according to applicable state, federal, and local regulations.

6.5 Safety Considerations 6.5.1 Management of AEs with Dose Reductions and/or Dose Interruptions Subjects will be monitored for AEs from the time of signing informed consent through 30 days (90 days for AESIs) after the date of the decision to permanently discontinue all study treatment. Subjects will be instructed to notify their physician immediately for any occurring AE. Causality assessment of AEs should include at minimum confounding factors such as disease and concomitant medications. Adverse event severity will be graded by the investigator according to CTCAE v.4.0.

The following should be taken into consideration in decisions regarding dose modifications (reductions and/or interruptions) for treatment-related side effects:

Cabozantinib and atezolizumab have class-specific safety profiles based on their mechanism of action but may also cause AEs that overlap. For management of AEs which can be clearly attributed to cabozantinib or atezolizumab, independent dose modification for either agent is allowed. Examples of VEGFR TKI associated AEs caused by cabozantinib are hypertension and hand-foot syndrome. Examples of irAEs caused by atezolizumab are pneumonitis and endocrinopathies. For AEs without clear attribution to either study treatment, management of toxicity should include dose modifications of both agents per the discretion of the investigator. Examples of overlapping AEs are diarrhea and transaminase increases.

As a general approach all AEs should be managed with supportive care including both pharmacological and non-pharmacological treatments according to consensus management guidelines at the earliest signs of toxicity considered related to study treatment.

Study treatment may be continued for mild AEs if appropriate supportive care has been initiated to ameliorate symptoms. Should this be ineffective and toxicities become unacceptable, dose modifications of study treatment should be considered to prevent worsening of toxicity. Moderate to severe AEs usually require dose modifications including dose reductions and/or interruptions.

Dose interruptions of cabozantinib or atezolizumab for AEs may occur at any time and independently at the discretion of the investigator. If either or both study treatments are interrupted for more than 12 weeks, the sponsor should be contacted to discuss treatment continuation.

Cabozantinib:

The assigned dose for cabozantinib in Cohort 1 of the Dose Escalation Stage is 40 mg qd. The assigned dose for cabozantinib for the Expansion Stage will be determined in the Dose Escalation Stage. The maximum protocol-allowed dose for cabozantinib is 60 mg qd.

Three dose reduction levels of cabozantinib (40 mg daily, 20 mg daily, and 20 mg qod) are permitted (see Table 6-3).

For subjects in the Dose Escalation Stage, dose reductions or interruptions of cabozantinib during the DLT Evaluation Period may result in DLTs (refer to Section 3.5.1.4).

Dose modification criteria for treatment-related AEs of cabozantinib are shown in Table 6-4.

Dose reinstitution and reescalation after dose interruptions and/or reductions:

If the subject recovers from his or her toxicities to CTCAE v.4.0<Grade 1 or to the baseline value (or lower) and the AE was unrelated to cabozantinib, then cabozantinib may be restarted with no change in dose.

If the subject recovers from his or her toxicities to <Grade 1 or to the baseline value (or lower) the AE was deemed possibly related to cabozantinib, then cabozantinib may be restarted at a reduced dose (see Table 6-3).

Subjects receiving a dose of 20 mg qod may be restarted at the same dose if deemed safe at the discretion of the investigator. Subjects unable to tolerate a dose of 20 mg qod should discontinue cabozantinib.

Reescalation to the previous dose may be allowed during the Expansion Stage at the discretion of the investigator for AEs which have resolved or recovered to Grade 1 (or baseline value) and deemed tolerable and easily managed by optimized supportive treatment. Dose reescalation is not allowed during the Dose Escalation Stage or following a cabozantinib-related dose reduction for Grade 4 AEs affecting major organs (eg, CNS, cardiac, hepatic, renal).

Guidelines for the management of specific AEs of cabozantinib such as GI disorders, non-GI fistula formation, hemorrhage, thromboembolic events, hypertension, stomatitis and (qod) permitted mucositis, skin disorders, osteonecrosis, proteinuria, nervous system disorders, hepatocellular toxicity, infections and infestations, blood system disorders, fatigue, weight loss, QTc prolongation, electrolyte disorders, endocrine disorders, and respiratory disorders are provided in Section 6.5.2.1.

TABLE 6-3

Dose Reductions of Cabozantinib (Oral Dosing)

| Assigned Starting Dose | First Dose Level Reduction | Second Dose Level Reduction | Third Dose Level Reduction |
| --- | --- | --- | --- |
| 60 mg daily (qd) | 40 mg daily (qd) | 20 mg daily (qd) | 20 mg every other day (qod) |
| 40 mg daily (qd) | 20 mg daily (qd) | 20 mg every other day (qod) | No dose reduction permitted |
| 20 mg daily (qd) | 20 mg every other day | No dose reduction | |

Though a dose level of 20 mg every other day (god) is permitted resulting from dose reductions, that dose level will not be evaluated as an assigned starting dose in either stage of this study. Cabozantinib will be discontinued if a dose of 20-mg cabozantinib every other day (minimum dose) is not tolerated.

TABLE 6-4

Dose Modifications for Cabozantinib-Associated AEs

| CTCAE v.4.0 Grade | Recommended Guidelines for Management[a] |
| --- | --- |
| Grade 1 AEs cabozantinib | Add supportive care as indicated. Continue at the current dose level if AE is manageable |
| Grade 2 AEs which are tolerable and are easily managed | Continue cabozantinib at the current dose level with supportive care. |
| Grade 2 AEs which are intolerable and cannot be adequately managed | Cabozantinib should be dose reduced or interrupted. Note: It is recommended that dose interruptions be as brief as possible. and tolerable. |
| Grade 3 AEs (except clinically non-relevant laboratory abnormalities) | Cabozantinib should be interrupted unless the toxicity can be easily managed with a dose reduction of cabozantinib and optimal medical care. Note: It is recommended that dose interruptions be as brief as possible. |
| Grade 4 AEs (except clinically non-relevant laboratory abnormalities) | Cabozantinib must be interrupted immediately. In general, cabozantinib should be discontinued unless the following criteria are met: Subject is deriving clear clinical benefit as determined by the investigator and agreed by the Sponsor Toxicity can be managed with a dose reduction of cabozantinib following recovery to Grade 1 (or baseline) and optimal medical care Sponsor must be contacted to discuss treatment continuation upon resolution of adverse events. |

AE, adverse event.

Note:

Cabozantinib dose modification criteria for specific medical conditions are provided in Section 6.5.2.1.

Study treatment dose adjustment is only needed if the toxicity was deemed related to treatment or had an unclear relationship to study treatment.

Atezolizumab:

The assigned dose for atezolizumab is 1200 mg IV every 3 weeks. Infusion will occur every three weeks (−2 days) on Day 1 of each Cycle, except subjects on the Cabozantinib Run-In Dosing Schedule (if implemented) will not receive their first dose of atezolizumab until C2D1.

Dose interruptions are allowed for atezolizumab (see Table 6-5) but dose reductions are not allowed.

Dose modification criteria for irAEs and for guidance on reinstituting atezolizumab are shown in Table 6-6.

If corticosteroids are initiated for treatment of irAEs, they must be tapered over ε 1 month to δ 10 mg/day oral prednisone or equivalent before atezolizumab can be resumed.

Guidelines for the management of infusion-reactions and irAEs of atezolizumab (ie, pneumonitis, hepatitis, diarrhea/colitis, myocarditis, endocrinopathies including hypophysitis, and infection) are provided in Section 6.5.2.2.

TABLE 6-5

Dose Interruptions of Atezolizumab

| Assigned dose | Dose Interruptions |
| --- | --- |
| 1200-mg atezolizumab IV q3w | At any time to manage unacceptable irAEs | q3w, every 3 weeks;
irAE, immune-related adverse events

TABLE 6-6

Dose Modifications for Atezolizumab-Associated irAEs

| CTCAE v.4.0 Grade | Recommended Management |
| --- | --- |
| Grade 2 myocarditis | Delay treatment with atezolizumab |
| Grade 2 pneumonitis<br>AST or ALT > 3 and ≤ 5 × ULN or total bilirubin > 1.5 and ≤ 3 × ULN<br>Grade 2 or 3 diarrhea or colitis<br>Symptomatic adrenal insufficiency, hypothyroidism, or hyperthyroidism; Grade 2 or 3 hypophysitis; or Grade 3 or 4 hyperglycemia<br>Grade 2 ocular inflammatory toxicity<br>Grade 2 or 3 pancreatitis or Grade 3 or 4 increases in amylase or lipase levels (>2.0 × ULN)<br>Grade 3 or 4 infection<br>Grade 2 infusion-related reactions<br>Grade 3 rash | Treatment may be resumed in subjects following recovery to Grade 0-1. |
| Grade 3 or 4 myocarditis and/or Grade 2 myocarditis unresolved while withholding atezolizumab<br>Grade 3 or 4 pneumonitis<br>AST or ALT > 5 × ULN or total bilirubin > 3 × ULN<br>Grade 4 diarrhea or colitis<br>Grade 4 hypophysitis and/or recurrent hypophysitis<br>Myasthenic syndrome/myasthenia gravis, Guillain-Barre or meningoencephalitis (all grades) | Permanently discontinue atezolizumab |

TABLE 6-6-continued

Dose Modifications for Atezolizumab-Associated irAEs

| CTCAE v.4.0 Grade | Recommended Management |
| --- | --- |
| Grade 3 or 4 ocular inflammatory toxicity<br>Grade 4 or any grade of recurrent pancreatitis Grade 3 or 4 infusion-related reactions Grade 4 rash | |

ALT, alanine aminotransferase;
AST, aspartate aminotransferase;
irAE, immune-related adverse event;
ULN, upper limit of normal.
Note:
Additional information for atezolizumab dose modification criteria and treatment recommendations for irAEs and infusion reactions are provided in Section 6.5.2.2.

6.5.2 Warnings, Precautions, Guidelines for Management of Adverse Events

Subjects will be monitored for AEs from the time of signing informed consent through 30 days (90 days for AESIs) after the date of the decision to permanently discontinue treatment. Subjects will be instructed to notify their physician immediately for any occurring AE. Causality assessment of AEs should include at minimum confounding factors such as disease and concomitant medications. Adverse event severity will be graded by the investigator according to CTCAE v.4.0

Management of severe or intolerable adverse reactions may require temporary dose reduction and/or interruption for cabozantinib and/or dose delays of atezolizumab therapy.

6.5.2.1 Cabozantinib

The most frequent AEs experienced by 20% of subjects treated with cabozantinib in descending order of frequency were diarrhea, fatigue, nausea, decreased appetite, vomiting, weight decreased, PPE, constipation, hypertension, dysgeusia, dysphonia, and asthenia. For a full description of the safety profile of cabozantinib, refer to the Cabozantinib Investigator's Brochure.

Other medically important but less frequent AEs including arterial thrombotic AEs (eg, TIA, and MI) and venous thrombotic AEs (eg, DVT and pulmonary embolism), severe hemorrhagic events, proteinuria, wound healing complications, GI perforation, abscesses including intra-abdominal and pelvic abscess, OI and non-GI fistula formation, osteonecrosis, and RPLS.

Adverse events associated with laboratory abnormalities experienced by ? 5% of subjects treated with cabozantinib in descending order of frequency were anemia, AST increased, ALT increased, hypothyroidism, hypokalemia, hypomagnesemia, thrombocytopenia, hypocalcemia, hypophosphatemia, lactate dehydrogenase (LDH) increased, lipase increased, neutropenia, hyponatremia, ALP increased, leukopenia, and hyperglycemia.

Adverse events may occur within the first few weeks in the course of treatment with cabozantinib, as cabozantinib is expected to reach steady state exposure at approximately 2 weeks following first dose. Events that generally have an early onset include hypocalcemia, hypokalemia, thrombocytopenia, hypertension, PPE, abdominal pain, mucosal inflammation, constipation, diarrhea, and vomiting. Adverse events should be managed with supportive car at the earliest signs of toxicity. Dose reductions and treatment interruptions should be considered. Dose reductions are recommended for events that, if persistent, could become serious or intolerable (Table 6-3).

Cabozantinib should be discontinued for the following AEs: visceral perforation or fistula formation, severe hemorrhage, serious arterial thromboembolic events, nephrotic syndrome, hypertensive emergency, persistent uncontrolled hypertension despite optimal medical management, and RPLS.

6.5.2.1.1 Gastrointestinal Disorders

Gastrointestinal perforation, GI fistula, and intra-abdominal and pelvic abscess: After starting treatment with cabozantinib, subjects should be monitored for early signs of GI perforation such as abdominal pain, nausea, emesis, constipation, and fever especially if known risk factors for developing GI perforation or fistula (Turnage and Badgwell 2016) are present. Discontinue cabozantinib and initiate appropriate management in subjects who have been diagnosed with GI perforation or fistula.

Diarrhea: Subjects should be instructed to notify their physician immediately at the first signs of poorly formed or loose stool or an increased frequency of bowel movements. Guidelines for the evaluation and management of diarrhea are shown in Table 6-7. Administration of antidiarrheal/antimotility agents is recommended at the first sign of diarrhea as initial management. Some subjects may require concomitant treatment with more than one antidiarrheal agent. When therapy with antidiarrheal agents does not control the diarrhea to tolerable levels, cabozantinib should be temporarily interrupted or dose reduced. When the diarrhea is controlled, retreatment with cabozantinib may be acceptable per investigator decision. In addition, general supportive measures should be implemented such as continuous oral isotonic hydration, correction of fluid and electrolyte abnormalities, small frequent meals, and stopping lactose-containing products, high-fat meals, and alcohol.

Recurrent or prolonged diarrhea can be associated with anal or perianal skin erosions which increase the risk for anal abscesses, fistulas, or proctitis. Good personal hygiene should be emphasized. Regular examinations of the perianal region should be performed whenever diarrhea has occurred during treatment with cabozantinib. Infections of the perianal region should be treated per local guidelines.

TABLE 6-7

Management of Diarrhea Associated with Cabozantinib

| Status | Management |
| --- | --- |
| Tolerable Grade 1-2 (duration < 48 h) | Continue with study treatment and consider dose reduction |
| | Initiate treatment with an antidiarrheal agent (eg, loperamide 4 mg followed by 2 mg after each episode of diarrhea [maximum: 16 mg loperamide per day]) |
| | Dietary modifications (eg, small lactose-free meals, bananas and rice) |
| | Intake of isotonic fluids (1-1.5 L/day) |
| | Re-assess after 24 hours: |
| |    Diarrhea resolving to baseline bowel habits: gradually add solid foods and discontinue or decrease antidiarrheal treatment after 12 h diarrhea-free interval |
| |    Diarrhea not resolving: Continue/resume antidiarrheal treatment |
| Intolerable Grade 2, Grade 2 > 48 h, or ≥ Grade 3 | Interrupt study treatment |
| | Ask subject to attend clinic |
| | Rule out infection (eg, stool sample for culture) |
| |    Administer antibiotics as needed (eg, if fever or Grade 3-4 neutropenia persists > 24 h) |
| | Administer fluids (1-1.5 L/day orally or IV, as appropriate) for hydration or to correct electrolyte abnormalities |
| | For Grade 3-4 or complicated lower grade diarrhea consider hospitalization and IV hydration |
| | Re-assess after 24 h |
| |    Diarrhea resolving to baseline bowel habits or Grade ≤1: consider restarting study treatment at reduced dose |
| |    Diarrhea not resolving: Start and or continue antidiarrheal treatment (eg, loperamide 4 mg followed by 2 mg after each episode of diarrhea [maximum: 16 mg loperamide per day]). Consider starting second line antidiarrheal or referral to gastroenterologist |

Nausea and vomiting: Antiemetic agents are recommended as clinically appropriate for treatment or prophylaxis of nausea and vomiting, along with supportive care. Dehydration and electrolyte abnormalities may be associated with vomiting and monitoring for and correction of fluid and electrolyte disturbances should be implemented. Antiemetic medications should be assessed for potential drug interactions (refer to Section 7.3 for further details).

6.5.2.1.2 Non-Gastrointestinal Fistula

Complications from radiation therapy especially of the thoracic cavity including mediastinum have been identified as a possible predisposing risk factor for non-GI fistula formation in subjects undergoing treatment with VEGF pathway inhibitors.

Discontinue cabozantinib and initiate appropriate management in subjects who have been diagnosed with a non-GI fistula.

6.5.2.1.3 Hemorrhage

Hemorrhagic events, including serious and sometimes fatal events, have been reported with cabozantinib. Subjects should be monitored for bleeding events with serial complete blood counts and physical examination while on study. The risk of hemorrhage in cabozantinib-treated subjects with brain metastases has not been thoroughly analyzed. Subjects enrolled with treated and stable brain metastases should be monitored with a high index of suspicion if symptoms that could be due to a CNS hemorrhage occur.

Cabozantinib should be discontinued in subjects with serious and life-threatening bleeding events or recent hemoptysis (≥2.5 mL of red blood).

6.5.2.1.4 Thromboembolic Events

Thromboembolic events are frequent in cancer subjects due to procoagulant changes induced by the malignancy or anticancer therapy. DVT and pulmonary embolism have been observed in clinical studies with cabozantinib, including fatal events. Subjects who develop a pulmonary embolism and/or DVT should have study treatment interrupted until therapeutic anticoagulation is established. Treatment with cabozantinib may be resumed in subjects with pulmonary embolism or DVT if it is determined that the event is uncomplicated and that the subject is deriving clinical benefit from cabozantinib treatment and that anticoagulation does not place them at a significant risk that outweighs the benefit of resuming treatment per discretion of the investigator and according to individual protocols. Low molecular weight heparins are the preferred management for thrombotic events; oral anticoagulants (eg, warfarin or other coumarin-related agents, direct thrombin or direct FXa inhibitors, or antiplatelet agents, or chronic use of aspirin above low dose levels for cardioprotection per local applicable guidelines) are not allowed.

Arterial thrombotic events (eg, TIA, MI) have been observed in studies with cabozantinib. Further treatment with cabozantinib should be discontinued in subjects who develop an acute MI, cerebral infarction, or any other clinically significant arterial thromboembolic complication.

6.5.2.1.5 Hypertension

Table 6-8 provides treatment guidelines for hypertension deemed related to cabozantinib. Blood pressure should be monitored in a constant position visit to visit, either sitting or supine in a relaxed setting. Decisions to reduce or interrupt the dose of study treatment must be based on BP readings taken by a medical professional and must be confirmed with a second measurement at least 5 minutes following the first measurement.

Cabozantinib should be discontinued in subjects with hypertensive emergency.

TABLE 6-8

| Management of Hypertension Associated with Cabozantinib | |
|---|---|
| Criteria for Dose Modifications | Treatment/Cabozantinib Dose Modification |
| Subjects NOT receiving optimized anti-hypertensive therapy | |
| >150 mmHg (systolic)$^a$ and <160 mmHg OR >100 mmHg (diastolic) and <110 mmHg | optimize antihypertensive medications by adding new or additional antihypertensive medications and/or increase dose of existing medications. Reduce cabozantinib treatment by one dose level if optimal antihypertensive therapy (usually to include 3 agents) does not result in BP < 150 mmHg systolic or <100 mmHg diastolic If subject is symptomatic interrupt cabozantinib treatment |
| ≥160 mmHg (systolic) OR ≥110 mmHg (diastolic) | Reduce cabozantinib by one dose level$^b$ or interrupt cabozantinib treatment per investigator discretion Add new or additional anti-hypertensive medications and/or increase dose of existing medications and monitor subject closely for hypotension. If optimized antihypertensive therapy (usually to include 3 agents) does not result in BP < 150 mmHg systolic or <100 mmHg diastolic, cabozantinib treatment should be dose reduced further or interrupted Cabozantinib treatment should be dose interrupted if upper limits of systolic BP (≥160 mmHg) are sustained and not adequately manageable or if systolic BP is >18 mmHg or diastolic BP >110 mmHg, or if subject is symptomatic |

TABLE 6-8-continued

Management of Hypertension Associated with Cabozantinib

| Criteria for Dose Modifications | Treatment/Cabozantinib Dose Modification |
|---|---|
| | Re-start cabozantinib treatment at the most tolerable dose and re-escalate only if BP falls to and is sustained at <150 mmHg systolic and <100 mmHg diastolic |
| Hypertensive emergency[c] | Discontinue cabozantinib treatment |

BP, blood pressure;
MI, myocardial infarction.
[a]The investigator may decide to initiate or adjust antihypertensive treatment at a lower threshold than systolic BP > 150 or diastolic BP > 100 based on their clinical judgment and assessment of the individual subject.
[b]Permitted dose levels are defined by individual protocols.
[c]Hypertensive emergency is defined as uncontrolled elevated BP with clinical evidence of progressive or impending end-organ damage (eg, MI/ischemia, intracranial hemorrhage, cerebral ischemia, pulmonary edema, encephalopathy, kidney damage).

6.5.2.1.6 Stomatitis and Mucositis

Preventive measures may include a comprehensive oral examination to identify and treat any potential risk for complications before study treatment is initiated. Appropriate correction of local factors should be instituted as indicated, such as modification of ill-fitting dentures and appropriate care of gingivitis. During treatment with cabozantinib, good oral hygiene and standard local treatments such as non-traumatic and non-irritating cleansing, and oral rinses (eg, with a weak solution of salt and baking soda) should be maintained. Lips should be kept moisturized with lip balm. The use of lipstick, lip-gloss, and Vaseline should be avoided.

Local treatment should be instituted at the earliest onset of symptoms. Obtain bacterial/viral culture if oral infection is suspected and treat infection as clinically indicated.

6.5.2.1.7 Skin and Subcutaneous Tissue Disorders

Wound healing and surgery: Cabozantinib has the potential to cause wound healing complications and wound dehiscence which may even occur long after a wound has been considered healed. Therefore, surgical and traumatic wounds must not only be completely healed prior to starting cabozantinib treatment but must also be monitored for wound dehiscence, wound infection and other signs of impaired wound healing while the subject is being treated with cabozantinib. If dehiscence occurs, cabozantinib treatment should not be restarted until complete healing has taken place.

Treatment with cabozantinib should be stopped at least 28 days prior to scheduled surgery. The decision to resume treatment with cabozantinib after surgery should be based on clinical judgment of adequate wound healing.

Palmar-plantar erythrodysesthesia (PPE; also known as hand-foot syndrome), skin rash (including blister, erythematous rash, macular rash, skin exfoliation, dermatitis acneiform, and papular rash), pruritus, dry skin, erythema, pigmentary changes, and alopecia have been reported with cabozantinib. All subjects on study should be advised on prophylactic measures including the use of emollients, removal of calluses, avoidance of exposure of hands and feet to hot water leading to vasodilatation, protection of pressure-sensitive areas of hands and feet, and use of cotton gloves and socks to prevent injury and keep the palms and soles dry.

Early manifestations include tingling, numbness, mild hyperkeratosis, and symmetrical red and swollen res on the palms and soles. The lateral sides of the fingers or periungual zones may also be affected. Adequate interventions are required to prevent worsening of skin symptoms such as blisters, desquamations, ulcerations, or necrosis of affected areas. Analgesics may be required for pain control.

Aggressive management of symptoms is recommended, including early dermatology referral. Treatment recommendations in response to PPE are summarized in Table 6-9.

TABLE 6-9

Management of Palmar-plantar Erythrodysesthesia (PPE) Associated with Cabozantinib

| CTCAE v.4.0 Grade | Action To Be Taken |
|---|---|
| Grade 1 | Cabozantinib treatment may be continued at the current dose if PPE is clinically insignificant and tolerable. Otherwise, cabozantinib should be reduced to the next lower dose level.[a] Start urea 20% cream twice daily |
| Grade 2 | AND clobetasol 0.05% cream once daily. Reassess at least weekly; if PPE worsens at any time or does not improve after 2 weeks, proceed to the intervention guidelines for Grade 2. |
| | Cabozantinib treatment may be continued if PPE is tolerated. Cabozantinib should be dose reduced or interrupted if PPE is intolerable. Continue urea 20% cream twice daily AND high potency steroid cream (eg, clobetasol 0.05%) once daily and add analgesics (eg, NSAIDs/gamma-aminobutyric acid agonists) for pain control if needed. Reassess at least weekly; if PPE worsens or affects self-care, proceed to the intervention guidelines for Grade 3. |

TABLE 6-9-continued

Management of Palmar-plantar Erythrodysesthesia (PPE) Associated with Cabozantinib

| CTCAE v.4.0 Grade | Action To Be Taken |
|---|---|
| Grade 3 | Interrupt cabozantinib treatment until severity decreases to Grade 1 or 0. Continue treatment of skin reaction with high potency steroid cream (eg, clobetasol 0.05%) twice daily AND analgesics. Resume study drug at a reduced dose if PPE recovers to Grade ≤ 1. Discontinue subject from study treatment if PPE does not improve within 6 weeks. |

CTCAE, Common Terminology Criteria for Adverse Events;
NSAID, non-steroidal anti-inflammatory drug;
PPE, palmar plantar erythrodysesthesia.
[a]Permitted dose levels are defined by individual protocols.

6.5.2.1.8 Osteonecrosis

Osteonecrosis has been reported in subjects treated with cabozantinib. Additional risk factors include use of bisphosphonates and denosumab, chemotherapy and anti-angiogenic drugs, use of corticosteroids, local radiotherapy, and dental or orofacial surgery procedures.

Osteonecrosis of the jaw (ONJ) can manifest as jaw pain, osteomyelitis, osteitis, bone erosion, tooth or periodontal infection, toothache, gingival ulceration, or gingival erosion. Persistent pain or slow healing of the mouth or jaw after dental surgery may also be manifestations of osteonecrosis.

Advise subjects regarding oral hygiene practice and to quickly report symptoms to investigator. Caution should be used in subjects receiving bisphosphonates.

Invasive dental procedures should be avoided. In cases where dental procedures are unavoidable, treatment with cabozantinib should be interrupted for at least 4 weeks prior to the procedure and resumed after complete wound healing has occurred. Bone healing may often require a protracted time.

6.5.2.1.9 Proteinuria

Proteinuria has been reported with cabozantinib. Proteinuria should be monitored by measuring UPCR. Table 6-10 provides treatment guidelines for proteinuria deemed related to cabozantinib.

Cabozantinib should be discontinued in subjects who develop nephrotic syndrome (proteinuria >3.5 grams per day in combination with low blood protein levels, high cholesterol levels, high triglyceride levels, and edema).

TABLE 6-10

Management of Proteinuria Associated with Cabozantinib

| Severity of Proteinuria Proteinuria (UPCR) | Management of |
|---|---|
| ≤1 mg/mg (≤113.1 mg/mmol) | No change in cabozantinib treatment or monitoring |
| For RCC, CRPC, NSCLC: >1 and <3.5 mg/mg (>113.1 and <395.9 mg/mmol) For UC: >2 and <3.5 mg/mg (>226.2 and <395.9 mg/mmol) | Consider confirming with a 24-h protein assessment within 7 days. No change in cabozantinib treatment required if UPCR ≤2 mg/mg or urine protein ≤2 g/24 h on 24-h urine collection. Dose reduce or interrupt cabozantinib treatment if UPCR >2 mg/mg on repeat UPCR testing or urine protein >2 g/24 h on 24-h urine collection. Continue cabozantinib on a reduced dose if UPCR decreases to <2 mg/mg. Consider interrupting cabozantinib treatment if UPCR remains >2 mg/mg despite a dose reduction until UPCR decreases to <2 mg/mg. Restart cabozantinib treatment at a reduced dose after a dose interruption unless otherwise approved by sponsor. If UPCR >2 mg/mg, repeat UPCR monitoring within 7 days and once per week. If UPCR <2 mg/mg on 2 consecutive readings, UPCR monitoring can revert to protocol-specific times. (Second reading is confirmatory and can be done within 1 week of first reading.) |
| ≥3.5 mg/mg (≥395.9 mg/mmol) | Interrupt cabozantinib treatment pending repeat UPCR monitoring within 7 days and/or 24-h urine protein. If ≥3.5 mg/mg on repeat UPCR monitoring, continue to interrupt cabozantinib treatment and check UPCR every 7 days. If UPCR decreases to <2 mg/mg, restart cabozantinib treatment at a reduced dose and monitoring of UPCR until it remains <2 mg/mg on two consecutive measurements. If UPCR monitoring is determined to be stable (<20% change) for 1 month then continue with UPCR monitoring per protocol or as clinically indicated. |
| Nephrotic syndrome | Discontinue cabozantinib treatment |

RCC, renal cell carcinoma; UC, urothelial carcinoma; UPCR, urine protein/creatinine ratio.

6.5.2.1.10 Nervous System Disorders

Cabozantinib appears to represent minimal risk of adverse neurological effects based on nonclinical Good Laboratory Practice (GLP)-compliant toxicology studies. Dysphonia, dysgeusia, headache, dizziness, confusional state, convulsion, depression, memory impairment, hypoesthesia, peripheral neuropathy, insomnia, ataxia, and encephalopathy have been observed in clinical studies with cabozantinib. The development of any new or progressive, unexplained neurological symptoms should be assessed for underlying causes.

RPLS has been reported. RPLS should be considered in any subject presenting with seizures, headache, visual disturbances, confusion or altered mental function. Cabozantinib treatment should be discontinued in subjects with RPLS.

6.5.2.1.11 Hepatocellular Toxicity

Evaluations of aminotransferases (ALT and AST) and bilirubin have been observed during treatment with cabozantinib. It is recommended that subjects with elevation of ALT, AST, and/or bilirubin have more frequent laboratory monitoring of these parameters. If possible, hepatotoxic concomitant medications should be discontinued in subjects who develop increased values of ALT, AST, or bilirubin and other causes (eg, cancer related) should be evaluated.

6.5.2.1.13 Blood and Lymphatic System Disorders

Hematological toxicities (ie, neutropenia and thrombocytopenia) and associated complications have been observed after administration of cabozantinib and may be managed with dose interruptions and/or dose reductions. Subjects with hematologic toxicities may require additional or more frequent laboratory tests according to institutional guidelines.

Dose reductions or dose interruptions for hematological toxicities are not mandated but can be applied as clinically indicated. Supportive care for thrombocytopenia or anemia, such as transfusions, may be managed according to institutional guidelines. The use of colony-stimulating growth factors should be considered. Febrile neutropenia or evidence of infection associated with neutropenia must be assessed immediately and treated appropriately and in a timely manner according to institutional guidelines.

6.5.2.1.14 Fatigue

Common causes of fatigue, such as anemia, deconditioning, emotional distress (depression and/or anxiety), poor nutrition, dehydration, sleep disturbance, and hypothyroidism should be ruled out and treated according to standard of

TABLE 6-11

Management of Hepatotoxicity Associated with Cabozantinib

| Severity of ALT, AST, total bilirubin Elevations by CTCAE | Treatment/Cabozantinib Dose Modification |
|---|---|
| Grade 1 | Dose adjustment is usually not required. Consider discontinuing concomitant hepatotoxic medications and add supportive care as indicated. |
| Grade 2 | Interrupt cabozantinib if lasting longer than 1 week. Restart cabozantinib after lab abnormalities have resolved to at least CTCAE Grade <1 or baseline. |
| Grade ≥ 3 | Interrupt cabozantinib and consider more frequent monitoring of ALT, AST, and bilirubin. Restart cabozantinib at a reduced dose after lab abnormalities have resolved to at least CTCAE Grade <1 or baseline. Discontinue if lab abnormalities cannot be reversed despite interruption of cabozantinib. |

ALT, alanine aminotransferase;
AST, aspartate aminotransferase;
CTCAE, Common Terminology Criteria for Adverse Events The following conditions require discontinuation of cabozantinib unless these laboratory abnormalities have recovered to Grade 1 or baseline level after an interruption and the sponsor has approved reinstitution of cabozantinib:

Drug-related ALT or AST >8×ULN.

Drug-related ALT or AST >3×ULN in combination with total bilirubin >2×ULN without reasonable other explanation, consistent with drug-induced liver injury.

Elevations of aminotransferases when hepatic metastases are present may not require dose modifications if there are no progressive changes in the aminotransferases (less than a doubling) and if there are no progressive elevations in serum bilirubin concentration or coagulation factors.

6.5.2.1.12 Infections and Infestations

Infections are commonly observed in cancer subjects. Predisposing risk factor include a decreased immune status (eg, after myelosuppressive anticancer therapies, splenectomy), destructive growth of the underlying malignancy including bone marrow infiltration with suppression of normal hematopoiesis, as well as the presence of IV devices.

care. Pharmacological management should be considered after disease specific morbidities have been excluded when not prohibited.

6.5.2.1.15 Weight Loss

Anorexia and weight loss should be managed according to local standard of care including nutritional support. Pharmacologic therapy should be considered for appetite enhancement when not prohibited by a particular protocol.

6.5.2.1.16 Corrected QT Prolongation

The effect of orally administered cabozantinib 140 mg qd on QTc interval was evaluated in a placebo-controlled study in subjects with medullary thyroid cancer (MTC). A mean increase in QTcF of 10-15 ms was observed after 4 weeks after initiating cabozantinib treatment. A concentration-QTc relationship could not be definitively established. Changes in cardiac wave form morphology or new rhythms were not observed. No cabozantinib-treated subjects in this study had a QTcF >500 ms. Review of the larger safety database (approximately 5000 subjects exposed to cabozantinib in clinical trials and in post-marketing experience) confirmed the absence of safety concerns associated with QT prolongation. There were no events of torsades de pointes reported.

Concomitant treatment with strong cytochrome P450 (CYP) 3A4 inhibitors, which may increase cabozantinib plasma concentrations, should be avoided.

If at any time on study there is an increase in QTcF to an absolute value >500 ms, two additional ECGs must be performed with intervals not less than 3 min apart within 30 min after the initial ECG.

If the average QTcF from the three ECGs is >500 ms, the following actions must be taken:

Interrupt cabozantinib treatment

Immediately notify the Sponsor

Hospitalize symptomatic subjects (eg, with palpitations, dizziness, syncope, orthostatic hypotension, a significant ventricular arrhythmia on ECG) for a thorough cardiology evaluation and management Consider cardiology consultation for asymptomatic subjects for evaluation and management Check electrolytes, especially magnesium, potassium and calcium; correct abnormalities as clinically indicated Check concomitant medications for any medication that may have contributed to QT prolongation, and if possible, discontinue these medications (http://www.qt-drugs.org)

Repeat ECG triplicates hourly until the average QTcF is ≤500 msec, or otherwise determined by consultation with a cardiologist or appropriate expert.

Subjects with QTc prolongation and symptoms must be monitored closely until the QTc elevation and symptoms have resolved. Cabozantinib treatment may be restarted at a reduced dose level if all of the following conditions are met:

Symptoms are determined to be unrelated to the QT interval prolongation

The QTcF value >500 ms is not confirmed

Cabozantinib treatment has been interrupted through a minimum of 1 week following the return of the QTcF to ≤500 ms.

QT prolongation can be unequivocally associated with an event other than cabozantinib administration and is treatable/has been resolved Sponsor has reviewed all available information and has agreed to the continuation of study treatment Following reinitiation of study treatment, ECGs must be repeated weekly for 2 weeks, then every 2 weeks for 1 month, then according to the protocol-defined time points.

Cabozantinib treatment must be permanently discontinued if either of the following applies:

Cardiac evaluation confirms that symptoms we the consequence of QT interval prolongation Recurrence of QTcF prolongation after reinitiation of study treatment at a reduced dose 6.5.2.1.17 Electrolyte Disorders Serum electrolyte disorders including hyponatremia, hypokalemia, hypomagnesemia, and hypophosphatemia have been reported during treatment with cabozantinib, and serum electrolyte levels should be monitored frequently while receiving cabozantinib. Clinically relevant electrolyte disorders should be managed according to the dose modification guidelines as outlined in Table 6-4 or as clinically indicated. Standard clinical practice guidelines should be used for management of electrolyte disorders and may include oral or IV replacement.

6.5.2.1.18 Endocrine Disorders

Treatment-emergent elevation of thyroid-stimulating hormone (TSH) has been observed with cabozantinib treatment. Currently available data are insufficient to determine the mechanism of thyroid function test alterations and its clinical relevance. Management of thyroid dysfunction (eg, symptomatic hypothyroidism) should follow accepted clinical practice guidelines.

6.5.2.2 Atezolizumab

The most common AEs reported in 220% of subjects treated with atezolizumab include fatigue, decreased appetite, nausea, urinary tract infection, pyrexia, and constipation (Tecentriq USPI).

Subjects treated with atezolizumab may also develop infusion-related reactions as well as irAEs such as myocarditis, pneumonitis, hepatitis, colitis, endocrinopathies (hypophysitis, thyroid disorders, adrenal insufficiency, Type 1 diabetes), skin disorders, ocular events, neurological toxicity (myasthenic syndrome/myasthenia gravis, Guillain-Barré syndrome or meningoencephalitis), pancreatitis, and embryo-fetal toxicity. Management guidance for atezolizumab-associated AEs is provided in Sections 6.5.2.2.1 to 6.5.2.2.11.

Systemic immune activation is a rare condition characterized by an excessive immune response. Given the mechanism of action of atezolizumab, systemic immune activation is considered a potential risk when given in combination with other immunomodulating agents. Systemic immune activation should be included in the differential diagnosis for subjects who, in the absence of an alternative etiology, develop a sepsis-like syndrome after administration of atezolizumab, and the initial evaluation should include the following:

Complete blood count (CBC) with peripheral smear

Prothrombin time (PT), partial thromboplastin time (PT, fibrinogen, and D-dimer

Ferritin

Triglycerides

AST, ALT, and total bilirubin

LDH

Complete neurologic and abdominal examination (assess for hepatosplenomegaly)

If systemic immune activation is still suspected after the initial evaluation, contact the Sponsor for additional recommendations.

For details on warnings & precautions, possible AEs and management guidance of AEs, and use in special patient populations refer to the local prescribing Information of atezolizumab and the atezolizumab Investigator's Brochure.

6.52.2.1 Infusion-Related Reaction

In atezolizumab studies identified infusion-related reactions occurred within 24 h of atezolizumab administration and were generally mild to moderate in severity, but severe infusion-related reactions have also occurred. Symptoms associated with atezolizumab infusion may include chills, fever, headache, rash, rigor arthralgias, bronchospasm, arterial hypotension or hypertension. Prophylactic medications are allowed after the initial infusion of atezolizumab. Mild or moderate infusion reactions may require interruptions of the infusion or reductions of the rate of infusion. More severe infusion reactions or recurrent infusion reactions despite prophylactic medication may require permanent discontinuation of atezolizumab. Supportive treatment should be administered at the earliest sign of an infusion reaction according to accepted medical treatment guidelines. Refer to Appendix H for detailed guidance on management and CTCAE grading of infusion-related reactions.

6.5.2.2.2 Immune-Related Pulmonary Evets

Dyspnea, cough, fatigue, hypoxia, pneumonitis, and pulmonary infiltrates have been associated with the administration of atezolizumab. Subjects should be assessed for pulmonary signs and symptoms throughout the study and will also have CT scans of the chest performed at every tumor assessment.

All pulmonary events should be thoroughly evaluated for other commonly reported etiologies such as pneumonia or other infections, lymphangitic carcinomatosis, pulmonary embolism, heart failure, chronic obstructive pulmonary disease, or pulmonary hypertension. Management guidelines for pulmonary events ae provided in Table 6-12.

TABLE 6-12

Management Guidelines for Immune-Related Pulmonary Events, Including Pneumonitis

| Severity of Event | Management |
|---|---|
| Grade 1 | Continue atezolizumab and monitor closely |
| | Re-evaluate on serial imaging |
| | Consider subject referral to pulmonary specialist |
| | For recurrent pneumonitis, treat as a Grade 3 or 4 event |
| Grade 2 | Withhold atezolizumab |
| | Refer subject to pulmonary and infectious disease specialists and consider bronchoscopy or BAL |
| | Initiate treatment with 1-2 mg/kg/day oral prednisone or equivalent. |
| | Resume atezolizumab if event resolves to Grade 1 or better within 12 weeks$^{a,b}$ |
| | Permanently discontinue atezolizumab and contact the Sponsor if event does not resolve to Grade 1 or better within 12 weeks$_{a,b,c}$ |
| | For recurrent events, treat as a Grade 3 or 4 event |
| Grade 3 or 4 | Permanently discontinue atezolizumab and contact the Sponsor$^c$ |
| | Bronchoscopy or BAL is recommended. |
| | Initiate treatment with 1–2 mg/kg/day oral prednisone or equivalent. |
| | If event does not improve within 48 hours after initiating corticosteroids, consider adding an immunosuppressive agent |
| | If event resolves to Grade 1 or better, taper corticosteroids over >1 month |

BAL, bronchoscopic alveolar lavage; IVIG, intravenous immunoglobulin.
$_a$If corticosteroids have been initiated, they must be tapered over >1 month to <10 mg/day oral prednisone or equivalent before atezolizumab can be resumed.
$_b$Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
$_c$Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.3 Immune-Related Hepatic Events

Immune-related hepatitis has been associated with the administration of atezolizumab. Eligible subjects must have adequate liver function, as manifested by measurements of total bilirubin and hepatic transaminases, and liver function will be monitored throughout study treatment. Management guidelines for hepatic events are provided in Table 6-13.

Subjects with right upper-quadrant abdominal pain and/or unexplained nausea or vomiting should have liver function tests (LFTs) performed immediately and reviewed before administration of the next dose of study drug.

For subjects with elevated LFTs, concurrent medication, viral hepatitis, and toxic or neoplastic etiologies should be considered and addressed, as appropriate.

TABLE 6-13

Management Guidelines for Hepatic Events

| Severity of Event | Management |
|---|---|
| Grade 1 | Continue atezolizumab |
| | Monitor LFTs until values resolve to within normal limits |
| Grade 2 | All events: |
| | Monitor LFTs more frequently until return to baseline values Events of >5 days' duration: |
| | Withhold atezolizumab |
| | Initiate treatment with 1–2 mg/kg/day oral prednisone or equivalent |
| | Resume atezolizumab if event resolves to Grade 1 or better within 12 weeks$^{a,b}$ |
| | Permanently discontinue atezolizumab and contact the Sponsor if event does not resolve to Grade 1 or better within 12 weeks$_{a,b,c}$ |
| Grade 3 or 4 | Permanently discontinue atezolizumab and contact the Sponsor$^c$ |
| | Consider subject referral to GI specialist for evaluation and liver biopsy to establish etiology of hepatic injury. |
| | Initiate treatment with 1-2 mg/kg/day oral prednisone or equivalent. |
| | If event does not improve within 48 hours after initiating corticosteroids, consider adding an immunosuppressive agent. |
| | If event resolves to Grade 1 or better, taper corticosteroids over ε 1 month. |

GI, gastrointestinal; LFT, liver function test.
$_a$If corticosteroids have been initiated, they must be tapered over ε 1 month to <10 mg/day oral prednisone or equivalent before atezolizumab can be resumed.
$_b$Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
$_c$Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.4 Immune-Related Colitis or Diarrhea

Immune-related colitis has been associated with the administration of atezolizumab. Management guidelines for diarrhea or colitis are provided in Table 6-14.

All events of diarrhea or colitis should be thoroughly evaluated for other more common etiologies. For events of significant duration or magnitude or associated with signs of systemic inflammation or acute-phase reactants (eg, increased c-reactive protein, platelet count, or bandemia): perform sigmoidoscopy (or colonoscopy, if appropriate) with colonic biopsy, with three to five specimens for standard paraffin block to check for inflammation and lymphocytic infiltrates to confirm colitis diagnosis.

TABLE 6-14

Management Guidelines for Immune-Related Diarrhea or Colitis

| Severity of Event | Management |
|---|---|
| Grade 1 | Continue atezolizumab |
| | Initiate symptomatic treatment |
| | Endoscopy is recommended if symptoms persist for >7 days |
| | Monitor closely |
| Grade 2 | Withhold atezolizumab |
| | Initiate symptomatic treatment |
| | Subject referral to GI specialist is recommended |
| | For recurrent events or events that persist >5 days, initiate treatment with 1-2 mg/kg/day oral prednisone or equivalent |
| | Resume atezolizumab if event resolves to Grade 1 or better within 12 weeks[a,b] |
| | Permanently discontinue atezolizumab and contact the Sponsor if event does not resolve to Grade 1 or better within 12 weeks[a,b,c] |
| Grade 3 | Withhold atezolizumab |
| | Refer subject to GI specialist for evaluation and confirmatory biopsy |
| | Initiate treatment with 1-2 mg/kg/day IV methylprednisolone or equivalent and convert to 1-2 mg/kg/day oral prednisone or equivalent upon improvement |
| | Resume atezolizumab if event resolves to Grade 1 or better within 12 weeks[a,b] |
| | Permanently discontinue atezolizumab and contact the Sponsor if event does not resolve to Grade 1 or better within 12 weeks[a,b,c] |
| Grade 4 | Permanently discontinue atezolizumab and contact the Sponsor[c] |
| | Refer subject to GI specialist for evaluation and confirmation biopsy. |
| | Initiate treatment with 1-2 mg/kg/day IV methylprednisolone or equivalent and convert to 1-2 mg/kg/day oral prednisone or equivalent upon improvement. |
| | If event does not improve within 48 hours after initiating corticosteroids, consider adding an immunosuppressive agent. |
| | If event resolves to Grade 1 or better, taper corticosteroids over ε 1 month. |

GI, gastrointestinal;
IV, intravenous

[a] If corticosteroids have been initiated, they must be tapered over ε 1 month to <10 mg/day oral prednisone or equivalent before atezolizumab can be resumed.
[b] Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
[c] Resumption of atezolizumab may be considered in subjects who are deriving benefit and have fully recovered from the immune-related event. Subjects can be rechallenged with atezolizumab only after approval has been documented by both the Investigator (or an appropriate delegate) and the Sponsor.

6.5.2.2.5 Immune-Related Endocrinopathies

Thyroid disorders, adrenal insufficiency, and hypophysitis have been associated with the administration of atezolizumab. Management guidelines for endocrine events are provided in Table 6-15.

Monitor for signs and symptoms of hypophysitis. Subjects with unexplained symptoms such as fatigue, myalgias, impotence, mental status changes, or constipation should be investigated for the presence of thyroid, pituitary, or adrenal endocrinopathies. The subject should be referred to an endocrinologist if an endocrinopathy is suspected. Thyroid-stimulating hormone (TSH) and free triiodothyronine (T3) and thyroxine (T4) levels should be measured to determine whether thyroid abnormalities are present. TSH, prolactin, and a morning cortisol level will help to differentiate primary adrenal insufficiency from primary pituitary insufficiency.

TABLE 6-15

Management Guidelines for Endocrine Events

| Event | Management |
|---|---|
| Hypophysitis (pan-hypopituitarism) Grade 2-3 | Withhold atezolizumab for up to 12 weeks after event onset[b] |
| | Refer patient to endocrinologist. |
| | Perform brain MRI (pituitary protocol). |

TABLE 6-15-continued

Management Guidelines for Endocrine Events

| Event | Management |
| --- | --- |
|  | Initiate treatment with 1-2 mg/kg/day IV methylprednisolone or equivalent and convert to 1-2 mg/kg/day oral prednisone or equivalent upon improvement. |
|  | Initiate hormone replacement therapy if clinically indicated. |
|  | If event resolves to Grade 1 or better, resume atezolizumab.[b] |
|  | If event does not resolve to Grade 1 or better while withholding atezolizumab, permanently discontinue atezolizumab and contact the Sponsor.[c] |
|  | For recurrent hypophysitis, treat as a Grade 4 event. |
| Hypophysitis (pan-hypopituitarism) Grade 4 | Permanently discontinue atezolizumab and contact the Sponsor. |
|  | Refer patient to endocrinologist. |
|  | Perform brain MRI (pituitary protocol). |
|  | Initiate treatment with 1-2 mg/kg/day IV methylprednisolone or equivalent and convert to 1-2 mg/kg/day oral prednisone or equivalent upon improvement.[a] |
|  | Initiate hormone replacement therapy if clinically indicated. |
| Asymptomatic hypothyroidism | Continue atezolizumab |
|  | Initiate treatment with thyroid replacement hormone |
|  | Monitor TSH weekly |
| Symptomatic hypothyroidism | Withhold atezolizumab |
|  | Initiate treatment with thyroid replacement hormone |
|  | Monitor TSH weekly |
|  | Consider subject referral to endocrinologist. |
|  | Resume atezolizumab when symptoms are controlled and thyroid function is improving |
| Asymptomatic hyperthyroidism | TSH ε 0.1 mU/L and <0.5 mU/L: |
|  | Continue atezolizumab |
|  | Monitor TSH every 4 weeks |
|  | TSH <0.1 mU/L: |
|  | Follow guidelines for symptomatic hyperthyroidism |
| Symptomatic hyperthyroidism | Withhold atezolizumab |
|  | Initiate treatment with anti-thyroid drug such as methimazole or carbimazole as needed |
|  | Consider subject referral to endocrinologist |
|  | Resume atezolizumab when symptoms are controlled and thyroid function is improving |
|  | Permanently discontinue atezolizumab and contact the Sponsor for life-threatening immune-related hyperthyroidism[c] |
| Symptomatic adrenal insufficiency Grade 2–4 | Withhold atezolizumab[a] |
|  | Refer subject to endocrinologist |
|  | Perform appropriate imaging |
|  | Initiate treatment with 1–2 mg/kg/day IV methylprednisolone or equivalent and convert to 1–2 mg/kg/day oral prednisone or equivalent upon improvement. |
|  | Resume atezolizumab if event resolves to Grade 1 or better and subject is stable on replacement therapy (if required) within 12 weeks[a,b] |
|  | Permanently discontinue atezolizumab and contact the Sponsor if event does not resolve to Grade 1 or better or subject is not stable on replacement therapy within 12 weeks[a,b,c] |
| Hyperglycemia Grade 1 or 2 | Continue atezolizumab |
|  | Initiate treatment with insulin if needed |
|  | Monitor for glucose control |
| Hyperglycemia Grade 3 or 4 | Withhold atezolizumab. |
|  | Initiate treatment with insulin. |
|  | Monitor for glucose control. |
|  | Resume atezolizumab when symptoms resolve and glucose levels are stable. |

IV, intravenous; TSH, thyroid-stimulating hormone.

[a]If corticosteroids have been initiated, they must be tapered over ε 1 month to δ 10 mg/day oral prednisone or equivalent before atezolizumab can be resumed.

[b]Atezolizumab may be withheld for a period of time beyond 12 weeks to allow for corticosteroids to be reduced to δ 10 mg/day oral prednisone or equivalent. The acceptable length of the extended period of time must be agreed upon by the investigator and the Sponsor.

[c]Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.6 Immune-Related Dermatologic Events

Treatment-emergent rash has been associated with atezolizumab. The majority of cases of rash were mild in severity and self-limited, with or without pruritus. A dermatologist should evaluate persistent and/or severe rash or pruritus. A biopsy should be considered unless contraindicated. Management guidelines for dermatologic events are provided in Table 6-16.

TABLE 6-16

Atezolizumab Management Guidance of Immune-Related Dermatologic Events

| Severity of Event | Management of Skin Disorder |
| --- | --- |
| Grade 1 | Continue atezolizumab. Consider treatment with topical corticosteroids and/or other symptomatic therapy (eg, antihistamines). |
| Grade 2 | Continue atezolizumab. Consider subject referral to dermatologist. Initiate treatment with topical corticosteroids. Consider treatment with higher-potency topical corticosteroids if event does not improve |
| Grade 3 | Delay atezolizumab. Refer subject to dermatologist. Initiate treatment with 10 mg/day oral prednisone or equivalent, increasing dose to 1-2 mg/kg/day if event does not improve within 48-72 hours. Resume atezolizumab if event resolves to Grade 1 or better within 12 weeks.$^{a,b}$ Permanently discontinue atezolizumab and contact Sponsor if event does not resolve to Grade 1 or better within 12 weeks.$_{a,b,c}$ |
| Grade 4 | Permanently discontinue atezolizumab and contact Sponsor. |

$^d$ If corticosteroids have been initiated, they must be tapered over ≥1 month to <10 mg/day oral prednisone or equivalent before atezolizumab can be resumed.
$_e$ Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
$_f$Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.7 Immune-Related Ocular Events

Treatment-emergent ocular events have been associated with atezolizumab. Management guidelines for ocular events are provided in Table 6-17.

TABLE 6-17

Atezolizumab Management Guidance of Immune-Related Ocular Events

| Severity of Event | Management of Ocular Event |
| --- | --- |
| Grade 1 | Continue atezolizumab. Subject referral to ophthalmologist is strongly recommended. Initiate treatment with topical corticosteroid eye drops and topical immunosuppressive therapy. If symptoms persist, treat as a Grade 2 event. |
| Grade 2 | Delay atezolizumab. Subject referral to ophthalmologist is strongly recommended. Initiate treatment with topical corticosteroid eye drops and topical immunosuppressive therapy. Resume atezolizumab if event resolves to Grade 1 or better within 12 weeks.$^{a,b}$ Permanently discontinue atezolizumab and contact the Sponsor if event does not resolve to Grade 1 or better within 12 weeks.$_{a,b,c}$ |
| Grade 3 or 4 | Permanently discontinue atezolizumab and contact the Sponsor.$^c$ Refer subject to ophthalmologist. Initiate treatment with 1-2 mg/kg/day oral prednisone or equivalent. If event resolves to Grade 1 or better, taper corticosteroids over ≥1 month. |

$_a$If corticosteroids have been initiated, they must be tapered over ≥1 month to <10 mg/day oral prednisone or equivalent before atezolizumab can be resumed.
$_b$Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
$_c$Resumption of atezolizumab may be considered in subjects who are deriving benefit and have fully recovered from the immune-related event. Subjects can be rechallenged with atezolizumab only after approval has been documented by both the investigator (or designee) and the Sponsor.

6.5.2.2.8 Immune-Related Meningoencephalitis

Immune-related meningoencephalitis is an identified risk associated with the administration of atezolizumab. Immune-related meningoencephalitis should be suspected in any subject presenting with signs or symptoms suggestive of meningitis or encephalitis, including, but not limited to, headache, neck pain, confusion, seizure, motor or sensory dysfunction, and altered or depressed level of consciousness. Encephalopathy from metabolic or electrolyte imbalances needs to be distinguished from potential meningoencephalitis resulting from infection (bacterial, viral, or fungal) or progression of malignancy, or secondary to a paraneoplastic process.

All subjects being considered for meningoencephalitis should be urgently evaluated with a CT scan and/or MRI scan of the brain to evaluate for metastasis, inflammation, or edema. If deemed safe by the treating physician, a lumbar puncture should be performed and a neurologist should be consulted.

Subjects with signs and symptoms of meningoencephalitis, in the absence of an identified alternate etiology, should be treated according to the guidelines in Table 6-18.

TABLE 6-18

Management Guidelines for Immune-Related Meningoencephalitis

| Severity of Event | Management |
|---|---|
| All grades | Permanently discontinue atezolizumab and contact the Sponsor[a]<br>Refer subject to neurologist<br>Initiate treatment with 1–2 mg/kg/day IV methylprednisolone or equivalent and convert to 1–2 mg/kg/day oral prednisone or equivalent upon improvement<br>If event does not improve within 48 hours after initiating corticosteroids, consider adding an immunosuppressive agent<br>If event resolves to Grade 1 or better, taper corticosteroids over ε 1 month |

IV, intravenous.

[a]Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.9 Immune-Related Motor and Sensory Neuropathy

Myasthenia gravis and Guillain-Barré syndrome have been observed with single-agent atezolizumab. Patients may present with signs and symptoms of sensory and/or motor neuropathy. Diagnostic work-up is essential for an accurate characterization to differentiate between alternative etiologies. Management guidelines for neurologic disorders are provided in Table 6-19.

TABLE 6-19

Management Guidelines for Immune-Related Neurologic Disorders

| Event | Management |
|---|---|
| Immune-related neuropathy Grade 1 | Continue atezolizumab<br>Investigate etiology |
| Immune-related neuropathy Grade 2 | Withhold atezolizumab<br>Investigate etiology<br>Initiate treatment as per institutional guidelines<br>Resume atezolizumab if event resolves to Grade 1 or better within 12 weeks[a,b]<br>Permanently discontinue atezolizumab and contact the Sponsor if event does not resolve to Grade 1 or better within 12 weeks[a,b,c] |
| Immune-related neuropathy Grade 3 or 4 | Permanently discontinue atezolizumab and contact the Sponsor[c]<br>Initiate treatment as per institutional guidelines. |
| Myasthenia gravis and Guillain-Barré syndrome, any grade | Permanently discontinue atezolizumab and contact the Sponsor[c]<br>Refer subject to neurologist.<br>Initiate treatment as per institutional guidelines.<br>Consider initiation of 1-2 mg/kg/day oral or IV prednisone or equivalent. |

IV, intravenous.

[a]If corticosteroids have been initiated, they must be tapered over ε 1 month to <10 mg/day oral prednisone or equivalent before atezolizumab can be resumed.

[b]Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.

[c]Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.10 Immune-Related Pancreatitis

Symptoms of abdominal pain associated with elevations of amylase and lipase, suggestive of pancreatitis, have been associated with the administration of atezolizumab. The differential diagnosis of acute abdominal pain should include pancreatitis. Appropriate work-up should include an evaluation for ductal obstruction, as well as serum amylase and lipase tests. Management guidelines for pancreatic events, including pancreatitis, are provided in Table 6-20.

TABLE 6-20

Management Guidelines for Pancreatic Events, Including Pancreatitis

| Event | Management |
| --- | --- |
| Amylase and/or lipase elevation, Grade 1 | Continue atezolizumab<br>Monitor amylase and lipase prior to dosing |
| Amylase and/or lipase elevation, Grade 2 | Continue atezolizumab<br>Monitor amylase and lipase weekly<br>For prolonged elevation (eg, >3 weeks), consider treatment with 10 mg/day oral prednisone or equivalent |
| Amylase and/or lipase elevation, Grade 3 or 4 | Withhold atezolizumab<br>Refer subject to GI specialist<br>Monitor amylase and lipase every other day<br>If no improvement, consider treatment with 1–2 mg/kg/day oral prednisone or equivalent<br>Resume atezolizumab if event resolves to Grade 1 or better within 12 weeks$^{a,b}$<br>Permanently discontinue atezolizumab and contact the Sponsor if event does not resolve to Grade 1 or better within 12 weeks$_{a,b,c}$<br>For recurrent events, permanently discontinue atezolizumab and contact the Sponsor$^c$ |
| Immune-related pancreatitis, Grade 2 or 3 | Withhold atezolizumab<br>Refer subject to GI specialist<br>Initiate treatment with 1–2 mg/kg/day IV methylprednisolone or equivalent and convert to 1–2 mg/kg/day oral prednisone or equivalent upon improvement<br>Resume atezolizumab if event resolves to Grade 1 or better within 12 weeks$^{a,b}$<br>Permanently discontinue atezolizumab and contact the Sponsor if event does not resolve to Grade 1 or better within 12 weeks$_{a,b,c}$<br>For recurrent events, permanently discontinue atezolizumab and contact the Sponsor$^c$ |
| Immune-related pancreatitis, Grade 4 | Permanently discontinue atezolizumab and contact the Sponsor$^c$<br>Refer subject to GI specialist.<br>Initiate treatment with 1–2 mg/kg/day IV methylprednisolone or equivalent and convert to 1–2 mg/kg/day oral prednisone or equivalent upon improvement.<br>If event does not improve within 48 hours after initiating corticosteroids, consider adding an immunosuppressive agent.<br>If event resolves to Grade 1 or better, taper corticosteroids over ε 1 month. |

GI, gastrointestinal; IV, intravenous.

$^a$If corticosteroids have been initiated, they must be tapered over ε 1 month to <10 mg/day oral prednisone or equivalent before atezolizumab can be resumed.

$^b$Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.

$^c$Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.11 Immune-Related Myocarditis

Non-fatal myocarditis has been associated with the administration of atezolizumab. Guidelines for management of immune-related myocarditis are presented in Table 6-21.

TABLE 6-21

Management Guidelines for Immune-Related Myocarditis

| Event | Management |
| --- | --- |
| Immune-related myocarditis, Grade 1 | Refer patient to cardiologist<br>Initiate treatment as per institutional guidelines. |
| Immune-related myocarditis, Grade 2 | Withhold atezolizumab for up to 12 weeks after event onset and contact Sponsor. |

TABLE 6-21-continued

Management Guidelines for Immune-Related Myocarditis

| Event | Management |
|---|---|
| | Refer patient to cardiologist<br>Initiate treatment as per institutional guidelines and consider antiarrhythmic drugs, temporary pacemaker, extracorporeal membrane oxygenation (ECMO), or VAD as appropriate.<br>Consider treatment with 1-2 mg/kg/day IV methylprednisolone or equivalent and convert to 1-2 mg/kg/day oral prednisone or equivalent upon improvement.[a]<br>If event resolves to Grade 1 or better, resume atezolizumab.[b]<br>If event does not resolve to Grade 1 or better while withholding atezolizumab, permanently discontinue atezolizumab and contact the Sponsor.[c] |
| Immune-related myocarditis, Grade 3-4 | Permanently discontinue atezolizumab and contact the Sponsor.[c]<br>Refer patient to cardiologist<br>Initiate treatment as per institutional guidelines and consider antiarrhythmic drugs, temporary pacemaker, ECMO, or VAD as appropriate.<br>Initiate treatment with 1-2 mg/kg/day IV methylprednisolone or equivalent and convert to 1-2 mg/kg/day oral prednisone or equivalent upon improvement.[a,b]<br>If event does not improve within 48 hours after initiating corticosteroids, consider adding an immunosuppressive agent.<br>If event resolves to Grade 1 or better, taper corticosteroids over ≥1 month. |

[a]If corticosteroids have been initiated, they must be tapered over ε 1 month to <10 mg/day oral prednisone or equivalent before atezolizumab can be resumed.
[b]Atezolizumab may be withheld for a period of time beyond 12 weeks to allow for corticosteroids to be reduced to <10 mg/day oral prednisone or equivalent. The acceptable length of the extended period of time must be agreed upon by the investigator and the Sponsor.
[c]Resumption of atezolizumab may be considered in subjects who are deriving benefit and have fully recovered from the immune-related event. Subjects can be rechallenged with atezolizumab only after approval has been documented by both the investigator (or an appropriate delegate) and the Sponsor.

6.5.2.2.12 Embryo-Fetal Toxicity

Based on its mechanism of action, atezolizumab can cause fetal harm when administered to a pregnant woman. Animal studies have demonstrated that Inhibition of the PD-L1/PD-1 pathway can lead to increased risk of immune-related rejection of the developing fetus resulting in fetal death. If atezolizumab is used during pregnancy, or if the subject becomes pregnant while taking atezolizumab, advise the subject of the potential risk to a fetus. Advise females of reproductive potential to use effective contraception during treatment with atezolizumab and for at least 5 months after the last dose.

7 Concomitant Medications and Therapies 7.1 Allowed Therapy

Antiemetics and antidiarrheal medications are allowed prophylactically according to standard clinical practice if clinically indicated.

Granulocyte colony-stimulating factors (G-CSF or GM-CSF) are allowed if used per clinical guidelines (eg, ASCO or ESMO guidelines).

Bisphosphonates can be used to control bone loss or hypocalcemia if the benefit outweighs the risk per the investigator's discretion (Section 6.5.2.1.8).

Note: osteonecrosis of the jaw has been reported in subjects using bisphosphonates. Oral examinations are recommended at screening to determine eligibility and periodically during the study. In addition, subjects should be advised regarding oral hygiene practice and to quickly report symptoms to the investigator. Frequent monitoring for potentially overlapping toxicities with study treatment is recommended.

Transfusions and hormone replacement should be utilized as indicated by standard clinical Practice.

Inhaled or intranasal corticosteroids are allowed if minimal systemic absorption. Systemic corticosteroids are allowed for control of infusion reactions or irAEs and must be tapered to a dose level ≤10 mg/day of prednisone equivalent before next atezolizumab administration. Prophylactic steroid treatment for subjects with contrast allergies prior to tumor imaging is allowed.

Individualized anticoagulation therapy with heparin is allowed if it can be provided safely and effectively under the following circumstances:

Low dose low molecular weight heparins (LMWH) for prophylactic use are allowed if clinically indicated and the benefit outweighs the risk per the investigator's discretion.

Therapeutic dose of LMWH at the time of the first dose of study treatment are allowed if the subject has no evidence of brain metastasis, has been on a stable dose of LMWH for at least 6 weeks, and has had no complications from a thromboembolic event or the anticoagulation regimen.

Therapeutic does of LMWH after first don of study treatment ae allowed if clinically indicated (eg, for the treatment of DVT), and the benefit outweighs the risk per the investigator's discretion. For management of thromboembolic complications while on study, refer to Section 6.5.2.1.4.

Accepted clinical guidelines regarding appropriate management while receiving anticoagulation therapy with heparins must be followed. This includes, but is not limited to, subject education regarding potential adverse drug reactions, monitoring laboratory parameters, dose adjustments (eg, due to kidney dysfunction).

For restrictions on oral anticoagulants see Section 7.2.

Potential drug interactions with cabozantinib are summarized in Section 7.3.1. The drug interaction potential of atezolizumab is unknown. Refer to the local prescribing information and the atezolizumab Investigator's Brochure.

7.2 Prohibited or Restricted Therapy

The following therapies are prohibited until study treatment has been permanently discontinued:

Any investigational agent or investigational medical device.

Therapeutic doses of oral anticoagulants (eg, warfarin or other coumarin-related agents, direct thrombin or direct FXa inhibitors, or antiplatelet agents such as clopidogrel, or chronic use of aspirin above low dose levels for cardioprotection per local applicable guidelines).

Any nonprotocol systemic anticancer treatment (eg, chemotherapy, immunotherapy, radionuclides, drugs or herbal products used specifically for the treatment of the cancer under investigation).

Concomitant use of denosumab with atezolizumab is prohibited due to a potential for increased risk of infections.

The following therapies should be avoided until study treatment has been permanently discontinued or until otherwise specified.

Local anticancer treatment including palliative radiation, ablation, embolization, or surgery with impact on tumor lesions should not be performed until radiographic progression per RECIST 1.1 has been established. If clinically unavoidable the investigator should consult the Sponsor prior to the procedure for safety guidance.

Erythropoietic stimulating agents (eg, epoetin alfa and darbepoetin alfa) should not be used based on a report of increased risk of tumor recurrence/progression associated with erythropoietin (Wright et al 2007).

Concomitant medications that are known to prolong the QTc interval should be avoided in subjects who receive cabozantinib until they have permanently discontinued cabozantinib treatment (refer to http://wwww.qt-drugs.org for a list of drugs which have the potential to prolong the QTc interval).

Live vaccines are prohibited while on study and until 5 months after last atezolizumab dose (eg, intranasal Influenza, measles, mumps, rubella, oral polio, Bacillus Calmette-Guérin, yellow fever, varicella, and TY21a typhoid vaccines). The use of inactivated (killed) vaccines for the prevention of infectious disease requires sponsor approval.

Chronic co-administration of cabozantinib with strong inducers of the CYP3A4 family (eg, phenyloin, carbamazepine, rifampin, rifabutin, rifapentine, phenobarbital, and St. John's Wort) may significantly decrease cabozantinib concentrations and should be avoided. Selection of alternate concomitant medications with no or minimal CYP3A4 enzyme induction potential is recommended.

Caution must be used when discontinuing treatment with a strong CYP3A4 inducer in a subject who has been concurrently receiving a stable dose of cabozantinib, as this could significantly increase the exposure to cabozantinib.

Co-administration of cabozantinib with strong inhibitors of the CYP3A4 family (eg, boceprevir, conivaptan, posaconazole, ketoconazole, itraconazole, clarithromycin, atazanavir, indinavir, nefazodone, nelfinavir, saquinavir, ritonavir, lopinavir, telaprevir, telithromycin, and voriconazole) may increase cabozantinib concentrations and should be avoided. Grapefruit, star fruit, and Seville oranges may also increase plasma concentrations of cabozantinib and should be avoided.

Additional information on potential drug interactions with cabozantinib is provided in Section 7.3.1.

Refer to the local prescribing information and the atezolizumab Investigator's Brochure for drugs to be avoided when taking atezolizumab.

7.3 Potential Drug Interactions 7.3.1 Potential Drug Interactions with Cabozantinib Cytochrome P450: Data from a clinical drug Interaction study (Study XL184-008) show that clinically relevant steady-state concentrations of cabozantinib appear to have no marked effect on the area under the plasma concentration-vs-time curve (AUC) of co-administered rosiglitazone, a CYP2C8 substrate. Therefore, cabozantinib is not anticipated to markedly inhibit CYP2C8 in the clinic, and by inference, is not anticipated to markedly inhibit other CYP450 isozymes that have lower [I]/Ki values compared with CYP2C8 (ie, CYP2C9, CYP2C19, CYP2D6, CYP1A2, and CYP3A4). In vitro data indicate that cabozantinib is unlikely to Induce cytochrome P450 enzymes, except for possible induction of CYP1A1 at high cabozantinib concentrations (30 µM).

Cabozantinib is a CYP3A4 substrate and a weak substrate for CYP2C9 (but not a CYP2D6, CYP2C8, CYP2C19, CYP2B6, or CYP1A2 substrate), based on data from in vitro studies. Results from a clinical pharmacology study, XL184-006, showed that concurrent administration of cabozantinib with the strong CYP3A4 inducer, rifampin, resulted in an approximately 77% reduction in cabozantinib exposure (AUC values) after a single dose of cabozantinib in healthy volunteers. Chronic co-administration of cabozantinib with strong inducers of the CYP3A4 family (eg, phenyloin, carbamazepine, rifampin, rifabutin, rifapentine, phenobarbital, and St. John's Wort) may significantly decrease cabozantinib concentrations. The chronic use of strong CYP3A4 inducers should be avoided. Other drugs that induce CYP3A4 should be used with caution because these drugs have the potential to decrease exposure (AUC) to cabozantinib. Selection of alternate concomitant medications with no or minimal CYP3A4 enzyme induction potential is recommended.

Results from a clinical pharmacology study, XL184-007, showed that concurrent administration of cabozantinib with the strong CYP3A4 inhibitor, ketoconazole, resulted in a 38% increase in the cabozantinib exposure (AUC values) after a single dose of cabozantinib in healthy volunteers. Co-administration of cabozantinib with strong inhibitors of the CYP3A4 family (eg, boceprevir, conivaptan, posaconazole, ketoconazole, itraconazole, clarithromycin, atazanavir, indinavir, nefazodone, nelfinavir, saquinavir, ritonavir, lopinavir, telaprevir, telithromycin, and voriconazole) may increase cabozantinib concentrations. Grapefruit, star fruit and Seville oranges may also increase plasma concentrations of cabozantinib and should be avoided. Strong CYP3A4 inhibitors should be avoided and other drugs that inhibit CYP3A4 should be used with caution because these drugs have the potential to increase exposure (AUC) to cabozantinib. Selection of alternate concomitant medications with no or minimal CYP3A4 enzyme inhibition potential is recommended.

Please refer to the drug interaction tables at the following websites for lists of substrates, inducers, and inhibitors of selected CYP450 isozyme pathways: Http://medicine.iupui.edu/clinpharm/ddis/hable.aspx: http://vwww.fda.gov/Drugs/DevelopmenApprovalProcess/DmveopmentResource/DrugIn Protein Binding: Cabozantinib is highly bound (99.7%) to human plasma proteins. Therefore, highly protein bound drugs should be used with caution with cabozantinib because there is a potential displacement interaction that could increase free concentrations of cabozantinib and/or a co-administered highly protein-bound drug (and a corresponding increase in pharmacologic effect).

Other Interactions: Food may increase exposure levels of cabozantinib by 57%, fasting recommendations should be followed. In vitro data suggest that cabozantinib is unlikely to be a substrate for P-glycoprotein, but it does appear to have the potential to inhibit the P-glycoprotein transport activity. Therefore, cabozantinib may have the potential to increase plasma concentrations of co-administered substrates of P-glycoprotein. Additional details related to these overall conclusions can be found in the investigator brochure.

Administration of the proton pump inhibitor (PPI) esomeprazole resulted in no clinically-relevant effect on cabozantinib plasma PK in healthy volunteers. Therefore, concomitant use of gastric pH modifying agents (ic, PPIs, $H_2$ receptor antagonists, and antacids) is not contraindicated in subjects administered cabozantinib.

Additional details regarding potential drug interactions with cabozantinib can be found in the Investigator brochure.

7.3.2 Potential Drug Interactions with Atezolizumab

Cytochrome P450 enzymes, as well as conjugation/glucuronidation reactions, are not involved in the metabolism of atezolizumab. No drug interaction studies for atezolizumab have been conducted. There are no known interactions with other medicinal products or other form of interactions. For additional details refer to the local prescribing information and the atezolizumab Investigator's Brochure.

8 Safety 8.1 Adverse Events and Laboratory Abnormalities 8.1.1 Adverse Events

An AE is any untoward medical occurrence in a patient or clinical investigation subject who has been enrolled in a clinical study and who may have been administered an investigational product, regardless of whether or not the event is assessed as related to the study treatment. An AE can therefore be any unfavorable and unintended sign (Including an abnormal laboratory finding), symptom, or disease temporally associated with the use of an investigational product, regardless of whether or not the event is assessed as related to the investigational product. Pro-existing medical conditions that worsen during a study will be recorded as AEs. Abnormal laboratory values, ECG findings, or vital signs ae to be recorded as AEs if they meet the criteria described in Section 8.2.

All untoward events that occur after informed consent through 30 days (90 days for AESIs) after the date of the decision to permanently discontinue study treatment are to be recorded by the investigational site.

At each scheduled and unscheduled visit, AEs are to be identified and assed based upon study procedures, routine and symptom-directed clinical investigations, and subject query/report.

Assessment of the relationship of the AEs to study treatment by the investigator will be based on the following two definitions:

Not Related: An event is assessed as not related to study treatment if it is attributable to another cause and/or there is no evidence to support a causal relationship.

Related: An event is assessed as related to study treatment when there is a reasonable possibility that study treatment caused the event. Reasonable possibility means there is evidence to suggest a causal relationship between study treatment and the event. This event is called a suspected adverse reaction. A suspected adverse reaction implies a lesser degree of certainty about causality than adverse reaction, which means any AE caused by a drug.

8.1.2 Laboratory Abnormalities

All laboratory data required by this protocol and any other clinical investigations will be reviewed. Any abnormal value that leads to a change in subject management (eg, dose reduction or delay or requirement for additional medication or monitoring) or that is considered to be of clinical significance by the investigator will be reported as an AE or SAE as appropriate, unless this value is consistent with the subject's present disease state or is consistent with values obtained prior to entry into the study.

8.2 Serious Adverse Events

The SAE definition and reporting requirements are in accordance with the International Conference on Harmonisation (ICH) Guideline for Clinical Safety Data Management: Definitions and Standards for Expedited Reporting, Topic E2A.

An SAE is defined a many untoward medical occurrence that at any dose

Results in death.

Is immediately life-threatening (Ie, in the opinion of the investigator, the AE places the subject at immediate risk of death; it does not include a reaction that, had it occurred in a more severe form, might have caused death).

Requires inpatient hospitalization or results in prolongation of an existing hospitalization.

Results in significant incapacity or substantial disruption of the ability to conduct normal life functions.

Is a congenital anomaly or birth defect.

Is an important medical event that may not be immediately life-threatening, result in death, or require hospitalization, but may be considered an SAE when, based upon appropriate medical judgment, it jeopardizes the subject or may require medical or surgical intervention to prevent one of the outcomes listed above.

As soon as an Investigator becomes aware of an AE that meets the criteria for an SAE, the investigator will document the SAE to the extent that information is available.

SAEs, regardless of casual relationship, must be reported to the Sponsor or designee within 24 hours of the investigators's knowledge of the event by submitting the completed SAE report form and any other pertinent SAE information as indicated on the SAE Reporting form (or in the SAE Reporting form Completion Guidelines) and confirming the report was received Forms for reporting SAEs and contact information will be provided to the study sites.

SAEs that must be recorded on an SAE Reporting form include the following:

All SAEs that occur after informed consent and through 30 days (90 days for AESIs) after the date of the decision to permanently discontinue study treatment (or the date the subject is deemed to be a screen failure).

Any SAEs assessed as related to study treatment or study procedures, even if the SAE occurs more than 30 days after the date of the decision to permanently discontinue study treatment.

Note: If the subject does not meet the eligibility criteria during screening, then SAEs only need to be reported from the time the subject signs the informed consent until the day when the subject has been determined to not be eligible for study participation.

SAEs that occur after the initiation of study treatment through 30 days (90 days for AESIs) after the date of the decision to permanently discontinue of study treatment must also be recorded on the CRF page.

The minimum information required for SAE reporting includes identity of investigator, site number, subject number, and an event description. Other Important information requiring timely reporting are the SAE term(s), the reason why the event is considered to be serious (ie, the seriousness criteria), and the investigator's assessment of the relationship of the event to study treatment. Additional SAE information including medications or other therapeutic measures used to treat the event, action taken with the study treatment because of the event, and the outcome/resolution of the event will be recorded on the SAE form.

In all cases the investigator should continue to monitor the clinical situation and report all material facts relating to the progression or outcome of the SAE. Furthermore, the investigator may be required to provide supplementary information as requested by the Sponsor's Drug Safety personnel or designee.

When reporting SAEs, the following additional points will be noted:

When the diagnosis of an SAE is known or suspected, the investigator will report the diagnosis or syndrome as the primary SAE term, rather than as signs or symptoms. Signs and symptoms may then be described in the event description.

Death will not be reported as an SAE, but as an outcome of a specific SAE, unless the event preceding the death is unknown. Terms of "Unexplained Death" or "Death from unknown origin" may be used when the cause is unknown. In these circumstances the cause of death must be investigated and the diagnosis amended when the etiology has been identified. If an autopsy was performed, the autopsy report should be provided.

While most hospitalizations necessitate reporting of an SAE, some hospitalizations do not require SAE reporting, as follows:

Elective or previously scheduled surgeries or procedures for preexisting conditions that have not worsened after initiation of treatment (eg, a previously scheduled ventral hernia repair). SAEs must, however, be reported for any surgical or procedural complication resulting in prolongation of the hospitalization.

Prespecified study hospitalizations for observation.

Events that result in hospital stays of fewer than 24 hours and that do not require admission (eg, an emergency room visit for hematuria that results in a diagnosis of cystitis and discharge to home on oral antibiotics).

8.3 Adverse Events of Special Interest for Atezolizumab

Adverse events of special interest (AESIs) for atezolizumab consist of immune-mediated adverse events associated with CIs, cases of potential drug-induced liver injury, and suspected transmission of an infectious agent by the study treatment (Table 8-1).

AESIs will be reported to the Sponsor or designee using the SAE reporting form irrespective of whether the event is serious or nonserious; all AESIs must be reported within 24 hours using the SAE process as described in Section 8.2.

Guidance for management of immune-mediated adverse events associated with atezolizumab is provided in the protocol (Section 6.5.2.2) and can also be found in the local prescribing information and atezolizumab Investigator's Brochure.

TABLE 8-1

Adverse Events of Special Interest for Atezolizumab

Cases of potential DILI that include an elevated ALT or AST in combination with either an elevated bilirubin or clinical jaundice, as defined by Hy's Law and based on the following observations:
    Treatment-emergent ALT or AST >3 × baseline value in combination with total bilirubin >2 × ULN (of which ≥35% is direct bilirubin)
    Treatment-emergent ALT or AST >3 × baseline value in combination with clinical jaundice
Suspected transmission of an infectious agent by the study treatment, as defined below
    Any organism, virus, or infectious particle (eg, prion protein transmitting transmissible spongiform encephalopathy), pathogenic or non-pathogenic, is considered an infectious agent. A transmission of an infectious agent may be suspected from clinical symptoms or laboratory findings that indicate an infection in a patient exposed to a medicinal product. This term applies only when a contamination of study treatment is suspected.
Pneumonitis
Colitis
Endocrinopathies: diabetes mellitus, pancreatitis, adrenal insufficiency, hyperthyroidism, and hypophysitis
Hepatitis, including AST or ALT >10 × ULN
Systemic lupus erythematosus
Neurological disorders: Guillain-Barré syndrome, myasthenic syndrome or myasthenia gravis, and meningoencephalitis
Events suggestive of hypersensitivity, infusion-related reactions, cytokine release syndrome, influenza-like illness, systemic inflammatory response syndrome, and systemic immune activation
Nephritis
Ocular toxicities (eg, uveitis, retinitis)
Myositis
Myopathies, including rhabdomyolysis
≥Grade 2 cardiac disorders (eg, atrial fibrillation, myocarditis, pericarditis)
Vasculitis ALT, alanine aminotransferase; AST, aspartate aminotransferase; DILI, drug-induced liver injury; ULN, upper limit of normal.

8.3.1 General Information on Immune-Related Adverse Events

The immune-modulating properties of checkpoint-inhibitors, such as the anti-PD-L1 antibody atezolizumab, are able to unbalance the Immunologic tolerance and generate a subset of AEs (called irAEs) with an autoimmune inflammatory pathomechanism. IrAEs may involve every organ or tissue (Michot et al 2016). Most irAEs occur within the first 12 weeks of exposure to ICIs but some of them may appear with a delayed onset. Diagnosis of irAEs should be based on exposure to an ICI and a reasonable immune-based mechanism of the observed AE. Whenever possible, histologic examination or other immune-based diagnostic evaluations should be used to support the diagnosis. Other etiologic causes including AEs from tumor progression should be ruled out The spectrum of irAEs is wide and can be general or organ-specific. Examples of general IrAEs in subjects treated with ICIs are fatigue, fever, and chills. Organ-specific irAEs consist of dermatitis (rash, pruritus, vitiligo, oral mucositis, and gingivitis), enterocolitis (diarrhea with abdominal pain and clinical or radiological evidence of colonic inflammation), and endocrinopathies (pituitary, thyroid, adrenal, testes). Diagnosis of endocrine dysfunction is challenging with relatively unspecific symptoms. Additional laboratory testing of the endocrine axes may be helpful: prolactin (pituitary-hypothalamic function), T4 and TSH (pituitary-thyroid function), luteinizing hormone (LH) and follicle-stimulating hormone (FSH) (pituitary-gonadal function), adrenocorticotropic hormone (ACTH) and cortisol (pituitary-adrenal function).

Additional organ-specific irAEs include hepatitis (AST/ALT Increases, hepatomegaly, periportal edema, periportal lymphadenopathy, lymphocyte infiltrates periportal and surrounding primary biliary ducts) and pneumonitis (acute interstitial pneumonia). Less frequent irAEs include neurologic syndromes (myasthenia gravis, Guillian-Barré syndrome, aseptic meningitis), ocular AEs (uveitis), renal AEs (interstitial nephritis), cardiac AEs (myocarditis), and pancreatic AEs (lipase Increase).

Medical management of irAEs focuses on suppressing the immune response with non-steroidal and steroidal anti-inflammatory medication. Treatment algorithms for high grade IrAEs have been developed and should be followed for subjects with suspected irAEs because of ICI exposure (Naidoo et al 2015).

8.4 Follow-Up of Adverse Events

All SAEs and AESIs that are ongoing 30 days after the last dose of study treatment, and AEs messed Grade 3 or 4 that led to study treatment discontinuation that are ongoing 30 days after the date of the decision to discontinue study treatment, are to be followed until either:

- the AE has resolved
- the AE has improved to Grade 2 or lower
- The investigator determines that the event has become stable or irreversible.

This follow-up requirement also applies to related SAEs that occur >30 days after the date of the decision to discontinue study treatment.

In addition, AESIs are to be recorded in the CRF until 90 days after the decision to discontinue study treatment The status of all other AEs that are ongoing 30 days after the date of the decision to discontinue study treatment will be documented as of the Post-Treatment Follow-Up Visit.

8.5 Other Safety Considerations
8.5.1 Pregnancy

Use of medically accepted methods of contraception is very important during the study and for S months after the last dose of study treatment. If a subject becomes pregnant during the study, she will be taken off study treatment. She will be followed through the end of her pregnancy and the infant should have follow up for at least 12 months after birth. If a female partner of a male subject becomes pregnant during the study, the Sponsor will ask the pregnant female partner to be followed through the end of her pregnancy and for the infant to be followed for at least 6 months after birth.

The investigator must inform the Sponsor of the pregnancy. Forms for reporting pregnancies will be provided to the study sites upon request. The outcome of a pregnancy (for a subject or for the partner of a subject) and the medical condition of any resultant offspring must be reported to the Sponsor or designee. Any birth defect or congenital anomaly must be reported as an SAE and any other untoward events occurring during the pregnancy must be reported as AEs or SAEs, as appropriate.

8.5.2 Medication Errors/Overdose

Medication error is defined as the administration of study drug medication outside or above the established dosing regimens per the specific protocol.

Any study medication overdose, misuse, abuse, or study medication error (excluding missed doses) that results in an AE or SAE requires reporting within 24 hours to the Sponsor or designee. Forms for reporting medication errors will be provided to the study sites.

In case of overdose, the Sponsor medical monitor or designee should be contacted promptly to discuss how to proceed. Any AEs that occur as a result of an overdose have to be treated according to clinical standard practice.

Please refer to the Investigator's Brochure for additional management recommendations for an overdose of cabozantinib.

9 Statistical Considerations

Details of the planned analyses will be documented in a separate Statistical Analysis Plan (SAP). Summaries will generally be presented by cohort/dose group and overall (total subjects). No formal statistical tests are planned for this study. Confidence Intervals will be calculated for selected endpoints.

9.1 Power and Sample Size
9.1.1 Dose-Escalation Stage

The number of subjects per dose escalation cohort has been chosen based on a well-established Phase 1 dose-escalation trial design. Subjects are accrued into cohorts in a "3 plus 3" fashion with each cohort consisting initially of 3 subjects and potentially expanding to 6 subjects based upon the number of DLTs observed. A total of 9 to 36 subjects may be enrolled in this stage, depending upon the number of escalation cohorts and subjects required to establish an MTD or recommended Expansion Stage dose and schedule.

9.1.2 Expansion Stage

The objective for the Expansion Cohorts is to estimate ORR to assess if the true response rate with this combination regimen is better than that expected with monotherapy. Thus, 2-sided 80% and 60% Blyth-Still-Casella CIs will be constructed for ORR, providing 90% and 80% respectively, 1-sided confidence when interpreting the lower bound. The sample size of 30 subjects for the Expansion Cohorts was chosen to ensure the lower bound of the 2-sided 80% CI extended no more than 12 percentage points from the point estimate. Example 80% and 60%2-sided CIs, with the 1-sided interpretations of the lower bound, are shown in Table 9-1 for a range of potential values for observed ORR.

TABLE 9-1

Example Blyth-Still-Casella Confidence Intervals for N = 30 for ORR for
Expansion Cohorts with 1-Sided Interpretations of the Lower Bound

| Observed Responses (Total N = 30) | Observed ORR | 80% 2-Sided CI | | | 60% 2-Sided CI | | |
|---|---|---|---|---|---|---|---|
| | | LCL | UCL | True ORR$^a$ (90% Confidence) | LCL | UCL | True ORR$^a$ (80% Confidence) |
| 17 | 0.57 | 0.44 | 0.69 | ≥44% | 0.47 | 0.66 | ≥47% |
| 15 | 0.50 | 0.38 | 0.62 | ≥38% | 0.41 | 0.59 | ≥41% |
| 12 | 0.40 | 0.28 | 0.53 | ≥28% | 0.31 | 0.47 | ≥31% |
| 11 | 0.37 | 0.25 | 0.50 | ≥25% | 0.28 | 0.44 | ≥28% |
| 10 | 0.33 | 0.23 | 0.46 | ≥23% | 0.25 | 0.41 | ≥25% |
| 9 | 0.30 | 0.19 | 0.42 | ≥19% | 0.24 | 0.38 | ≥24% |
| 8 | 0.27 | 0.16 | 0.38 | ≥16% | 0.19 | 0.34 | ≥19% |
| 7 | 0.23 | 0.15 | 0.34 | ≥15% | 0.16 | 0.31 | ≥16% |
| 6 | 0.20 | 0.11 | 0.31 | ≥11% | 0.13 | 0.28 | ≥13% |
| 5 | 0.17 | 0.09 | 0.28 | ≥9% | 0.12 | 0.24 | ≥12% |
| 4 | 0.13 | 0.06 | 0.25 | ≥6% | 0.08 | 0.19 | ≥8% |

CI, confidence interval;
LCL lower confidence limit;
ORR objective response rate;
UCL, upper confidence limit.
$^a$Per 1-sided interpretation of the lower bound.

The planned enrollment of 30 subjects each in Expansion Cohorts 5 and 7 will be divided between 15 subjects with ICI refractory disease (PD as best response to prior ICI therapy) and 15 subjects with ICI resistant disease (CR, PR, SD as best response to prior ICI therapy). The sample size of 15 subjects was chosen to ensure the lower bound of the 2-sided 80% CI extended no more than 19 percentage points from the point estimate. Example 80% and 60%2-sided CIs, with the 1-sided interpretations of the lower bound, are shown in Table 9-2 for a range of potential values for observed ORR. Should the subjects who are ICI refractory and/or ICI resistant reach a clinically meaningful ORR a defined by the Study Oversight Committee, approximately 50 subjects may be added to Cohort 5 and/or 7 (ie, up to a total of 80 subjects per cohort) to further investigate the safety and clinical benefit of the combination in this treatment setting that has a high unmet need and a novel mechanism of action of re-sensitizing to ICI therapy. Decisions regarding the clinical meaningfulness of the achieved ORR in Expansion Cohorts 5 and 7 by the Study Oversight Committee will be based on the lower bound of 80% CI for the entire Cohort of 30 subjects or 15 subjects with ICI refractory disease and 15 subjects with ICI resistant disease, as appropriate. A target ORR of 20-25% for Expansion Cohort 5 and 15-20% for Expansion Cohort 7 may be used as guidance by the Study Oversight Committee. This generally corresponds to 80% confidence the true ORR is ≥11% for n=15 or ≥13% for n=30. The expansion of Cohort 5 and/or 7 with 50 additional subjects may be limited to either ICI refractory or ICI resistant subjects or may include subjects from both groups depending on the observed ORR.

TABLE 9-2

Example Blyth-Still-Casella Confidence Intervals for N = 15 for ORR for the
Expansion Cohorts of 15 Subjects with 1-Sided Interpretations of the Lower Bound

| Observed Responses (Total N = 15) | Observed ORR | 80% 2-Sided CI | | | 60% 2-Sided CI | | |
|---|---|---|---|---|---|---|---|
| | | LCL | UCL | True ORR$^a$ (90% Confidence) | LCL | UCL | True ORR$^a$ (80% Confidence) |
| 9 | 0.60 | 0.42 | 0.77 | ≥43% | 0.46 | 0.70 | ≥46% |
| 7 | 0.47 | 0.28 | 0.64 | ≥28% | 0.33 | 0.61 | ≥33% |
| 6 | 0.40 | 0.23 | 0.57 | ≥23% | 0.30 | 0.54 | ≥30% |
| 5 | 0.33 | 0.20 | 0.51 | ≥20% | 0.23 | 0.46 | ≥23% |
| 4 | 0.27 | 0.12 | 0.44 | ≥12% | 0.16 | 0.39 | ≥16% |
| 3 | 0.20 | 0.10 | 0.36 | ≥10% | 0.11 | 0.33 | ≥11% |
| 2 | 0.13 | 0.06 | 0.28 | ≥6% | 0.08 | 0.23 | ≥8% |
| 1 | 0.07 | 0.01 | 0.23 | ≥1% | 0.03 | 0.16 | ≥3% |

CI, confidence interval;
LCL, lower confidence limit;
ORR objective response rate;
UCL, upper confidence limit.
$^a$Per 1-sided interpretation of the lower bound.

9.2 Analysis Populations 9.2.1 Safety Population

The Safety population will consist of all subjects who received any study treatment. As enrollment is defined by receipt of study treatment, an Enrolled population is not defined to be distinct from the Safety population.

9.2.2 Dose-Escalation Population

The Dose-Escalation population will include subjects who were not replaced per Section 3.9.

9.2.3 Other Population(s)

Additional analysis populations may be defined in the SAP.

9.3 Planned Analyses 9.3.1 Safety and Tolerability Analyses

Safety will primarily be assessed by the evaluation of AEs and laboratory tests. Tolerability will be assessed by evaluation of study treatment modification and discontinuation.

9.3.1.1 Adverse Events

Adverse event terms recorded on the CRFs will be mapped to preferred terms using the Medical Dictionary for Regulatory Activities (MedDRA). The investigator will classify the severity of AEs using the CTCAE v4 and will judge each event to be "not related" or "related" to study treatment. Adverse events leading to study treatment discontinuation will also be judged by the investigator to be causally associated, or not, with the disease under study.

Summaries of AEs, irAEs, AESIs, and SAEs will be tabulated by cohort according to system organ class and preferred term by overall incidence; worst reported severity, and relationship to study treatment.

At each level of summarization, a subject will be counted only once for each AE preferred term he or she experiences within that level (ie, multiple episodes of events with the same preferred terms will be counted only once).

All reported subject deaths will be summarized by treatment group, cause of death, and relationship to study treatment.

A narrative will also be prepared to describe the accrual and expansion of Dose-Escalation Stage cohorts, subject replacement, the DLTs observed, CRC decisions and the final rationale for the recommended Expansion Stage dose.

9.3.1.2 Laboratory Test Results

Selected laboratory test results will be summarized by treatment group to evaluate worst post-baseline CTCAE grade and shifts or changes from baseline.

9.3.1.3 Study Treatment

Study treatment parameters will be presented separately for each agent, cabozantinib and atezolizumab. The number of subjects experiencing dose reduction, delay, interruption, modification and/or discontinuation due to adverse event will be provided as appropriate for each agent. Duration and intensity of study treatment will also be tabulated.

9.3.2 Analyses of Preliminary Antitumor Activity

The objective of the Expansion Stage is to estimate ORR, defined as the proportion of subjects with a confirmed CR or PR per RECIST 1.1 as determined by the investigator. Similarly, ORR will be determined per modified RECIST for immune response as determined by the investigator as an exploratory endpoint. ORR will be evaluated independently within each of the expansion cohorts and within the dose escalation cohorts.

Best overall tumor response, based upon the evaluation of target, non-target, and new lesions, will be presented as the proportion of subjects in each of the following categories: CR, PR, SD, PD, and not evaluable, and include the ORR. In the expansion cohorts, 2-sided 80% and 60% Blyth-Still-Casella CIs will be presented for ORR, providing 90% and 80% 1-sided confidence when interpreting the lower bound for the purpose of evaluating preliminary efficacy of combination therapy vs. expected efficacy with single-agent treatment from historical studies. Confidence intervals at the 95% level will also be presented for consistency with standard presentation conventions.

Median PFS and OS with associated 2-sided 95% CIs will be estimated using Kaplan-Meier methods.

Duration of response is defined as the time from first documented objective response (CR or PR) as is messed by the investigator that is subsequently confirmed until the earlier of radiographic progression or death, or censoring due to lack of these events or start of nonprotocol anticancer therapy. Medians and confidence intervals will be estimated using Kaplan-Meier analysis, limited to patients who experienced a confirmed objective response.

9.3.3 Interim Analyses

The CRC will review accumulating data from the dose escalation cohorts.

No formal interim analyses are planned for the Expansion Stage. However, safety and anti-tumor findings will be reviewed on an ongoing basis.

10 Other Analyses 16.1 Pharmacokinetic Analyses

The plasma concentration of cabozantinib will be analyzed by the Sponsor or designee using a validated bioanalytical method. Possible break-down products of cabozantinib may also be evaluated in PK blood samples collected during the study. Descriptive statistics (eg, number, mean and/or median, standard deviation, and coefficient of variation) will be used to describe the concentration-time data. Where appropriate, these data may be analyzed using population PK models and/or combined with data from other studies as part of a meta-analysis. The influence of exposure on biomarkers, clinical safety parameters (eg, selected AEs) or clinical response may also be explored. The results of the PK analysis will also be evaluated in conjunction with available safety data.

Concentrations of atezolizumab and/or break-down products of atezolizumab may also be measured in PK blood samples if considered relevant to assessment of safety and/or efficacy analyses in this study.

10.2 Biomarker Analyses

Analyses that may include but may not be limited to MET, AXL, PD-L1 and potential correlation with clinical response and other analyses (eg, sequencing, FACS) will be summarized.

The foregoing disclosure has been described in some detail by way of Illustration and example for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

Appendix A: Schedule of Assessments for the Dose Escalation Stage

The schedules of required assessments for the Dose Escalation Stage are presented in this appendix.

As described in Section 3.5.1.1, the CRC may decide to implement a Cabozantinib Run-In Dosing Schedule for some cohorts in the Dose Escalation Stage. Separate tables am provided below for the two possible dosing schedules: the Standard Dosing Schedule (Table A-1) and the Cabozantinib Run-In Dosing Schedule (Table A-2). All other assessments are to be performed according to the schedule provided irrespective of dosing schedule.

Most study assessments and procedures (including treatment administration) will be performed in cycles. Cycle 1 Day 1 (C1D1) is defined as the date of first dose of any study treatment. A cycle is generally the 21-day interval starting with the date of an atezolizumab infusion and ending with the day before the next atezolizumab infusion. However, under some circumstances no atezolizumab may be dosed during a cycle:

If the Cabozantinib Run-in Dosing Schedule is employed during the Dose Escalation Stage, the period in which cabozantinib is administered prior to the first dose of atezolizumab will be defined as Cycle 1.

If atezolizumab treatment is discontinued but cabozantinib treatment is allowed to continue with the notification of the Sponsor, each consecutive 21-day interval starting with the date of the decision to discontinue atezolizumab will be defined as a cycle. If the decision to discontinue atezolizumab occurs less than 21 days after the last infusion, then the next cycle will begin on the $22^{nd}$ day after the last infusion.

Cycles may extend beyond 21 days if atezolizumab dosing is delayed. During an atezolizumab dose delay, subjects should return to the site for scheduled safety visits every three weeks from the last dose of atezolizumab. Further, the study site should perform unscheduled visits weekly (or more frequently as clinically indicated) to monitor subject safety and appropriateness for re-treatment with study treatment. Other unscheduled visits are permitted whenever necessary. See Section 5.5 for further details.

Imaging assessments (CT, MRI, bone scan) are to be performed at protocol-defined, fixed intervals based the first dose of study treatment (defined as Week 1 Day 1 [W1D1]); all subsequent time points for these assessments will apply the same nomenclature, which will not be modified as a result of modifications or discontinuations of treatment administration.

Unless otherwise indicated, in the absence of side effects all scheduled visits will occur within windows for the protocol-specified visit schedule. If the subject experiences side effects, study treatment can be modified or delayed as described in Section 6.5. If the subject is unable to have a study assessment taken within the defined time window due to an event outside of his or her control (eg, clinic closure, personal emergency, inclement weather, vacation), the assessment should be performed as close as possible to the required schedule. Laboratory panels for serum chemistry, hematology, and urinalysis are defined in Section 5.6.5.

TABLE A-1

Schedule of Assessments for the Dose Escalation Stage: Standard Dosing Schedule

| Assessment: | Pre-enrollment Screening[a] (Before First Dose) | Cycle 1 (±3 days) Day 1 | Cycle 1 Day 10 | Cycle 1 Day 21 | Cycle 2 (±3 days) Day 1 | Cycle 2 Day 10 | Cycle 2 Day 21 | Post-enrollment Cycles 3-8 (±3 days) | Post-enrollment Cycles 9 and above (±5 days) | 30-Day Post-Treatment Follow-Up (+14 days) | Extended Follow Up |
|---|---|---|---|---|---|---|---|---|---|---|---|
| Informed consent (Section 5.1) | X[b] | | | | | | | | | | |
| Demographics, medical and cancer history (Section 5.6.1) | ≤28 days | | | | | | | | | | |
| Physical examination[c] + weight (Section 5.6.2) | <28 days | X predose | | X | X[d] | | X[d] | Day 1 of every cycle or every three weeks after the last dose of atezolizumab (if infusions are delayed). | Day 1 of every cycle or every three weeks after the last dose of atezolizumab (if infusions are delayed). | X | |
| ECOG PS (Section 5.6.2, Appendix E) | ≤28 days (+Karnofsky PS for RCC subjects) | X | | X | X[d] | | X[d] | Day 1 of every cycle or every three weeks after the last dose of atezolizumab (if infusions are delayed). | Day 1 of every cycle or every three weeks after the last dose of atezolizumab (if infusions are delayed). | X | |
| Vital signs (Section 5.6.3) | ≤28 days | X[e] | | X | X[e] | | X[e] | Day 1 of every cycle or every three weeks after the last dose of atezolizumab (if infusions are delayed).[e] | Day 1 of every cycle or every three weeks after the last dose of atezolizumab (if infusions are delayed).[e] | X | |
| 12-lead ECG (Section 5.6.4)[f] | ≤14 days | X[g] predose | | X | [d] x | | | Day 1 of every 4th cycle starting with C3D1 (ie, C3D1, C7D1, etc) or every 12 weeks after the last dose of atezolizumab (if infusions are delayed) | | X | |
| Hematology and chemistry by central lab (Section 5.6.5) | 14 days | X[h,i] predose | X | X | X[h,i] predose | | | Day 1 of every cycle or every three weeks after the last dose of atezolizumab (if infusions are delayed).[h,i] | Day 1 of every cycle or every three weeks after the last dose of atezolizumab (if infusions are delayed).[h,i] | X | |
| Hepatitis screening by central lab (Section 5.6.5) | X | | | | | | | | | | |
| PT/INR and PTT by central lab (Section 5.6.5) | <14 days | X[g] predose | | X | X[d] | | | Day 1 of every 3rd cycle starting with C3D1 (ie, C3D1, C6D1, etc) or every nine weeks after the last dose of atezolizumab (if infusions are delayed) | Day 1 of every 3rd cycle starting with C3D1 (ie, C3D1, C6D1, etc) or every nine weeks after the last dose of atezolizumab (if infusions are delayed) | X | |
| Urinalysis by local lab (Section 5.6.5) | 14 days | X[g,h] predose | | X | X[h] predose | | | Day 1 of every cycle or every three weeks after the last dose of atezolizumab (if infusions are delayed) | Day 1 of every cycle or every three weeks after the last dose of atezolizumab (if infusions are delayed) | X | |
| Urine chemistry incl. UPCR by central lab (Section 5.6.5) | 14 days | X[g] predose | | X | X[d] | | | Day 1 of every other cycle starting with C3D1 (ie, C3D1, C5D1, etc) or every six weeks after the last dose of atezolizumab (if infusions are delayed) | Day 1 of every other cycle starting with C3D1 (ie, C3D1, C5D1, etc) or every six weeks after the last dose of atezolizumab (if infusions are delayed) | X | |
| Pregnancy test by local lab | ≤7 days serum | X[g] predose (serum) | | | (serum or urine) | | | Day 1 of every cycle or every three weeks after the last dose of atezolizumab (if infusions are delayed). (serum or urine) | Day 1 of every cycle or every three weeks after the last dose of atezolizumab (if infusions are delayed). (serum or urine) | X | |
| Thyroid function test by central lab (Section 5.6.5) | 14 days | X[g] predose | | X | X[d] | | | Day 1 of every 3rd cycle starting with C3D1 (ie, C3D1, C6D1, etc) or every nine weeks after the last dose of atezolizumab (if infusions are delayed) | Day 1 of every 3rd cycle starting with C3D1 (ie, C3D1, C6D1, etc) or every nine weeks after the last dose of atezolizumab (if infusions are delayed) | X | |

TABLE A-1-continued

Schedule of Assessments for the Dose Escalation Stage: Standard Dosing Schedule

| Assessment: | Pre-enrollment Screening[a] (Before First Dose) | Cycle 1 (±3 days) | | | Cycle 2 (±3 days) | | | Post-enrollment Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|---|
| | | Day 1 | Day 10 | Day 21 | Day 1 | Day 10 | Day 21 | | | | |
| Archival tumor tissue sample[k] (Section 5.6.7) | X | | | | | | | | | | |
| Tumor assessment: CT/MRI Chest, Abdomen, Pelvis (Section 5.6.8) | ≤28 days | CT of the chest, abdomen, and pelvis or CT of the chest with MRI of the abdomen and pelvis will be performed in all subjects at screening and every 6 weeks (±5 days) after first dose (at W7D1, W13D1 etc). Upon completion of 12 months on study, these assessments will be performed every 12 weeks (±7 days). To ensure image consistency, the same imaging modalities and acquisition protocols used at screening are to be used for subsequent tumor assessments. CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy. PR or CR per RECIST 1.1 at a given time point must be confirmed by repeat assessments >4 weeks after the criteria for response are first met. Subjects with PD per RECIST 1.1 who continue with study treatment are to have tumor measurement outcomes confirmed >4 weeks after the initial PD criteria were met. For subjects who continue treatment after the confirmatory tumor scans, regularly scheduled imaging will continue. ||||||||||
| Tumor assessment: MRI/CT Brain (Section 5.6.8) | <28 days | MRI (or CT) of the brain will be performed at screening in all subjects with RCC, and for subjects with UC who have a history or clinical symptoms of brain metastasis. After first dose, MRI (or CT) scans of the brain are only required in subjects with documented, treated brain metastasis. Assessments will be performed every 12 weeks 7 days) after first dose (at W13D1, W26D1 etc). The schedule for these assessments is independent of the atezolizumab dosing schedule. To ensure image consistency, the same imaging modalities and acquisition protocols used at screening are to be used for subsequent tumor assessments. (Note: in order to meet the eligibility requirements of the study, brain metastasis must have been treated and stable for at least 4 weeks before first dose of study treatment. Subjects without documented brain metastasis during the screening assessment are not required to undergo brain imaging after starting treatment unless clinically indicated). CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy ||||||||||
| Bone scans (Section 5.6.8) | <28 days | Technetium bone scans (TBS) will be performed at screening on subjects who have a history or clinical symptoms (ie, bone pain) of bone metastases. After study treatment initiation bone scans are only required in subjects with documented bone lesions or if clinically indicated by signs and symptoms suggestive of new bone metastases. Assessments after the first dose will follow routine clinical practice (approximately every 12 weeks throughout the first 12 months and every 24 weeks thereafter). The schedule for these assessments is independent of the atezolizumab dosing schedule. Bone scans are to be used for direct corroborative imaging with CT/MRI if necessary (these CT/MRI findings will be used for RECIST v1.1 evaluation), and bone scan findings alone should not be used for the determination of progression in this study. Bone scan evaluations will end on the date of last CT/MRI scan. If the bone scan schedule doesn't coincide with the last CT/MRI scan, no additional bone scan is needed after the last CT/MRI has been performed. ||||||||||
| PK blood samples[l] (Section 5.6.6.1) | | C1D1 (before treatment, approximately 5 min after atezolizumab infusion & 2 h, 4 h, and 6-8 h after cabozantinib dose) and predose on C1D10, C2D1, and C3D1. ||||||||||

TABLE A-1-continued

Schedule of Assessments for the Dose Escalation Stage: Standard Dosing Schedule

| Assessment: | Pre-enrollment Screening[a] (Before First Dose) | Cycle 1 (±3 days) | | | Cycle 2 (±3 days) | | | Post-enrollment Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|---|
| | | Day 1 | Day 10 | Day 21 | Day 1 | Day 10 | Day 21 | | | | |
| Blood sample-Pharmacogenetic (Section 5.6.7) | predose | X | | | | | | | | | |
| Blood sample-immune cell profiling by FACS (Section 5.6.7) | | Predose on C1D1, C1D10, and C2D1 (may be performed at selected sites) | | | | | | | | | |
| Blood sample-serum/plasma biomarkers | | | | | | | | Predose on C1D1, C1D10, C2D1, and C3D1. An optional sample may be collected at the first sign of progression per the investigator. | | | |
| Blood sample-cell and/or plasma pharmacogenomics (Section 5.6.7) | | | | | | | | Predose on C1D1, C1D10, C2D1, and C3D1. An optional sample may be collected at the first sign of progression per the investigator. | | | |
| Concomitant medication (Section 7) | | Document concomitant medication taken from 28 days before first dose of study treatment through 30 days after the date of the decision to discontinue study treatment | | | | | | | | | |
| Adverse events (Sections 8.1, 8.2, and 8.3.1) | | Document new or worsening AEs from informed consent through 30 days (90 days for AESIs) after the date of the decision to permanently discontinue study treatment. AE information will be collected at study visits and may also be collected at any time over the phone or by spontaneous subject report. At the date of the first dose of study treatment, AEs will be documented pre- and post-dose. Certain AEs and all SAEs that are ongoing 30 days after of the date of the decision to permanently discontinue study treatment are to be followed until resolution or determination by the investigator that the event is stable or irreversible (see Section 8.4). | | | | | | | | | |
| Atezolizumab dosing[f] (Section 6.2) | | X | | | X | | | Atezolizumab will be administered as an IV infusion at the clinic every 3 weeks (−2 days) on Day 1 of each cycle until study treatment is discontinued | | | |
| Cabozantinib dosing (Section 6.2) | | Cabozantinib will administered in clinic C1D1 and then will be taken once daily at home until study treatment is discontinued | | | | | | | | | |
| Cabozantinib daily dosing diary (Section 5.6.8.3) | | The amount of cabozantinib treatment taken is to be recorded daily from C1D1 to C1D21. | | | | | | | | | |

TABLE A-1-continued

Schedule of Assessments for the Dose Escalation Stage: Standard Dosing Schedule

| Assessment: | Pre-enrollment Screening[a] | Cycle 1 (±3 days) | | | Cycle 2 (±3 days) | | Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|
| | (Before First Dose) | Day 1 | Day 10 | Day 21 | Day 1 | Day 10 Day 21 | | | | |
| Dispense/return of cabozantinib and compliance accounting (Section 6.3) | | Cabozantinib is to be dispensed to subjects every 3 weeks. | | | | | | | | |
| Additional anticancer treatment and survival status (Sections 5.3 and 5.6.10) | | | | | | | '7 days) after 30-day | | | Every 12 weeks post-treatment follow-up visit until death |

[a] Results of screening assessments must be reviewed before first dose of study treatment to confirm that the subject meets the eligibility criteria.
[b] Informed consent may be obtained greater than 28 days prior to first dose of study treatment, but must be provided before any study-specific procedures are performed; however, evaluations performed as part of routine care prior to informed consent can be utilized as screening evaluations if permitted by the site's IRB/EC policies.
[c] Symptom-directed physical examination will be conducted on C1D1 before first dose of study treatment and at subsequent safety assessment visits.
[d] Assessments scheduled for C2D1 do not need to be performed if the same assessment was performed within 3 days at the end of Cycle 1.
[e] Vital signs should be assessed within 60 min prior to initiation of atezolizumab infusions, and further vital sign assessment should be performed during and after the infusion as clinically indicated.
[f] Additional ECGs are to be performed if clinically indicated.
[g] This assessment is intended to confirm suitability for treatment after screening and prior to first dose on C1D1. If this assessment has been performed during screening within 14 days (7 days for pregnancy test) prior to C1D1, this assessment does not need to be performed on C1D1 unless the subject's clinical status has changed (eg, onset of new symptoms indicative of clinical deterioration). If the assessment is performed on C1D1, the results must be available to and reviewed by the investigator prior to any treatment being administered.
[h] Serum chemistry, hematology, and urinalysis laboratory samples must be collected and the results must be reviewed within 72 h before any atezolizumab infusion administered on study.
[i] Local laboratory assessments for these panels may be obtained and used if the results are required by the investigator in a rapid timeframe. See Section 5.6.5 and the Laboratory Manual for more detailed information on laboratory assessments.
[j] Hepatitis B surface antigen and Hepatitis C antibody (with reflex testing HCV RNA if antibody test is positive) to be assessed at screening.
[k] Tumor tissue (archival) will be obtained prior to first dose whenever available. Formalin-fixed paraffin embedded (FFPE) tumor blocks are preferred but in cases where this is not possible, 12 unstained freshly cut FFPE slides should be obtained. See Translational Medicine Laboratory Manual for specific instructions.
[l] After C1D1, PK samples should be collected approximately 8 or more hours after the previous dose of cabozantinib, and if cabozantinib will be administered on that day, PK samples should be collected prior to cabozantinib administration. The investigator will ask the subject for the date and time of the most recent prior dose of cabozantinib, and this information will be recorded on the appropriate CRF page.
[m] Atezolizumab doses are not to be administered less than 19 days apart.

TABLE A-2

Schedule of Assessments for the Dose Escalation Stage: Cabozantinib Run-In Dosing Schedule

| Assessment: | Pre-enrollment Screening[a] (Before First Dose) | Cycle 1 (±3 days) Day 1 | Day 10 | Day 21 | Cycle 2 (±3 days) Day 1 | Da) 10 | Day 21 | Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|---|
| Informed consent (Section 5.1) | X[b] | | | | | | | | | | |
| Demographics, medical and cancer history (Section 5.6.1) | 28 days | | | | | | | | | | |
| Physical examination[e] + weight (Section 5.6.2) | 28 days | X predose | | | X | | X | Day 1 of every cycle[d] or every three weeks after the last dose of atezolizumab (if infusions are delayed). | Day 1 of every cycle[d] or every three weeks after the last dose of atezolizumab (if infusions are delayed). | X | |
| ECOG PS (Section 5.6.2, Appendix E) | 28 days (+Karnofsky N for RCC subjects) | X | | | X | | X | Day 1 of every cycle[d] or every three weeks after the last dose of atezolizumab (if infusions are delayed). | Day 1 of every cycle[d] or every three weeks after the last dose of atezolizumab (if infusions are delayed). | X | |
| Vital signs (Section 5.6.3) | 28 days | X[e] | | | X[e] | | X | Day 1 of every cycle or every three weeks after the last dose of atezolizumab (if infusions are delayed)[e] | Day 1 of every cycle or every three weeks after the last dose of atezolizumab (if infusions are delayed)[e] | X | |
| 12-lead ECG (Section 5.6.4)[f] | 14 | X[g] | | | X | | X | Day 1 of every 4th cycle starting with C4D1 (ie, C4D1, C8D1, etc) or every 12 weeks after the last dose of atezolizumab (if infusions are delayed) | Day 1 of every 4th cycle starting with C4D1 (ie, C4D1, C8D1, etc) or every 12 weeks after the last dose of atezolizumab (if infusions are delayed) | X | |
| Hematology and chemistry by central lab (Section 5.6.5) | <14 days | X[h] predose | | | X[h,i] predose | | X | Day 1 of every cycle or every three weeks after the last dose of atezolizumab (if infusions are delayed)[h,i] | Day 1 of every cycle or every three weeks after the last dose of atezolizumab (if infusions are delayed)[h,i] | X | |
| Hepatitis screening) by central lab (Section 5.6.5) | X | | | | | | | | | | |
| PT/INR and PTT by central lab (Section 5.6.5) | 14 days | X[g] predose | | | X | | X | Day 1 of every cycle or every nine weeks after the last dose of atezolizumab (if infusions are delayed) | Day 1 of every cycle or every nine weeks after the last dose of atezolizumab (if infusions are delayed) | X | |
| Urinalysis by local lab (Section 5.6.5) | 14 days | X[i] predose | | | X[i] predose | | X | Day 1 of every cycle or every three weeks after the last dose of atezolizumab (if infusions are delayed)[j] | Day 1 of every cycle or every three weeks after the last dose of atezolizumab (if infusions are delayed)[j] | X | |
| Urine chemistry incl. UPCR by central lab (Section 5.6.5) | 14 days | X[g] predose | | | X | | X | Day 1 of every other cycle starting with C4D1 (ie, C4D1, C6D1, etc) or every six weeks after the last dose of atezolizumab (if infusions are delayed) | Day 1 of every other cycle starting with C4D1 (ie, C4D1, C6D1, etc) or every six weeks after the last dose of atezolizumab (if infusions are delayed) | X | |
| Pregnancy test by local lab | <7 days serum | X[g] predose (serum) | | | serum (or urine) | | | Day 1 of every cycle or every three weeks after the last dose of atezolizumab (if infusions are delayed). (serum or urine) | Day 1 of every cycle or every three weeks after the last dose of atezolizumab (if infusions are delayed). (serum or urine) | X | |
| Thyroid function test by central lab (Section 5.6.5) | 14 days | X[g] predose | | | X | | X | Day 1 of every 3rd cycle starting with C4D1 (ie, C4D1, C7D1, etc) or every nine weeks after the last dose of atezolizumab (if infusions are delayed) | Day 1 of every 3rd cycle starting with C4D1 (ie, C4D1, C7D1, etc) or every nine weeks after the last dose of atezolizumab (if infusions are delayed) | X | |

TABLE A-2-continued

Schedule of Assessments for the Dose Escalation Stage: Cabozantinib Run-In Dosing Schedule

| Assessment: | Pre-enrollment Screening[a] | Post-enrollment | | | | | | 30-Day Post-Treatment Follow-Up | Extended Follow Up |
|---|---|---|---|---|---|---|---|---|---|
| | | Cycle 1 (±3 days) | | Cycle 2 (±3 days) | | | Cycles 3-8 (±3 days) | Cycles 9 and above (±5 days) | (+14 days) |
| | (Before First Dose) | Day 1 | Day 10 | Day 21 | Day 1 | Day 10 | Day 21 | | | |
| Archival tumor tissue sample[k] (Section 5.6.7) | X | | | | | | | | | |
| Tumor assessment: CT/MRI Chest, Abdomen, Pelvis (Section 5.6.8) | 28 days | CT of the chest, abdomen, and pelvis or CT of the chest with MRI of the abdomen and pelvis will be performed in all subjects at screening and every 6 weeks (±5 days) after first dose (at W7D1, W13D1 etc). Upon completion of 12 months on study, these assessments will be performed every 12 weeks (±7 days). To ensure image consistency, the same imaging modalities and acquisition protocols used at screening are to be used for subsequent tumor assessments. CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy. PR or CR per RECIST 1.1 at a given time point must be confirmed by repeat assessments >4 weeks after the criteria for response are first met. Subjects with PD per RECIST 1.1 who continue with study treatment are to have tumor measurement outcomes confirmed >4 weeks after the initial PD criteria were met. For subjects who continue treatment after the confirmatory tumor scans, regularly scheduled imaging will continue. | | | | | | | | |
| Tumor assessment: MRI/CT Brain (Section 5.6.8) | 28 days | MRI (or CT) of the brain will be performed at screening in all subjects with RCC, and for subjects with UC who have a history or clinical symptoms of brain metastasis. After first dose, MRI (or CT) scans of the brain are only required in subjects with documented, treated brain metastasis. Assessments will be performed every 12 weeks (±7 days) after first dose (at W13D1, W26D1 etc). The schedule for these assessments is independent of the atezolizumab dosing schedule. To ensure image consistency, the same imaging modalities and acquisition protocols used at screening are to be used for subsequent tumor assessments. (Note: in order to meet the eligibility requirements of the study, brain metastasis must have been treated and stable for at least 4 weeks before first dose of study treatment. Subjects without documented brain metastasis during the screening assessment are not required to undergo brain imaging after starting treatment unless clinically indicated). CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy | | | | | | | | |
| Bone scans (Section 5.6.8) | <28 days | Technetium bone scans (TBS) will be performed at screening on subjects who have a history or clinical symptoms (ie, bone pain) of bone metastases. After study treatment initiation bone scans are only required in subjects with documented bone lesions or if clinically indicated by signs and symptoms suggestive of new bone metastases. Assessments after the first dose will follow routine clinical practice (approximately every 12 weeks throughout the first 12 months and every 24 weeks thereafter). The schedule for these assessments is independent of the atezolizumab dosing schedule. Bone scans are to be used for corroborative imaging with CT/MRI if necessary (these CT/MRI findings will be used for RECIST v1.1 evaluation), and bone scan findings alone should not be used for the determination of progression in this study. Bone scan evaluations will end on the date of last CT/MRI scan. If the bone scan schedule doesn't coincide with the last CT/MRI scan, no additional bone scan is needed after the last CT/MRI scan has been performed. | | | | | | | | |
| PK blood samples[l] | | C1D1 (before treatment, & 2 h, 4 h, and 6-8 h after cabozantinib dose) and predose on C2D1, C2D10, and C3D1. | | | | | | | | |

TABLE A-2-continued

Schedule of Assessments for the Dose Escalation Stage: Cabozantinib Run-In Dosing Schedule

| Assessment: | Pre-enrollment Screening[a] (Before First Dose) | Cycle 1 (±3 days) | | | Cycle 2 (±3 days) | | | Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|---|
| | | Day 1 | Day 10 | Day 21 | Day 1 | Day 10 | Day 21 | | | | |
| (Section 5.6.6.1) Blood sample-Pharmacogenetic (Section 5.6.7) | | X predose | | | | | | | | | |
| Blood sample-immune cell profiling by FACS (Section 5.6.7) | | Predose on C1D1, C2D1, and C2D10 (may be performed at selected sites) | | | | | | | | | |
| Blood sample-serum/plasma biomarkers (Section 5.6.7) | | | | | Predose on C1D1, C2D1, C2D10, and C3D1 An optional sample may be collected at the first sign of progression per the investigator. | | | | | | |
| Blood sample-cell and/or plasma pharmacogenomics (Section 5.6.7) | | | | | Predose on C1D1, C2D1, C2D10, and C3D1 An optional sample may be collected at the first sign of progression per the investigator. | | | | | | |
| Concomitant medication (Section 7) | Document concomitant medication taken from 28 days before first dose of study treatment through 30 days after the date of the decision to discontinue study treatment | | | | | | | | | | |
| Adverse events (Sections 8.1, 8.2, and 8.3.1) | Document new or worsening AEs from informed consent through 30 days (90 days for AESIs) after the date of the decision to permanently discontinue study treatment. AE information will be collected at study visits and may also be collected at any time over the phone or by spontaneous subject report. At the date of the first dose of study treatment, AEs will be documented pre- and post-dose. Certain AEs and all SAEs that are ongoing 30 days after of the date of the decision to permanently discontinue study treatment are to be followed until resolution or determination by the investigator that the event is stable or irreversible (see Section 8.4). | | | | | | | | | | |
| (Section 6.2) | | Atezolizumab dosing[m] | | | Atezolizumab | X | | will be administered as an IV infusion at the clinic every 3 weeks (−2 days) on Day 1 of each cycle until study treatment is discontinued | | | |
| Cabozantinib dosing (Section 6.2) | | Cabozantinib will administered in clinic C1 D1 and then will be taken once daily at home until study treatment is discontinued | | | | | | | | | |
| Cabozantinib daily dosing diary (Section 5.6.8.3) | | | | | The amount of cabozantinib treatment taken is to be recorded daily from C2D1 to C2D21. | | | | | | |

TABLE A-2-continued

Schedule of Assessments for the Dose Escalation Stage: Cabozantinib Run-In Dosing Schedule

| Assessment: | Pre-enrollment Screening[a] | Cycle 1 (±3 days) | | | Cycle 2 (±3 days) | | | Cycles 3-8 (±3 days) | Cycles 9 and above (±5 days) | 30-Day Post-Treatment Follow-Up (+14 days) | Extended Follow Up |
|---|---|---|---|---|---|---|---|---|---|---|---|
| | (Before First Dose) | Day 1 | Day 10 | Day 21 | Day 1 | Day 10 | Day 21 | | | | |
| Dispense/return of cabozantinib and compliance accounting (Section 6.3) | | Cabozantinib is to be dispensed to subjects every 3 weeks. | | | | | | | | | |
| Additional anticancer treatment and survival status (Sections 5.3 and 5.6.10) | | | | | | | | | | (+7 days) after 30-day | Every 12 weeks post-treatment follow-up visit until death |

[a]Results of screening assessments must be reviewed before first dose of study treatment to confirm that the subject meets the eligibility criteria.
[b]Informed consent may be obtained greater than 28 days prior to first dose of study treatment, but must be provided before any study-specific procedures are performed; however, evaluations performed as part of routine care prior to informed consent can be utilized as screening evaluations if permitted by the site's IRB/EC policies.
Symptom-directed physical examination will be conducted on C1D1 before first dose of study treatment and at subsequent safety assessment visits. Assessments scheduled for C3D1 do not need to be performed if the same assessment was performed within 3 days at the end of Cycle 2.
[c]Vital signs should be assessed within 60 min prior to initiation of atezolizumab infusions, and further vital sign assessment should be performed during and after the infusion as clinically indicated.
[f]Additional ECGs are to be performed if clinically indicated.
[g]This assessment is intended to confirm suitability for treatment after screening and prior to first dose on C1D1. If this assessment has been performed during screening within 14 days (7 days for pregnancy test) prior to C1D1, this assessment does not need to be performed on C1D1 unless the subject's clinical status has changed (eg, onset of new symptoms indicative of clinical deterioration). If the assessment is performed on C1D1, the results must be available to and reviewed by the investigator prior to any treatment being administered.
[h]Local laboratory assessments for these panels may be obtained and used if the results are required by the investigator in a rapid timeframe. See Section 5.6.5 and the Laboratory Manual for more detailed information on laboratory assessments.
Serum chemistry, hematology, and urinalysis laboratory samples must be collected and the results must be reviewed within 72 h before any atezolizumab infusion administered on study.
Hepatitis B surface antigen and Hepatitis C antibody (with reflex testing HCV RNA if antibody test is positive) to be assessed at screening.
[k]Tumor tissue (archival) will be obtained prior to first dose whenever available. Formalin-fixed paraffin embedded (FFPE) tumor blocks are preferred but in cases where this is not possible, 12 unstained freshly cut FFPE slides should be obtained. See Translational Medicine Laboratory Manual for specific instructions.
[l]After C1 D1, PK samples should be collected approximately 8 or more hours after the previous dose of cabozantinib, and if cabozantinib will be administered on that day, PK samples should be collected prior to cabozantinib administration. The investigator will ask the subject for the date and time of the most recent prior dose of cabozantinib, and this information will be recorded on the appropriate CRF page.
[m]Atezolizumab doses are not to be administered less than 19 days apart.

Appendix B: Schedule of Assessments for the Expansion Stage

The schedule of required assessments for the Expansion Stage is presented in this appendix in the table below. As the PK and biomarker sample collection time points differ slightly for the Standard Dosing Schedule and Cabozantinib Run-In Dosing Schedule, duplicate rows for these assessments are presented in the table; the Cabozantinib Run-In Dosing Schedule rows are presented in gray for clarity.

Most study assessments and procedures (including treatment administration) will be performed in cycles. Cycle 1 Day 1 (C1D1) is defined as the date of first dose of any study treatment. Cycles may extend beyond 21 days if atezolizumab dosing is delayed. A cycle is generally the 21-day interval starting with the date of an atezolizumab Infusion and ending with the day before the next atezolizumab Infusion. However, if atezolizumab treatment is discontinued but cabozantinib treatment is allowed to continue with the notification of the Sponsor, each consecutive 21-day interval starting with the date of the decision to discontinue atezolizumab will be defined as a cycle. If the decision to discontinue atezolizumab occurs less than 21 days after the last infusion, then the next cycle will begin on the 22? day after the last infusion.

During an atezolizumab dose delay, subjects should return to the site for scheduled safety visits every three weeks from the last dose of atezolizumab. Further, the study site should perform unscheduled visits weekly (or more frequently as clinically indicated) to monitor subject safety and appropriateness for re-treatment with study treatment. Other unscheduled visits are permitted whenever necessary. See Section 5.5 for further details.

Imaging assessments (CT, MRI, bone scan) are to be performed at protocol-defined, fixed intervals based the first dose of study treatment (defined as Week 1 Day 1 [W1D1]); all subsequent time points for these assessments will apply the same nomenclature, which will not be modified as a result of modifications or discontinuations of treatment administration.

Unless otherwise indicated, in the absence of side effects all scheduled visits will occur within windows for the protocol-specified visit schedule. If the subject experiences side effects, study treatment can be modified or delayed as described in Section 6.5. If the subject is unable to have a study assessment taken within the defined time window due to an event outside of his or her control (eg, clinic closure, personal emergency, inclement weather, vacation), the assessment should be performed as close as possible to the required schedule. Laboratory panels for serum chemistry, hematology, and urinalysis are defined in Section 5.6.5.

APPENDIX B

Schedule of Assessments for the Expansion Stage

| Assessment: | Pre-enrollment Screening[a] (Before First Dose) | Cycle 1 (±3 days) | Post-enrollment Cycles 2 through 8 (±3 days) | Cycles 9 and Above (15 days) | 30-Day Post-Treatment Follow-Up (+14 days) | Extended Follow Up |
|---|---|---|---|---|---|---|
| Informed consent (Section 5.1) | x[b] | | | | | |
| Demographics, medical and cancer history (Section 5.6.1) | <28 days | | | | | |
| Physical examination[c] + weight (Section 5.6.2) | 28 days (with height) | C1D1 (predose) | Day 1 of every cycle or every three weeks after the last dose of atezolizumab (if infusions are delayed) | Day 1 of every cycle or every three weeks after the last dose of atezolizumab (if infusions are delayed) | X | |
| ECOG Performance status (Section 5.6.2, Appendix E) | 28 days (+Karnofsky for RCC subjects) | C1D1 | Day 1 of every cycle or every three weeks after the last dose of atezolizumab (if infusions are delayed) | Day 1 of every cycle or every three weeks after the last dose of atezolizumab (if infusions are delayed) | X | |
| Vital signs (Section 5.6.3) | <28 days | C1D1[d] | | Day 1 of every cycle or every three weeks after the last dose of atezolizumab (if infusions are delayed)[d] | X | |
| 12-lead ECG (Section 5.6A)[e] | <14 days | C1D1[f] predose | | Day 1 of every 4th cycle starting with C3D1 (ie, C3D1, C7D1, etc) or every 12 weeks after the last dose of atezolizumab (if infusions are delayed) | X | |
| Hematology and Chemistry by central lab (Section 5.6.5) | <14 days | C1D1[g,h] predose | | Day 1 of every cycle or every three weeks after the last dose of atezolizumab (if infusions are delayed)[g,h] | X | |
| For CRPC only: testosterone (Section 5.6.5) and PSA (Section 5.6.8.3) | 28 days (PSA and testosterone) | | | PSA only: Day 1 of every 3rd cycle for first 6 months and Day 1 of every 5th cycle thereafter | | |
| Hepatitis screening[f] by central lab (Section 5.6.5) | X | | | | | |
| PT/INR and PTT by central lab (Section 5.6.5) | <14 days | C1D1[f] predose | | Day 1 of every 3rd cycle starting with C3D1 (ie, C3D1, C6D1, etc) or every nine weeks after the last dose of atezolizumab (if infusions are delayed) | X | |
| Urinalysis by local lab (Section 5.6.5) | 14 days | C1D1[g] predose | | Day 1 of every cycle or every three weeks after the last dose of atezolizumab (if infusions are delayed)[g] | X | |
| Urine chemistry incl. UPCR by central lab (Section 5.6.5) | 14 days | C1D1[f] predose | | Day 1 of every other cycle starting with C3D1 (ie, C3D1, C5D1, etc) or every six weeks after the last dose of atezolizumab (if infusions are delayed) | X | |
| Pregnancy test by local lab (Section 5.6.5) | <7 days (serum) | C1 D1[f] predose (serum) | | Day 1 of every cycle or every three weeks after the last dose of atezolizumab (if infusions are delayed) (urine) | | |

APPENDIX B-continued

Schedule of Assessments for the Expansion Stage

| Assessment: | Pre-enrollment Screening[a] (Before First Dose) | Cycle 1 (±3 days) | Cycles 2 through 8 (±3 days) | Cycles 9 and Above (±5 days) | 30-Day Post-Treatment Follow-Up (+14 days) | Extended Follow Up |
|---|---|---|---|---|---|---|
| | | | Post-enrollment | | | |
| Thyroid function test by central lab (Section 5.6.5) | 14 days | C1D1[f] predose | Day 1 of every 3rd cycle starting with C3D1 (ie, C3D1, C6D1, etc) or every nine weeks after the last dose of atezolizumab (if infusions are delayed) | | X | |
| Archival tumor tissue sample[j] | X | | | | | |
| Optional tumor biopsy (Section 5.6.7) | After the first dose of study treatment (6 weeks or later) if archival tissue is evaluable. If archival samples are not evaluable, then tissue may be collected before the first dose of study treatment. | | | | | |
| Tumor assessment: CT/MRI Chest, Abdomen, Pelvis (Section 5.6.8) | 28 days | | CT of the chest, abdomen, and pelvis or CT of the chest with MRI of the abdomen and pelvis will be performed in all subjects at screening and every 6 weeks (±5 days) after first dose (at W7D1, W13D1 etc). Upon completion of 12 months on study, these assessments will be performed every 12 weeks (±7 days). To ensure image consistency, the same imaging modalities and acquisition protocols used at screening are to be used for subsequent tumor assessments. CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy. PR or CR per RECIST 1.1 at a given time point must be confirmed by repeat assessments >4 weeks after the criteria for response are first met. Subjects with PD per RECIST 1.1 who continue with study treatment are to have tumor measurement outcomes confirmed >4 weeks after the initial PD criteria were met. For subjects who continue treatment after the confirmatory tumor scans, regularly scheduled imaging will continue. | | | |
| Tumor assessment: MRI/CT Brain (Section 5.6.8) | 28 days | | MRI (or CT) of the brain will be performed at screening in all subjects with RCC and NSCLC, and for subjects with UC and CRPC who have a history or clinical symptoms of brain metastasis. After first dose, MRI (or CT) scans of the brain are only required in subjects with documented, treated brain metastasis. Assessments should be performed every 12 weeks (±7 days) after first dose (at W13D1, W26D1 etc). The schedule for these assessments is independent of the atezolizumab dosing schedule. To ensure image consistency, the same imaging modalities and acquisition protocols used at screening are to be used for subsequent tumor assessments. (Note: in order to meet the eligibility requirements of the study, brain metastasis must have been treated and stable for at least 4 weeks before first dose of study treatment. Subjects without documented brain metastasis during the screening assessment are not required to undergo brain imaging after starting treatment unless clinically indicated). CT/MRIs are to be performed per the protocol-defined schedule regardless of whether study treatment is reduced, interrupted, delayed, or discontinued, and the tumor assessment schedule is independent of the atezolizumab dosing schedule. Tumor imaging will continue until radiographic disease progression per RECIST 1.1 as determined by the investigator. For subjects who discontinue study treatment before radiographic disease progression per RECIST 1.1, regularly scheduled imaging assessments should continue if possible until radiographic progression per RECIST 1.1 or initiation of subsequent anticancer therapy | | | |
| Bone scans (Section 5.6.8) | 28 days | | Technetium bone scans (TBS) will be performed at screening in all subjects with CRPC and for subjects with RCC, UC, or NSCLC who have a history or clinical symptoms (ie, bone pain) of bone metastases. After study treatment initiation bone scans are only required in subjects with documented bone lesions or if clinically indicated by signs and symptoms suggestive of new bone metastases. Assessments after the first dose will follow routine clinical practice (approximately every 12 weeks throughout the first 12 months and every 24 weeks thereafter). Bone scans are to be used to direct corroborative imaging with CT/MRI if necessary (these CT/MRI findings will be used for RECIST v1.1 evaluation), and bone scan findings alone should not be used for the determination of progression in this study. Bone scan evaluations will end on the date of last CT/MRI scan. If the bone scan schedule doesn't coincide with the last CT/MRI scan, no additional bone scan is needed after the last CT/MRI has been performed. | | | |

APPENDIX B-continued

Schedule of Assessments for the Expansion Stage

| Assessment: | Pre-enrollment Screening[a] (Before First Dose) | Post-enrollment | | | |
|---|---|---|---|---|---|
| | | Cycle 1 (±3 days) | Cycles 2 through 8 (±3 days) | Cycles 9 and Above (15 days) | 30-Day Post-Treatment Follow-Up (+14 days) | Extended Follow Up |

*Pharmacokinetic and Biomarker Blood Sample Assessment for the Standard Dosing Schedule*

| Assessment: | Pre-enrollment | Cycle 1 | Cycles 2 through 8 | Cycles 9 and Above | | |
|---|---|---|---|---|---|---|
| PK blood samples[k] (Section 5.6.6.1) | predose | X | | C1D1 (before treatment, approximately 5 min after atezolizumab infusion & 2 h after cabozantinib dose) and predose on C2D1 and C3D1. | | |
| Blood sample-Pharmacogenetic (Section 5.6.7) | | | | | | |
| Blood sample-immune cell profiling by FACS[j] (Section 5.6.7) | | | Predose on C1D1 and C2D1. (may be performed at selected sites) | | | |
| Blood sample-serum/plasma biomarker[j] (Section 5.6.7) | | | | Predose on C1D1, C2D1, and C3D1 An optional sample may be collected at the first sign of progression per the investigator. | | |
| Blood sample-cell and/or plasma pharmacogenomics[j] (Section 5.6.7) | | | | Predose on C1D1, C2D1, and C3D1 An optional sample may be collected at the first sign of progression per the investigator. | | |

*Pharmacokinetic and Biomarker Blood Sample Assessment for the Cabozantinib Run-In Dosing Schedule*

| PK blood samples[k] (Section 5.6.6.1) | predose | X | | C1D1 (before treatment and 2 h after cabozantinib dose) and predose on C2D1 and C3D1. | | |
|---|---|---|---|---|---|---|
| Blood sample-Pharmacogenetic (Section 5.6.7) | | | | | | |
| Blood sample-immune cell profiling by FACS[j] (Section 5.6.7) | | | Predose on C1D1 and C2D1. (may be performed at selected sites) | | | |
| Blood sample-serum/plasma biomarker[j] (Section 5.6.7) | | | | Predose on C1D1, C2D1, and C3D1 An optional sample may be collected at the first sign of progression per the investigator. | | |
| Blood sample-cell and/or plasma pharmacogenomics[j] (Section 5.6.7) | | | | Predose on C1D1, C2D1, and C3D1 An optional sample may be collected at the first sign of progression per the investigator. | | |
| Concomitant medication (Section 7) | Document concomitant medication taken from 28 days before first dose of study treatment through 30 days after the date of the decision to discontinue study treatment | | | | | |
| Adverse events (Sections 8.1, 8.2, and 8.3.1) | Document new or worsening AEs from informed consent through 30 days (90 days for AESIs) after the date of the decision to permanently discontinue study treatment. AE information will be collected at study visits and may also be collected at any time over the phone or by spontaneous subject report. At the date of the first dose of study treatment, AEs will be documented pre- and post-dose. Certain AEs and all SAEs that are ongoing 30 days after of the date of the decision to permanently discontinue study treatment are to be followed until resolution or determination by the investigator that the event is stable or irreversible (see Section 8.4). | | | | | |
| Atezolizumab dosing[j] | Atezolizumab will be administered by IV infusion at the clinic. | | | | | |

APPENDIX B-continued

Schedule of Assessments for the Expansion Stage

| Assessment: | Pre-enrollment Screening[a] (Before First Dose) | Post-enrollment | | | |
|---|---|---|---|---|---|
| | | Cycle 1 (±3 days) | Cycles 2 through 8 (±3 days) | Cycles 9 and Above (15 days) | 30-Day Post-Treatment Follow-Up (+14 days) | Extended Follow Up |
| Cabozantinib dosing (Section 6.2) | | Standard Dosing Schedule: first infusion on C1D1; Cabozantinib Run-In Dosing Schedule: first infusion C2D1. Subsequent atezolizumab infusions will be administered every three weeks (−2 days) on Day 1 of each cycle until study treatment is discontinued. | | | | |
| | | Cabozantinib will administered in clinic C I DI and then will be taken once daily at home until study treatment is discontinued | | | | |
| Dispense/return of oral study drug and compliance accounting (Section 6.3) | | Cabozantinib is to be dispensed to subjects every 3 weeks | | | | |
| Additional anticancer treatment and survival status (Sections 5.3 and 5.6.10) | | | | (±7 days) after 30-day | | Every 12 weeks post-treatment follow-up visit until death |

[a]Results of screening assessments must be reviewed before first dose of study treatment to confirm that the subject meets the eligibility criteria.
[b]Informed consent may be obtained greater than 28 days prior to first dose of study treatment, but must be provided before any study-specific procedures are performed; however evaluations performed as part of routine care prior to informed consent can be utilized as screening evaluations if permitted by the site's IRB/EC policies.
[c]Symptom-directed physical examination will be conducted on C1D1 before first dose of study treatment and at subsequent safety assessment visits.
[d]Vital signs should always be assessed within 60 min prior to initiation of atezolizumab infusions, and further vital sign assessment should be performed during and after the infusion as clinically indicated.
[e]Additional ECGs are to be performed if clinically indicated.
[f]This assessment is intended to confirm suitability for treatment after screening and prior to first dose. If this assessment has been performed during screening within 14 days (7 days for pregnancy test) prior to first dose (C1D1), this assessment does not need to be performed on C1D1 unless the subject's clinical status has changed (eg, onset of new symptoms indicative of clinical deterioration). If the assessment is performed on C1D1, the results must be available to and reviewed by the investigator prior to any treatment being administered.
[g]Serum chemistry, hematology, and urinalysis laboratory samples must be collected and the results must be reviewed within 72 h before any atezolizumab infusion administered on study.
[h]Local laboratory assessments for these panels may be obtained and used if the results are required by the investigator in a rapid timeframe. See Section 5.6.5 and the Laboratory Manual for more detailed information on laboratory assessments.
Hepatitis B surface antigen and Hepatitis C antibody (with reflex testing HCV RNA if antibody test is positive) to be assessed at screening.
Tumor tissue (archival) will be obtained prior to first dose of study treatment whenever available. Formalin-fixed paraffin embedded (FFPE) tumor blocks are preferred but in cases where this is not possible, 12 unstained freshly cut FFPE slides should be obtained. See Translational Medicine Laboratory Manual for specific instructions.
[i]After C1D1, PK samples should be collected approximately 8 or more hours after the previous dose of cabozantinib, and if cabozantinib will be administered on that day, PK samples should be collected prior to cabozantinib administration. The investigator will ask the subject for the date and time of the most recent prior dose of cabozantinib, and this information will be recorded on the appropriate CRF page.
[j]An additional blood sample should be collected if an optional tumor tissue sample is obtained and such tissue sample collection does not coincide with scheduled blood collection for biomarker analysis
m Atezolizumab doses are not to be administered less than 19 days apart.

Appendix C: Maintenance Phase

When sufficient data have been collected to adequately evaluate all study endpoints, and upon site notification by the Sponsor, subjects remaining on study treatment will enter the study Maintenance Phase. Upon initiation of the Maintenance Phase, the Sponsor considers the safety and efficacy profile of the drug within this study to have been sufficiently established for regulatory purposes.

In the Maintenance Phase subjects will continue to receive study treatment until a criterion for protocol-defined discontinuation has been met (protocol Section 3.8). Subjects are to undergo periodic safety assessments (including local laboratory tests) and tumor assessments; the nature and frequency of these assessments are to be performed per standard of care. It is the Investigator's responsibility to ensure that subject visits occur frequently enough and adequate assessments are performed to ensure subject safety.

In order to continue to collect important safety information on subjects still enrolled in the study, reporting of SAEs, AESIs, and other reportable events (pregnancy and medication errors with sequalae) is to continue per protocol (Section 8.2.1).

Further, the following AEs, whether serious or not, are to be reported using the same process as for reporting SAEs described in protocol Section 8.2 (though SAE reporting timeline requirements do not apply to non-serious events reported in these categories):

Adverse Events (including irAEs), whether serious or not, leading to study treatment discontinuation Adverse Events (including IrAEs), whether serious or not, leading to study treatment dose modification (ie, causing study treatment to be interrupted, delayed, or reduced)

Study drug accountability is to continue as described in Section 6.4.

See Maintenance Phase Schedule of Assessments below. To receive study treatment supplies it may be necessary for subjects to visit the study site more frequently than clinic visits for safety and tumor evaluations performed per standard of care.

Site monitoring visits will occur at a reduced frequency to ensure adherence to GCP, protocol compliance, adequate subject safety follow-up, study drug accountability, and reporting of SAEs and other reportable events.

During the Maintenance Phase no data are to be entered into CRFs. Study central laboratory samples are not to be obtained. Do not submit local laboratory results to the study local laboratory management vendor.

Schedule of Assessments for the Maintenance Phase

| Assessment | Study Period/Visit | |
|---|---|---|
| | While Subject is Receiving Study Treatment (Until Treatment is Permanently Discontinued) | Post-Treatment Follow-Up Visit |
| Study drug accountability | Every time study drug is dispensed | s/[a] |
| Study treatment | Atezolizumab: Once every 3 weeks (−2 days); Cabozantinib: Daily Study treatment may continue until a criterion for discontinuation is met (Section 3.6). Subjects may be allowed to discontinue treatment with one component of the combination and continue on the other with the notification | |
| Safety evaluation: Clinical examination and local laboratory | Frequency per standard of care | |
| Reporting of SAEs, AESIs, and other reportable events (pregnancy and medication errors with sequelae) | Submit reports to Sponsor per Section 8.2 | |
| Reporting of AEs (including irAEs), serious or not: leading to study treatment discontinuation leading to study treatment dose modification (ie, causing study treatment to be interrupted, delayed, or reduced) | Submit reports to Sponsor per the same process as for reporting SAEs per Section 8.2 SAE reporting timeline requirements do not apply to non-serious events reported in these categories | |
| Tumor assessments: Imaging methods per SOC | Frequency per standard of care | |

AE, adverse event; irAE, immune-related adverse event; SAE, serious adverse event; SOC, standard of care.
No data will be entered into electronic case report forms. Do not submit local laboratory results to the study local laboratory management vendor, radiographic images to the study central imaging vendor.
[a] A post-treatment visit may be required for the purpose of returning all unused study medication still in the subject's possession.

Appendix D: Preexisting Autoimmune Diseases and Immune Deficiencies

Subjects should be carefully questioned regarding their history of acquired or congenital immune deficiencies or autoimmune disease. Subjects with any history of immune deficiencies or autoimmune disease listed in the table below are excluded from participating in the study. Possible exceptions to this exclusion could include:

Subjects with a medical history of such entities as atopic disease or childhood arthralgias where the clinical suspicion of autoimmune disease is low Subjects with a history of autoimmune-related hypothyroidism on a stable dose of thyroid replacement hormone, controlled Type 1 diabetes mellitus and on an insulin regimen, or asthma that requires intermittent use of bronchodilators Subjects with transient autoimmune manifestations of an acute infectious disease that resolved upon treatment of the infectious agent (eg, acute Lyme arthritis)

Contact the Sponsor regarding any uncertainty over autoimmune exclusions.

Autoimmune Disease and Immune Deficiencies

Acute disseminated encephalomyelitis
Addison disease
Ankylosing spondylitis
Antiphospholipid antibody syndrome
Aplastic anemia
Autoimmune hemolytic anemia
Autoimmune hepatitis
Autoimmune hypoparathyroidism
Autoimmune hypophysitis
Autoimmune myocarditis
Autoimmune oophoritis
Autoimmune orchitis
Autoimmune thrombocytopenic purpura
Behcet disease
Bullous pemphigoid
Chronic fatigue syndrome
Chronic inflammatory demyelinating polyneuropathy
Churg-Strauss syndrome
Crohn disease
Dermatomyositis
Diabetes mellitus type 1
Dysautonomia
Epidermolysis bullosa acquisita
Gestational pemphigoid
Giant cell arteritis
Goodpasture syndrome
Graves disease
Guillain-Barre syndrome
Hashimoto disease
IgA nephropathy
Inflammatoiy bowel disease
Interstitial cystitis
Kawasaki disease
Lambert-Eaton myasthenia syndrome
Lupus erythematosus
Lyme disease - chronic
Meniere syndrome
Mooren ulcer
Morphea
Multiple sclerosis
Myasthenia gravis
Neuromyotonia
Opsoclonus myoclonus syndrome
Optic neuritis
Ord thyroiditis
Pemphigus
Pernicious anemia
Polyarteritis nodosa
Polyarthritis
Polyglandular autoimmune syndrome
Primary biliary cirrhosis
Psoriasis
Reiter syndrome
Rheumatoid arthritis
Sarcoidosis
Scleroderma
Sjogren's syndrome
Stiff-Person syndrome
Takayasu arteritis
Ulcerative colitis
Vitiligo
Vogt-Koyanagi-Harada disease
Wegener granulomatosis

APPENDIX E

Performance Status Criteria

| ECOG Performance Status Scale | | Karnofsky Performance Status Scale | |
|---|---|---|---|
| Grade | Descriptions | Percent | Description |
| 0 | Normal activity. Fully active, able to carry on all pre-disease performance | 100 | Normal, no complaints, no evidence of disease. |
| | | 90 | Able to carry on normal activity; minor signs or symptoms of disease. |
| 1 | Symptoms, but ambulatory. Restricted in physically strenuous activity, but ambulatory and able to carry out work of a light or sedentary nature (eg, light housework, office work). | 80 | Normal activity with effort; some signs or symptoms of disease. |
| | | 70 | Cares for self, unable to carry on normal activity or to do active work. |
| 2 | In bed <50% of the time. Ambulatory and capable of all self-care, but unable to carry out any work activities. Up and about more than 50% of waking hours. | 60 | Requires occasional assistance, but is able to care for most of his/her needs. |
| | | 50 | Requires considerable assistance and frequent medical care. |
| 3 | In bed >50% of the time. Capable of only limited self-care, confined to bed or chair more than 50% of waking hours. | 40 | Disabled, requires special care and assistance. |
| | | 30 | Severely disabled, hospitalization indicated. Death not imminent. |
| 4 | 100% bedridden. Completely disabled. Cannot carry on any self-care. Totally confined to bed or chair. | 20 | Very sick, hospitalization indicated. Death not imminent. |
| | | 10 | Moribund, fatal processes progressing rapidly. |
| 5 | Dead. | 0 | Dead. |

Appendix F: Response Evaluation Criteria in Solid Tumors Version 1.1 (RECIST 1.1) Adapted from Eisenhauer et al 2009

Definitions

Baseline: Baseline is defined as the most recent assessment performed prior to receiving study treatment. Baseline assessments must be performed within the period defined in the protocol eligibility criteria.

Measurable lesions: Except for lymph nodes as described below, measurable lesions are defined as those that can be accurately measured in at least 1 dimension (longest diameter to be recorded) as >10 mm with CT scan (if CT scans have slice thickness greater than 5 mm the minimum size for a measurable lesion is twice the slice thickness).

To be considered pathologically enlarged and measurable, a lymph node must be >15 mm in short axis when assessed by CT scan (CT scan slice thickness recommended to be no greater than 5 mm). At baseline and in follow-up, only the short axis will be measured and recorded.

MRI may be substituted for contrast-enhanced CT for lesions at some anatomical sites, but not for lesions in the lungs. The minimum size for measurability is the same as for CT (10 mm) a long as the scans we performed with slice thickness of S mm and no gap. If MRI is performed with thicker slices, the size of a measurable lesion at baseline should be twice the slice thickness. In the event there are interslice gaps, this also needs to be considered in determining the size of measurable lesions at baseline.

Nonmeasurable lesions: All other lesions (or sites of disease), including small lesions (longest diameter <10 mm or pathological lymph nodes with >10 to <15 mm short axis), are considered nonmeasurable. Lymph nodes that have a short axis <10 mm are considered nonpathological and are not be recorded or followed. Bone lesions, leptomeningeal disease, ascites, pleural/pericardial effusions, lymphangitis cutis/pulmonitis, and abdominal masses (not followed by CT or MRI), are considered as nonmeasurable.

Target lesions: All measurable lesions up to a maximum of 2 lesions per organ and 5 lesions in total, representative of all involved organs, are to be identified as target lesions and measured and recorded at baseline. Target lesions are to be selected on the basis of their size (lesions with the longest diameter), be representative of all involved organs, and be those that lend themselves to reproducible repeated measurements. It may be the case that, on occasion, the largest lesion does not lend itself to reproducible measurement in which circumstance the next largest lesion which can be measured reproducibly should be selected. Target lesions will be measured at each assessment (longest axis for nonnodal lesions, shortest axis for measurable malignant nodal lesions).

Nontarget lesions: All other lesions (or sites of disease) including all non-measurable lesions (including pathological lymph nodes with >10 to <15 mm short axis) and all measurable lesions over and above the S target lesions are to be identified as son-target lesions and recorded at baseline. Measurements of these lesions are not required, but the presence, absence, or in rare cases unequivocal progression of each is to be recorded throughout follow-up. Lymph nodes that have a short axis <10 mm are considered non-pathological and are not to be recorded or followed.

To be considered progression of non-target lesions in the presence of measurable disease, unequivocal progression is defined as substantial worsening in non-target disease such that, even in the presence of SD or PR in target disease, the overall tumor burden has increased sufficiently to merit discontinuation of the therapy.

Special Consideration

Lesions by clinical examination will not be used for response in this study.

Cystic Lesions

Cystic lesions that meet the criteria for radiographically defined simple cysts should not be considered as malignant lesions (neither measurable nor nonmeasurable) since they are, by definition, simple cysts.

Cystic lesions thought to represent cystic metastases can be considered as measurable lesions, if they meet the definition of measurability described above. However, if noncystic lesions are present in the same subject, these are preferred for selection as target lesions.

Bone Lesions

Bone scan, PET scan or plain films are not considered adequate imaging techniques to measure bone lesions.

Lytic bone lesions or mixed lytic-blastic lesions, with identifiable soft tissue components, that can be evaluated by cross-sectional imaging techniques such as CT or MRI can be considered as measurable lesions if the soft tissue component meets the definition of measurability described above.

Blastic bone lesions are non-measurable.

Lesions with Prior Local Treatment

Lesions situated in a previously irradiated area, or in an area subjected to other loco-regional therapy, are not considered measurable.

Imaging Methods

The same method of assessment and the same technique used to characterize each identified and reported lesions at baseline should be used during each follow-up assessment. All measurements should be taken and recorded in metric notation using a ruler or calipers. Imaging based evaluation is preferred to evaluation by clinical examination unless the lesion(s) being followed cannot be imaged but assessed by clinical examination (referring to biopsy-proven visible lesion(s) on the chest).

Chest x-ray: Chest x-ray will not be used for response assessment in this study.

Conventional CT and MRI: This guideline has defined measurability of lesions on CT scan based on the assumption that CT slice thickness is 5 mm or less. If CT scans have slice thickness greater than S mm, the minimum size for a measurable lesion is twice the slice thickness. MRI is also acceptable in certain situations (eg, for body scan) except for lung.

Use of MRI remains a complex issue. MRI has excellent contrast, spatial, and temporal resolution; however, there are many image acquisition variables involved in MRI, which greatly impact image quality, lesion conspicuity, and measurement. Furthermore, the availability of MRI is variable globally. As with CT, if an MRI is performed, the technical specifications of the scanning sequences used should be optimized for the evaluation of the type and site of disease. Furthermore, as with CT, the modality used at follow-up should be the same as was used at baseline and the lesions should be measured/assessed on the same pulse sequence. It is beyond the scope of the RECIST guidelines to prescribe specific MRI pulse sequence parameters for all scanners, body parts, and diseases. Ideally, the same type of scanner should be used and the image acquisition protocol should be followed as closely as possible to prior scans. Body scans should be performed with breath-hold scanning techniques, if possible.

Positron emission tomography will not be used for response assessment in this study. Ultrasound: Ultrasound will not be used for response assessment in this study.

Bone scans will be used to assess the presence or disappearance of the bone component of bone lesions. CT or MRI scan will be used to confirm results of bone scans. Preferred method for confirmation is MRI.

Tumor Markers: Tumor markers may be evaluated for changes but will not be used to determine progressive disease in this study.

Cytology, Histology: The origin of any effusion that appears or worsens during treatment will be considered malignant unless cytologically confirmed.

Time Point Assessments

The frequency and schedule of tumor assessments is defined in the protocol. The schedule is to be maintained regardless of whether study treatment is reduced, interrupted, delayed, or discontinued.

At baseline, tumors and lymph nodes are classified and documented as target or nontarget lesions per the definitions provided above. It is possible to record multiple nontarget lesions involving the same organ as a single item (eg, 'multiple liver metastases'). At all postbaseline (follow-up) evaluations the baseline classification (target, nontarget) is to be maintained and lesions are to be documented and described in a consistent fashion over time (eg, recorded in the same order on source documents).

At each assessment, a sum of the diameters (longest for nonnodal lesions, short axis for nodal lesions) for all target lesions will be calculated and included in source documents.

The baseline sum of the diameters (SoD) will be used as reference to further characterize any objective tumor regression in the measurable dimension of the disease. The lowest SoD (nadir) since (and including) the baseline value will be used as reference for evaluating progression.

After baseline, target lesions should have the actual size documented, if possible, even if the lesions become very small. If in the opinion of the radiologist the lesion has likely disappeared, 0 mm should be recorded. If the lesion is present but too small to measure, an indicator for 'too small to measure' this should be included in source documents.

For target lesions, measurements should be taken and recorded in metric notation. All tumor measurements must be recorded in millimeters.

Nontarget lesions are to be assessed qualitatively (present, resolved, or unequivocal progression) and new lesions, if any, are to be documented separately.

At each evaluation, progression status is to be determined based upon the time point status for target lesions, nontarget lesions, and new lesions.

Finding of new lesions should not be attributable to differences in scanning technique, change in imaging modality or findings thought to represent something other than tumor. Necrosis of preexisting lesions as part of a response to treatment should be excluded before defining a 'new' cystic lesion. A lesion identified on a follow-up study in an anatomical location that was not scanned at baseline is considered a new lesion. If a new lesion is equivocal because of its small size, repeat scans need to confirm there is definitely a new lesion, and progression should be declared using the date of the initial scan.

Time point progression cannot be based solely on bone scan findings. Bone scans are to be used to direct corroborative imaging with CT/MRI if necessary. These CT/MRI findings will be used for the determination of progression.

| Target Lesion Time Point Response (TPR) | |
|---|---|
| Complete Response (CR) | Disappearance of all target lesions. All pathological lymph nodes (whether target or non-target) must have reduction in short axis to <10 mm. |
| Partial Response (PR) | At least a 30% decrease in SoD of target lesions, taking as a reference the baseline SoD. |
| Stable Disease (SD) | Neither sufficient shrinkage to qualify for PR nor sufficient increase to qualify for PD. |
| Progressive Disease (PD) | At least a 20% increase in the SoD of target lesions, taking as a reference the smallest (nadir) SoD since (and including) baseline. In addition to the relative increase of 20%, the SoD must also demonstrate an absolute increase of at least 5 mm. |
| Not Applicable (NA) | No target lesion identified at baseline. |
| Unable to Evaluate (UE) | One or more target lesions are not imaged and the remainder of the SoD compared with the nadir SoD does not meet the criterion for PD. |

SoD, baseline sum of diameters (longest for non-nodal lesions; short axis for nodal lesions).
If the target lesion for a subject meet the criteria for both PR and PD at a given time point, the target lesion response is PD.
If the nadir of SoD is 0 (ie, the subject had a prior target lesion CR), the reappearance of any prior target lesion to any degree constitutes PD.

| Non-Target Lesion Time Point Response (TPR) | |
|---|---|
| Complete Response (CR) | Disappearance of all non-target lesions. All lymph nodes must be non-pathological in size (<10 mm short axis). |
| Non-CR/Non-PD | Persistence of one or more non-target lesion(s). |
| Progressive Disease (PD) | Unequivocal progression of non-target lesions. Unequivocal progression should normally not trump target lesion status. It must be representative of overall disease status change, not a single lesion increase. |
| Not Applicable (NA) | No non-target lesions identified at screening. |
| Unable to Evaluate (UE) | One or more non-target lesions are not imaged and the remaining non-target lesions do not meet the criterion for PD. |

| New Lesion Time Point Response (TPR) | |
|---|---|
| Yes | Lesion present at follow-up visit either for the very first time or reappearing (ie, lesion was present at baseline, disappeared at a follow-up visit and re-appeared later). Note: The appearance of one or more new lesions on CT or MRI scan is considered progression if these findings are unequivocally not due to a change in the imaging technique or modality. On bone scan, new lesions are not sufficient to qualify as PD. Confirmation should be obtained by performing CT or MRI of the area of concern to confirm results of bone scan. Preferred method for confirmation is MRI. |
| No | No new lesions present at follow-up. |
| Unable to Evaluate (UE) | Subject not assessed or incompletely assessed for new lesions. |

| Evaluation of Overall Time Point Response | | | |
|---|---|---|---|
| Target Lesion TPR | Non-target lesion TPR | New lesion TPR | Overall TPR |
| CR | CR or NA | No | CR* |
| CR | Non-CR/non-PD | No | PR* |
| CR | UE | No | PR* |
| PR | Any except PD | No | PR* |
| SD | Any except PD | No | SD |
| UE | Any except PD | No | UE |
| PD | Any | No or Yes or UE | PD |
| Any | PD | No or Yes or UE | PD |
| Any | Any | Yes | PD** |
| NA | CR | No | CR* |
| NA | Non-CR/Non-PD | No | Non-CR/non-PD |
| NA | UE | No | UE |

CR, complete response; PR, partial response; SD, stable disease; PD, progressive disease, UE, unable to evaluate; NA, not applicable (no such lesions at screening); Any, CR, PR, SD, PD, NA, or UE.
The overall response at a given time point does not depend upon the overall response assigned at any prior or subsequent time point (ie, confirmation requirement are not considered when assigning time point responses).
*Subjects with an overall response of CR or PR must have a repeat tumor assessment performed no less than 4 weeks after the criteria for response are first met. However, the presence or absence of confirmation is not considered when assigning a time point response.
**If a lesion disappears and reappears at a subsequent time point it should continue to be measured. However, the subject's response at the point in time when the lesion reappears will depend upon the status of his/her other lesions. For example, if the subject's tumor had reached a CR status and the lesion reappeared, then the subject would be considered PD at the time of reappearance. In contrast, if the tumor status was a PR or SD and one lesion which had disappeared then reappears, its maximal diameter should be added to the sum of the remaining lesions for a calculated response.

Confirmation

The main goal of confirmation of objective response is to avoid overestimating the response rate observed. For subjects with an overall response of PR or CR at a given time point, changes in tumor measurements must be confirmed by repeat assessments that should be performed no less than 4 weeks after the criteria for response are first met. However, the presence or absence of confirmation is not considered when assigning a time point response. Longer intervals as determined by the study protocol may also be appropriate.

Best Overall Response

Best overall response, incorporating confirmation requirements, will be derived during statistical analysis from the series of time point responses and need not be considered when assigning response at each time point.

Appendix G: Immune-Related Response Criteria (Modified RECIST)

Immune-related Response Criteria (modified RECIST) are adapted from Wolchock et al 2009 and Nishino et al 2013.

Key aspects of modified RECIST for immune-related response assessment:

New lesions:
New lesions after baseline do not necessarily define radiographic progression
New measurable lesions are added into the total tumor burden and followed at subsequent tumor assessments
Unmeasurable new lesions preclude complete response status Non-target lesions:
Non-target lesion progression does not define radiographic progression
Disappearance of all non-target lesions is required for complete response status Radiographic progression:
Is determined only on the basis of measurable disease
Is defined by a >20% increase of sum of lesion diameter (SLD; including measurable new lesions)
Radiographic progression that is not confirmed >4 weeks from the first date documented is not radiographic progression by immune-response criteria
Best response may occur after any number of radiographic progression assessments Evaluation of Overall Immune-related Time Point Response by modified RECIST Criteria

| Target Lesion TPR | Non-Target Lesion TPR | New Measurable Lesion | New Non-Measurable Lesion | % Change in irSLD Tumor Burden (Including Measurable New Lesions) | Overall Immune-Related TPR |
|---|---|---|---|---|---|
| CR | CR | No | No | −100% | irCR |
| PR | Any | Any | Any | <−30% | irPR |
| SD | Any | Any | Any | >−30% to <+20% | irSD |
| PD | Any | Any | Any | >+20% | irPD |

CR, complete response; PR, partial response; SD, stable disease; PD, progressive disease; ir, immune-related; SLD, sum of lesion diameter; TPR, time-point response.

Time point responses and best overall response per modified RECIST, incorporating confirmation requirements, will be derived during statistical analysis from the tumor evaluations performed by the investigator.

APPENDIX H

| Infusion-Related Reaction Guidelines | |
|---|---|
| Infusion-Related Reaction Grading by NCI CTCAE version 4.0 | Infusion-Related Reaction Management Guideline |
| Grade 1: Mild transient reaction; infusion interruption not indicated; intervention not indicated | Monitor vital signs as clinically indicated |
| Grade 2: Infusion interruption indicated but responds promptly to symptomatic treatment (e.g., antihistamines, NSAIDs, narcotics, IV fluids); prophylactic medication indicated for <24 hours | Interrupt infusion Provide adequate supportive therapy (examples: antihistamines, acetaminophen, NSAIDs, IV fluids, narcotics) Monitor vital signs as clinically indicated Atezolizumab infusion may be restarted at a lower infusion rate if symptoms resolve promptly after initiation of supportive therapy Premedication is required for next scheduled atezolizumab infusion. Consider permanent discontinuation of atezolizumab treatment if Grade 2 infusion reaction occurs despite adequate premedication |
| Grade 3: Prolonged (ie, not rapidly responsive to symptomatic medication and/or brief interruption of infusion); recurrence of symptoms following initial improvement; hospitalization indicated for other clinical sequelae | Interrupt infusion Provide adequate supportive therapy (examples: antihistamines, acetaminophen, NSAIDs, IV fluids, narcotics, corticosteroids, epinephrine, oxygen pressor or ventilator) Monitor vital signs as clinically indicated |
| Grade 4: Life-threatening consequences; urgent intervention indicated | Hospitalization indicated for clinical sequelae (examples: renal impairment, pulmonary infiltrates) Discontinue permanently atezolizumab treatment |

IV, intravenous; NSAID, non-steroidal anti-inflammatory drugs; PO, orally administered.
Appropriate medical staff and resuscitation equipment should be available during the infusion therapy with atezolizumab
Premedication for subsequent atezolizumab infusions:
Premedication may be administered approximately 1.5 hours before the infusion of atezolizumab.
Examples: Diphenhydramine 50 mg PO and acetaminophen 500-1000 mg PO or similar medications at equivalent doses
Reference: Doessegger and Banholzer 2015

The invention claimed is:

1. A method of treating locally advanced or metastatic solid tumors, comprising administering a patient in need of such treatment a compound of formula I:

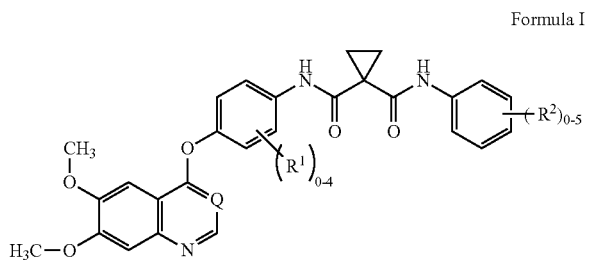

Formula I or a pharmaceutically acceptable salt thereof or a pharmaceutical composition comprising the compound of formula I or the pharmaceutically acceptable salt thereof, and a pharmaceutically acceptable carrier, wherein:
$R^1$ is halo;
$R^2$ is halo; and
Q is CH or N;
in combination with atezolizumab, wherein the locally advanced or metastatic solid tumor is castration-recurrent prostate cancer (CRPC).

2. The method of claim 1, wherein the compound of formula I is compound 1 having the formula:

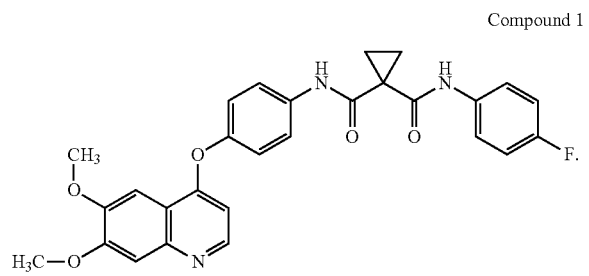 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof.

3. The method of claim 2, wherein compound 1 is administered as the L-malate salt.

4. The method of claim 2, wherein compound 1 is administered as the D-malate salt.

5. The method of claim 2, wherein atezolizumab is administered intravenously (IV).

6. The method of claim 2, wherein Compound 1 or the pharmaceutically acceptable salt thereof and atezolizumab are administered concurrently or sequentially.

7. The method of claim 2, wherein up to and including 1,200 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof, once daily with fasting.

8. The method of claim 7, wherein up to and including 1,200 mg of atezolizumab is administered to the patient once every three weeks in combination with 60 mg, 40 mg, or 20 mg of compound 1, or a pharmaceutically acceptable salt thereof, once daily with fasting.

9. The method of claim 2, wherein up to and including 1,100 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof, once daily with fasting.

10. The method of claim 9, wherein up to and including 1,100 mg of atezolizumab is administered to the patient once every three weeks in combination with 60 mg, 40 mg, or 20 mg of compound 1, or a pharmaceutically acceptable salt thereof, once daily with fasting.

11. The method of claim 2, wherein up to and including 1,000 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof, once daily with fasting.

12. The method of claim 11, wherein up to and including 1,000 mg of atezolizumab is administered to the patient once every three weeks in combination with 60 mg, 40 mg, or 20 mg of compound 1, or a pharmaceutically acceptable salt thereof, once daily with fasting.

13. The method of claim 2, wherein up to and including 900 mg of atezolizumab is administered to the patient once every three weeks in combination with 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg of compound 1, or a pharmaceutically acceptable salt thereof, once daily with fasting.

14. The method of claim 13, wherein up to and including 900 mg of atezolizumab is administered to the patient once every three weeks in combination with 60 mg, 40 mg, or 20 mg of compound 1, or a pharmaceutically acceptable salt thereof, once daily with fasting.

15. The method of claim 7, wherein Compound 1, or a pharmaceutically acceptable salt thereof, and atezolizumab are administered concurrently or sequentially.

16. The method of claim 6, wherein the atezolizumab is administered intravenously via infusion over 60 minutes or 30 minutes.

17. The method of claim 2, wherein stable disease is observed in patients being treated with the combination.

* * * * *